(12) United States Patent
Shu et al.

(10) Patent No.: US 8,349,003 B2
(45) Date of Patent: *Jan. 8, 2013

(54) SUTURE LOCKING ASSEMBLY AND METHOD OF USE

(75) Inventors: Mark Shu, Rancho Santa Margarita, CA (US); Chris Coppin, Carlsbad, CA (US); Louis A. Campbell, Austin, TX (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/085,183

(22) Filed: Apr. 12, 2011

(65) Prior Publication Data

US 2011/0190878 A1  Aug. 4, 2011

Related U.S. Application Data

(60) Division of application No. 10/792,186, filed on Mar. 3, 2004, now Pat. No. 7,959,674, which is a continuation-in-part of application No. 10/404,233, filed on Apr. 1, 2003, now Pat. No. 7,578,843, which is a continuation-in-part of application No. 10/196,527, filed on Jul. 16, 2002, now Pat. No. 7,172,625.

(51) Int. Cl.
*A61F 2/24* (2006.01)

(52) U.S. Cl. ........................................ 623/2.4

(58) Field of Classification Search .......... 623/2.1–2.42, 623/1.24, 1.26
See application file for complete search history.

(56) References Cited

U.S. PATENT DOCUMENTS

| | | |
|---|---|---|
| 3,143,742 A | 8/1964 | Cromie |
| 3,320,974 A | 5/1967 | High et al. |
| 3,370,305 A | 2/1968 | Goott et al. |
| 3,371,352 A | 3/1968 | Siposs |
| 3,409,013 A | 11/1968 | Berry |
| 3,464,065 A | 9/1969 | Cromie |
| 3,546,710 A | 12/1970 | Ivanovich et al. |
| 3,571,815 A | 3/1971 | Somyk |
| 3,574,865 A | 4/1971 | Hamaker |
| 3,628,535 A | 12/1971 | Ostrowsky et al. |
| 3,686,740 A | 8/1972 | Shiley |
| 3,691,567 A | 9/1972 | Cromie |
| 3,710,744 A | 1/1973 | Goodenough et al. |
| 3,744,060 A | 7/1973 | Bellhouse et al. |
| 3,755,823 A | 9/1973 | Hancock |
| 3,800,403 A | 4/1974 | Anderson |

(Continued)

FOREIGN PATENT DOCUMENTS

CN  2356656  1/2000

(Continued)

OTHER PUBLICATIONS

Lutter, et al., Percutaneous Valve Replacement: Current State and Future Prospects; Ann. Thorac. Surg. 2004;78:2199-2206.

(Continued)

*Primary Examiner* — Alvin J. Stewart

(57) ABSTRACT

A suture locking assembly for use with a heart valve repair device. The suture locking assembly including a rim and a suture band. The rim defines a first flange and a second flange spaced from the first flange. The rim is configured to extend at least partially around a periphery of the heart valve repair device. The suture band is maintained between the first flange and the second flange. The suture locking assembly is configured to securely maintain a suture segment that is pulled from a first position to a second position relative the suture locking assembly, the second position being at least partially defined near an outer periphery of the rim.

18 Claims, 39 Drawing Sheets

U.S. PATENT DOCUMENTS

| | | |
|---|---|---|
| 3,839,741 A | 10/1974 | Haller |
| 3,959,827 A | 6/1976 | Kaster |
| 3,996,623 A | 12/1976 | Kaster |
| 3,997,923 A | 12/1976 | Possis |
| 4,035,849 A | 7/1977 | Angell et al. |
| 4,078,268 A | 3/1978 | Possis |
| 4,078,468 A | 3/1978 | Civitello |
| 4,084,268 A | 4/1978 | Ionexcu et al. |
| 4,106,129 A | 8/1978 | Carpentier et al. |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,686,883 A | 8/1987 | Martin |
| 4,687,483 A | 8/1987 | Fisher et al. |
| 4,692,164 A | 9/1987 | Dzemeshkevich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,914,097 A | 4/1990 | Proudian et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,708 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,348 A | 3/1995 | Campbell et al. |
| 5,397,351 A | 3/1995 | Pavcnik et al. |
| 5,406,857 A | 4/1995 | Eberhardt et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A | 8/1996 | Vesely et al. |
| 5,549,666 A | 8/1996 | Hata et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov |
| 5,578,076 A | 11/1996 | Krueger et al. |
| 5,584,803 A | 12/1996 | Stevens et al. |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,669,917 A | 9/1997 | Sauer |
| 5,693,090 A | 12/1997 | Unsworth et al. |
| 5,695,503 A | 12/1997 | Krueger et al. |
| 5,713,952 A | 2/1998 | Vanney et al. |
| 5,713,953 A | 2/1998 | Vallana et al. |
| 5,716,370 A | 2/1998 | Williamson, IV et al. |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,603 A | 1/1999 | Reif |
| 5,860,992 A | 1/1999 | Daniel |
| 5,861,028 A | 1/1999 | Angell |
| 5,865,801 A | 2/1999 | Houser |
| 5,876,436 A | 3/1999 | Vanney et al. |
| 5,879,371 A | 3/1999 | Gardiner et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,908,452 A | 6/1999 | Bokros et al. |
| 5,910,170 A | 6/1999 | Reimink et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,969 A | 8/1999 | Carpentier et al. |
| 5,935,163 A | 8/1999 | Gabbay |
| 5,957,949 A | 9/1999 | Leonhardt et al. |

| Patent No. | Date | Inventor(s) |
|---|---|---|
| 5,961,549 A | 10/1999 | Nguyen et al. |
| 5,961,550 A | 10/1999 | Carpentier |
| 5,972,004 A | 10/1999 | Williamson, IV et al. |
| 5,972,024 A | 10/1999 | Northrup, III |
| 5,976,183 A | 11/1999 | Ritz |
| 5,984,959 A | 11/1999 | Robertson et al. |
| 5,984,973 A | 11/1999 | Girard et al. |
| 6,007,577 A | 12/1999 | Vanney et al. |
| 6,010,531 A | 1/2000 | Donlon et al. |
| 6,042,607 A | 3/2000 | Williamson, IV et al. |
| 6,045,576 A | 4/2000 | Starr et al. |
| 6,059,827 A | 5/2000 | Fenton, Jr. |
| 6,066,160 A | 5/2000 | Colvin et al. |
| 6,068,657 A | 5/2000 | Lapeyre et al. |
| 6,074,041 A | 6/2000 | Gardiner et al. |
| 6,074,418 A | 6/2000 | Buchanan et al. |
| 6,081,737 A | 6/2000 | Shah |
| 6,083,179 A | 7/2000 | Oredsson |
| 6,096,074 A | 8/2000 | Pedros |
| 6,099,475 A | 8/2000 | Seward et al. |
| 6,102,944 A | 8/2000 | Huynh |
| 6,106,550 A | 8/2000 | Magovern et al. |
| 6,110,200 A | 8/2000 | Hinnenkamp |
| 6,113,632 A | 9/2000 | Reif |
| 6,117,091 A | 9/2000 | Young et al. |
| 6,126,007 A | 10/2000 | Kari et al. |
| 6,129,758 A | 10/2000 | Love |
| 6,139,575 A | 10/2000 | Shu et al. |
| 6,143,024 A | 11/2000 | Campbell et al. |
| 6,143,025 A | 11/2000 | Stobie et al. |
| 6,149,658 A | 11/2000 | Gardiner et al. |
| 6,162,233 A | 12/2000 | Williamson, IV et al. |
| 6,165,183 A | 12/2000 | Kuehn et al. |
| 6,168,614 B1 | 1/2001 | Anderson et al. |
| 6,176,877 B1 | 1/2001 | Buchanan et al. |
| 6,183,512 B1 | 2/2001 | Hawanec, Jr. et al. |
| 6,197,054 B1 | 3/2001 | Hamblin, Jr. et al. |
| 6,200,306 B1 | 3/2001 | Klostermeyer |
| 6,203,553 B1 | 3/2001 | Robertson |
| 6,214,043 B1 | 4/2001 | Krueger et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,245,105 B1 | 6/2001 | Nguyen et al. |
| 6,254,636 B1 | 7/2001 | Peredo |
| 6,264,691 B1 | 7/2001 | Gabbay |
| 6,270,526 B1 | 8/2001 | Cox |
| 6,270,527 B1 | 8/2001 | Campbell et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,290,674 B1 | 9/2001 | Roue et al. |
| 6,299,638 B1 | 10/2001 | Sauter |
| 6,309,417 B1 | 10/2001 | Spence |
| 6,312,447 B1 | 11/2001 | Grimes |
| 6,312,465 B1 | 11/2001 | Griffin et al. |
| 6,319,280 B1 | 11/2001 | Schoon |
| 6,319,281 B1 | 11/2001 | Patel |
| 6,322,588 B1 | 11/2001 | Ogle et al. |
| 6,328,727 B1 | 12/2001 | Frazier et al. |
| 6,328,763 B1 | 12/2001 | Love et al. |
| 6,338,740 B1 | 1/2002 | Carpentier |
| 6,350,281 B1 | 2/2002 | Rhee |
| 6,358,278 B1 | 3/2002 | Brendzel et al. |
| 6,358,556 B1 | 3/2002 | Ding et al. |
| 6,371,983 B1 | 4/2002 | Lane |
| 6,391,053 B1 | 5/2002 | Brendzel et al. |
| 6,402,780 B2 | 6/2002 | Williamson, IV et al. |
| 6,409,759 B1 | 6/2002 | Peredo |
| 6,413,275 B1 | 7/2002 | Nguyen et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,447,524 B1 | 9/2002 | Knodel |
| 6,454,799 B1 | 9/2002 | Schreck |
| 6,458,153 B1 | 10/2002 | Bailey et al. |
| 6,461,382 B1 | 10/2002 | Cao |
| 6,468,305 B1 | 10/2002 | Otte |
| 6,503,272 B2 | 1/2003 | Duerig et al. |
| 6,514,265 B2 | 2/2003 | Ho et al. |
| 6,530,952 B2 | 3/2003 | Vesely |
| 6,547,827 B2 | 4/2003 | Carpentier et al. |
| 6,551,332 B1 | 4/2003 | Nguyen et al. |
| 6,558,418 B2 | 5/2003 | Carpentier et al. |
| 6,569,196 B1 | 5/2003 | Vesely |
| 6,582,462 B1 | 6/2003 | Andersen et al. |
| 6,585,766 B1 | 7/2003 | Huynh et al. |
| 6,589,279 B1 | 7/2003 | Anderson et al. |
| 6,598,307 B2 | 7/2003 | Love et al. |
| 6,602,289 B1 | 8/2003 | Colvin et al. |
| 6,607,541 B1 | 8/2003 | Gardiner et al. |
| 6,613,059 B2 | 9/2003 | Ho et al. |
| 6,613,085 B1 | 9/2003 | Anderson et al. |
| 6,641,593 B1 | 11/2003 | Schaller et al. |
| 6,652,578 B2 | 11/2003 | Bailey et al. |
| 6,676,671 B2 | 1/2004 | Robertson et al. |
| 6,678,862 B1 | 1/2004 | Love et al. |
| 6,682,559 B2 | 1/2004 | Myers et al. |
| 6,685,739 B2 | 2/2004 | DiMatteo et al. |
| 6,692,513 B2 | 2/2004 | Streeter et al. |
| 6,695,859 B1 | 2/2004 | Golden et al. |
| 6,709,457 B1 | 3/2004 | Otte et al. |
| 6,716,243 B1 | 4/2004 | Colvin et al. |
| 6,716,244 B2 | 4/2004 | Klaco |
| 6,719,789 B2 | 4/2004 | Cox |
| 6,719,790 B2 | 4/2004 | Brendzel et al. |
| 6,730,118 B2 | 5/2004 | Spenser et al. |
| 6,733,525 B2 | 5/2004 | Yang |
| 6,764,508 B1 | 7/2004 | Roehe et al. |
| 6,767,362 B2 | 7/2004 | Schreck |
| 6,769,434 B2 | 8/2004 | Liddicoat et al. |
| 6,776,785 B1 | 8/2004 | Yencho |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,830,585 B1 | 12/2004 | Artof et al. |
| 6,833,924 B2 | 12/2004 | Love et al. |
| 6,837,902 B2 | 1/2005 | Nguyen et al. |
| 6,846,324 B2 | 1/2005 | Stobie |
| 6,846,325 B2 | 1/2005 | Liddicoat |
| 6,872,226 B2 | 3/2005 | Cali et al. |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,908,481 B2 | 6/2005 | Cribier |
| 6,911,043 B2 | 6/2005 | Myers et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,929,653 B2 | 8/2005 | Streeter |
| 6,939,365 B1 | 9/2005 | Fogarty et al. |
| 6,945,980 B2 | 9/2005 | Nguyen et al. |
| 6,945,997 B2 | 9/2005 | Huynh et al. |
| 6,960,221 B2 | 11/2005 | Ho et al. |
| 7,011,681 B2 | 3/2006 | Vesely |
| 7,025,780 B2 | 4/2006 | Gabbay |
| 7,037,333 B2 | 5/2006 | Myers et al. |
| 7,070,616 B2 | 7/2006 | Majercak et al. |
| 7,083,648 B2 | 8/2006 | Yu |
| 7,097,659 B2 | 8/2006 | Woolfson et al. |
| 7,101,396 B2 | 9/2006 | Artof et al. |
| 7,134,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 | 2/2007 | Hill et al. |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |

| Patent/Publication | Date | Name |
|---|---|---|
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,513,909 B2 | 4/2009 | Lane et al. |
| 7,547,313 B2 | 6/2009 | Gardiner et al. |
| 7,556,647 B2 | 7/2009 | Drews et al. |
| 7,578,843 B2 | 8/2009 | Shu |
| 7,597,711 B2 | 10/2009 | Drews et al. |
| 7,708,775 B2 | 5/2010 | Rowe et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat et al. |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077698 A1 | 6/2002 | Peredo |
| 2002/0091441 A1 | 7/2002 | Nguyen et al. |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Bonhoeffer et al. |
| 2003/0036795 A1 | 2/2003 | Andersen et al. |
| 2003/0040792 A1 | 2/2003 | Gabbay |
| 2003/0045902 A1 | 3/2003 | Weadeock |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 | 3/2004 | Woolfson |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0122514 A1 | 6/2004 | Fogarty |
| 2004/0122516 A1 | 6/2004 | Fogarty |
| 2004/0122526 A1 | 6/2004 | Imran |
| 2004/0167573 A1 | 8/2004 | Williamson, IV et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |
| 2005/0165477 A1 | 7/2005 | Andruiza et al. |
| 2005/0165479 A1 | 7/2005 | Lane |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkaway et al. |
| 2005/0216079 A1 | 9/2005 | MaCoviak |
| 2005/0222674 A1 | 10/2005 | Paine |
| 2005/0234545 A1 | 10/2005 | Nugent et al. |
| 2005/0234546 A1 | 10/2005 | Nuget et al. |
| 2005/0240259 A1 | 10/2005 | Sisken et al. |
| 2005/0240263 A1 | 10/2005 | Fogarty |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004389 A1 | 1/2006 | Nguyen et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |

| | | |
|---|---|---|
| 2006/0085060 A1 | 4/2006 | Campbell |
| 2006/0095125 A1 | 5/2006 | Chinn et al. |
| 2006/0122634 A1 | 6/2006 | Ino |
| 2006/0122692 A1 | 6/2006 | Gilad et al. |
| 2006/0135964 A1 | 6/2006 | Vesely |
| 2006/0136052 A1 | 6/2006 | Vesely |
| 2006/0136054 A1 | 6/2006 | Berg et al. |
| 2006/0149360 A1 | 7/2006 | Schwammenthal et al. |
| 2006/0154230 A1 | 7/2006 | Cunanan |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woofson et al. |
| 2006/0276888 A1 | 12/2006 | Lee |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010835 A1 | 1/2007 | Breton et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0027461 A1 | 2/2007 | Gardiner et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0095698 A1 | 5/2007 | Cambron |
| 2007/0100440 A1 | 5/2007 | Figulla et al. |
| 2007/0106313 A1 | 5/2007 | Golden et al. |
| 2007/0129794 A1 | 6/2007 | Realyvasquez |
| 2007/0142848 A1 | 6/2007 | Ainsworth et al. |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0004696 A1 | 1/2008 | Vesely |
| 2008/0033543 A1 | 2/2008 | Gurskis et al. |
| 2008/0119875 A1 | 5/2008 | Ino et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0112233 A1 | 4/2009 | Xiao |
| 2009/0192599 A1 | 7/2009 | Lane et al. |
| 2009/0192602 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0264903 A1 | 10/2009 | Lee et al. |
| 2009/0319038 A1 | 12/2009 | Gurskis et al. |
| 2010/0044410 A1 | 2/2010 | Argentine et al. |
| 2010/0100174 A1 | 4/2010 | Gurskis |
| 2010/0249894 A1 | 9/2010 | Oba et al. |

FOREIGN PATENT DOCUMENTS

| | | |
|---|---|---|
| DE | 19532973 | 11/1996 |
| EP | 0 084 395 | 8/1986 |
| EP | 0 096 721 | 12/1987 |
| EP | 0 125 393 | 12/1987 |
| EP | 0 179 562 | 7/1989 |
| EP | 0 143 246 | 11/1991 |
| EP | 1057460 | 12/2000 |
| EP | 1 088 529 | 4/2001 |
| EP | 1171059 | 1/2002 |
| EP | 971 650 | 1/2005 |
| EP | 171 059 | 2/2005 |
| GB | 1093599 | 12/1967 |
| GB | 1477643 | 6/1977 |
| GB | 2011259 | 7/1979 |
| GB | 2 056 023 | 3/1981 |
| GB | 2 069 843 | 9/1981 |
| GB | 2254254 | 10/1992 |
| GB | 2 279 134 | 12/1994 |
| SU | 1116573 | 7/1985 |
| WO | 87/05489 | 9/1987 |
| WO | 89/00084 | 2/1989 |
| WO | 91/15167 | 10/1991 |
| WO | 92/01269 | 8/1992 |
| WO | 92/13502 | 8/1992 |
| WO | 92/19184 | 11/1992 |
| WO | 92/19185 | 11/1992 |
| WO | 95/17139 | 6/1995 |
| WO | 95/28899 | 11/1995 |
| WO | 96/40006 | 12/1996 |
| WO | 97/27799 | 1/1997 |
| WO | 97/09933 | 3/1997 |
| WO | 97/09944 | 3/1997 |
| WO | 97/41801 | 11/1997 |
| WO | 97/42871 | 11/1997 |
| WO | 98/06329 | 2/1998 |
| WO | 99/11201 | 3/1999 |
| WO | 99/15112 | 4/1999 |
| WO | 99/51169 | 10/1999 |
| WO | 00/32105 | 6/2000 |
| WO | 00/40176 | 7/2000 |
| WO | 00/44311 | 8/2000 |
| WO | 00/56250 | 9/2000 |
| WO | 00/59382 | 10/2000 |
| WO | 00/60995 | 10/2000 |
| WO | 00/64380 | 11/2000 |
| WO | 01/10310 | 2/2001 |
| WO | 01/10312 | 2/2001 |
| WO | 01/58363 | 8/2001 |
| WO | 01/76510 | 10/2001 |
| WO | 01/82840 | 11/2001 |
| WO | 01/87190 | 11/2001 |
| WO | 2004/006810 | 1/2004 |
| WO | 2004/089246 | 10/2004 |
| WO | 2005/004753 | 1/2005 |
| WO | 2005/020842 | 3/2005 |
| WO | 2005/039452 | 5/2005 |
| WO | 2005/072655 | 8/2005 |
| WO | 2006/086135 | 8/2006 |
| WO | 2009/137517 | 11/2009 |

OTHER PUBLICATIONS

Jansen, et al., "Detachable Shape-Memory Sewing Ring for Heart Valves," Artif. Organs. vol. 16, No. 3, 1992, pp. 294-297, Helmholtz Institute for Biomedical Engineering, Technical University of Aachen, Aachn, Germany.

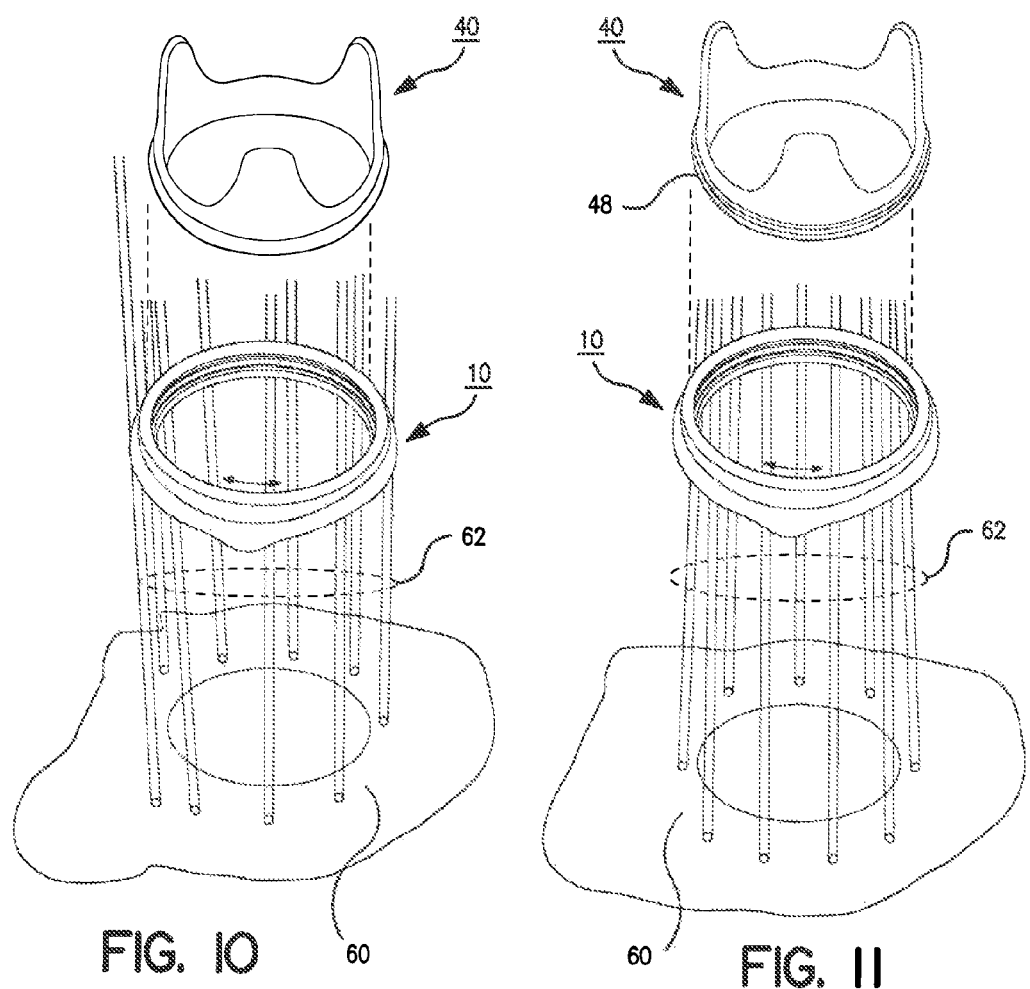

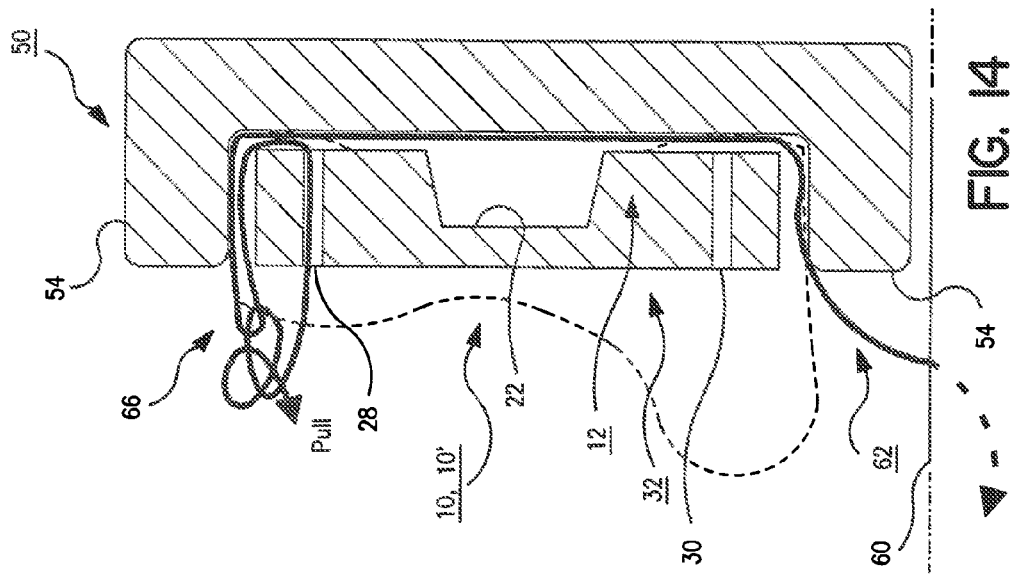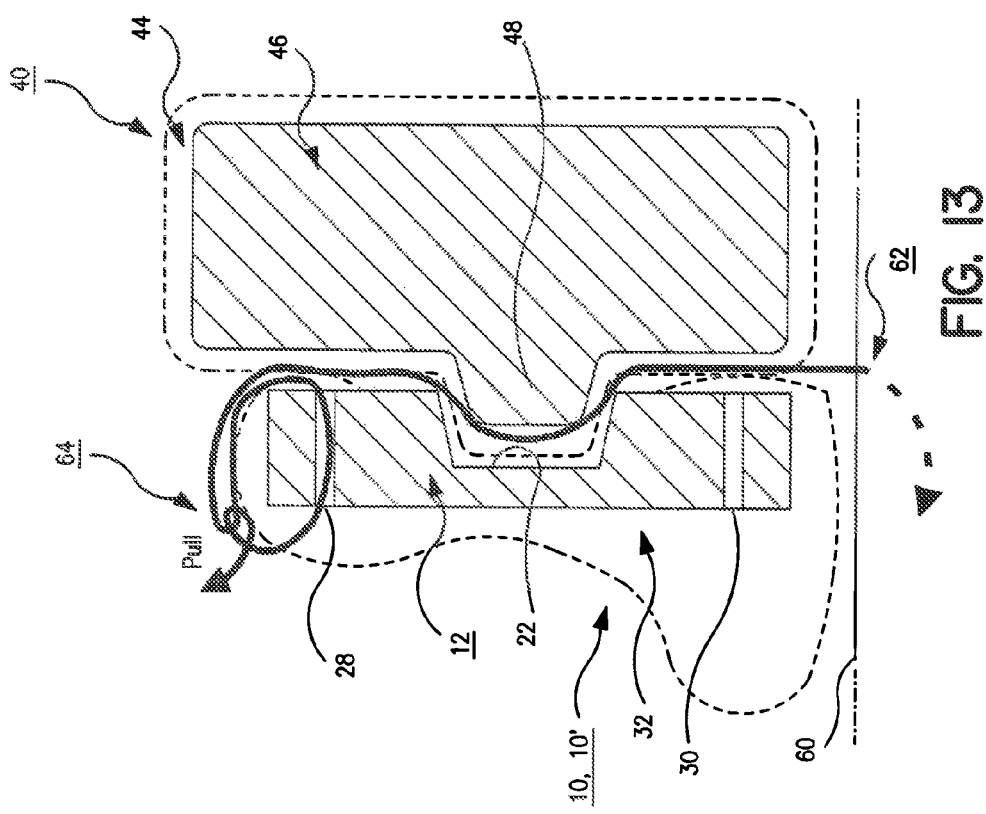

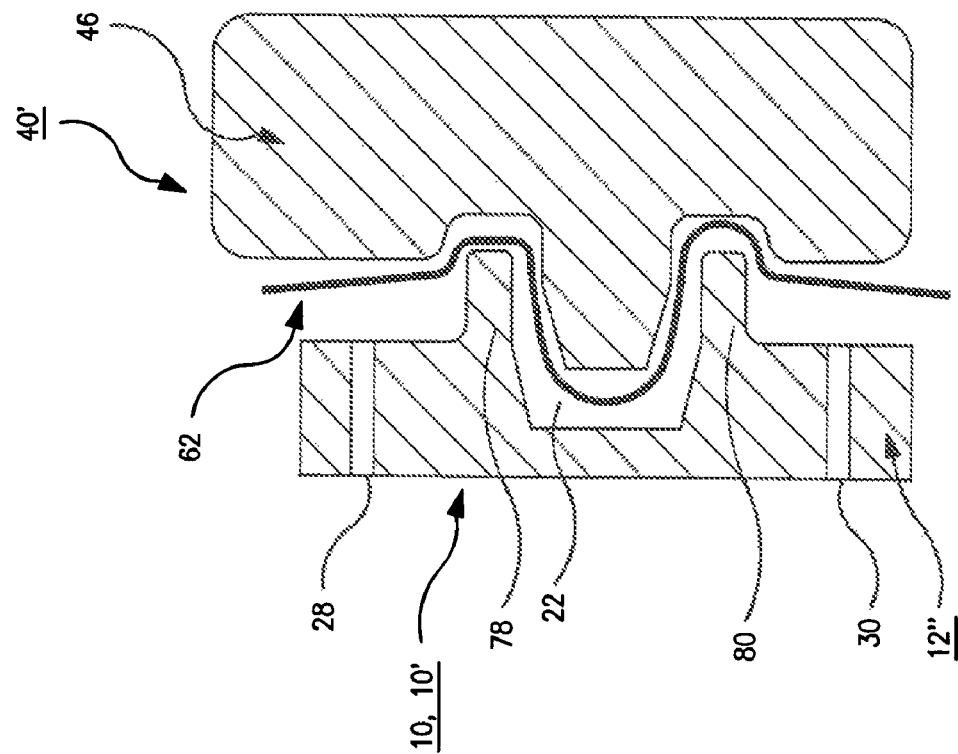
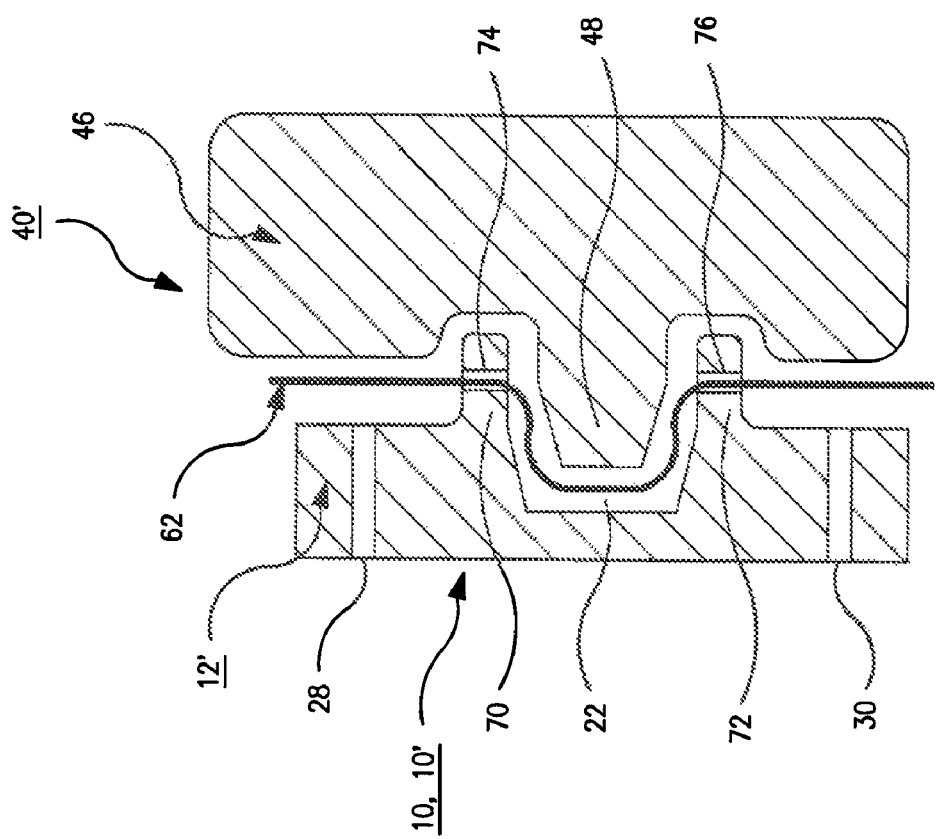

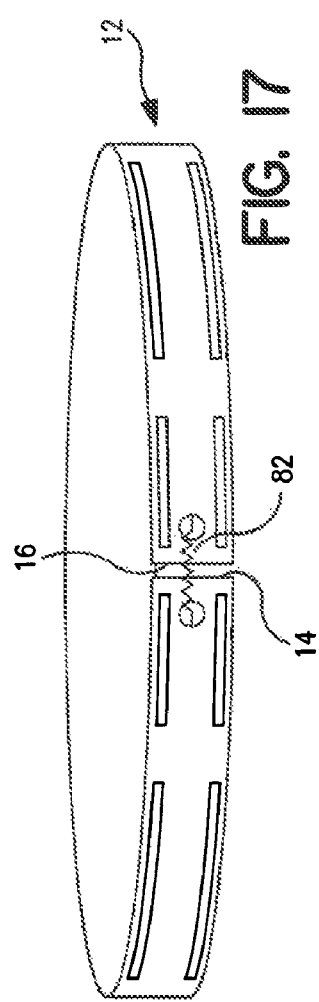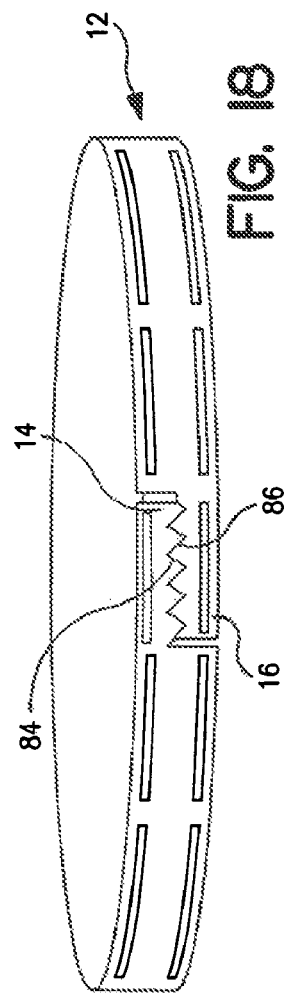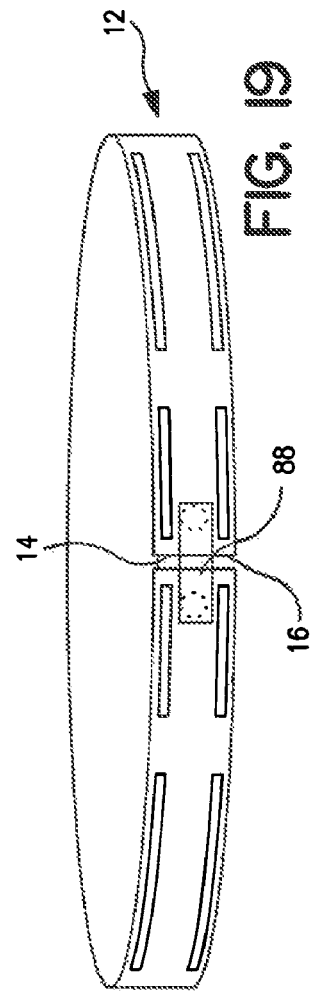

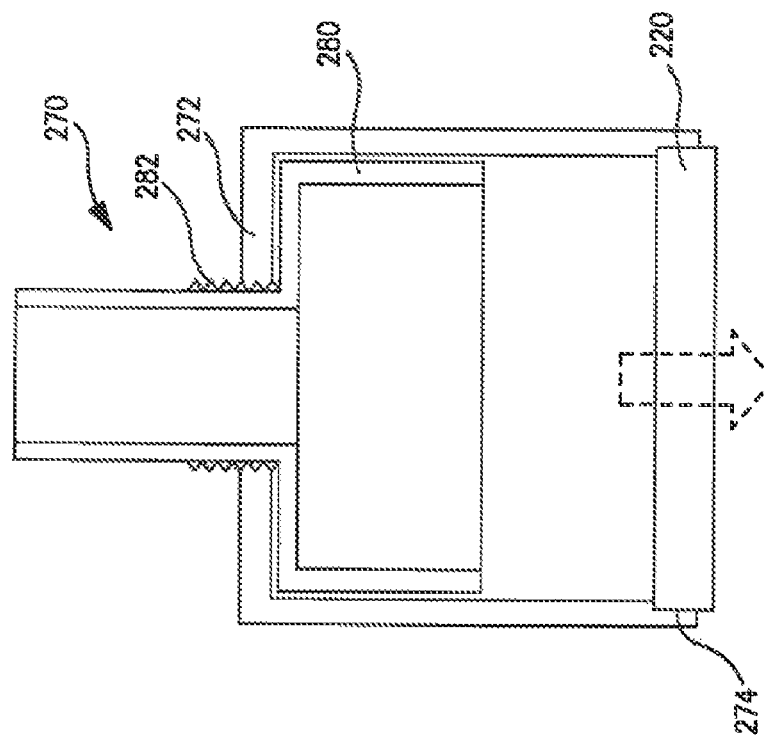
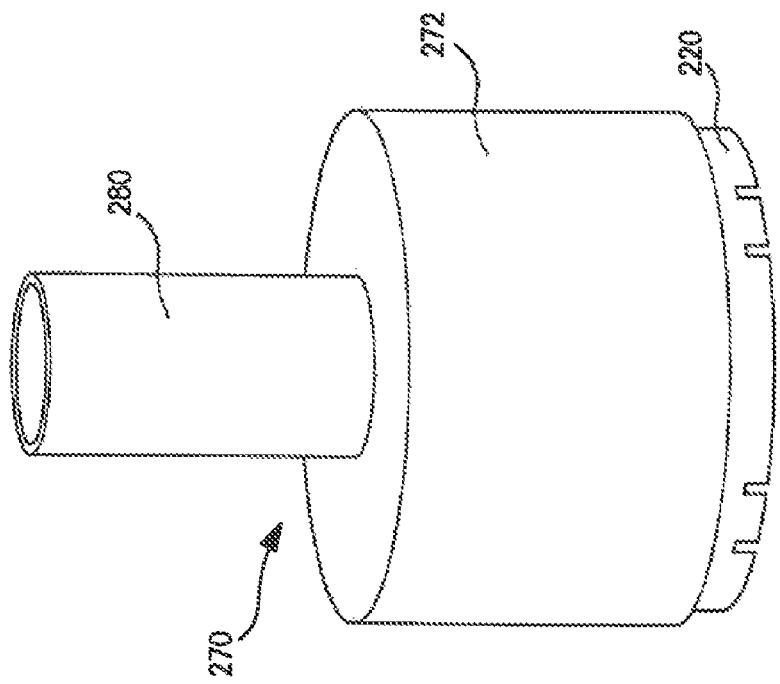
FIG. 29b
FIG. 29a

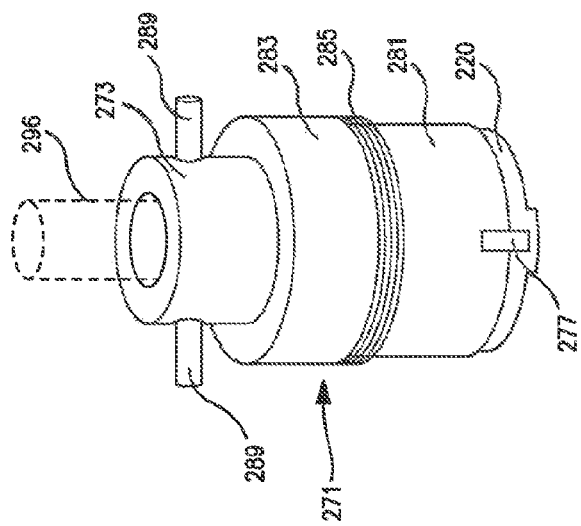
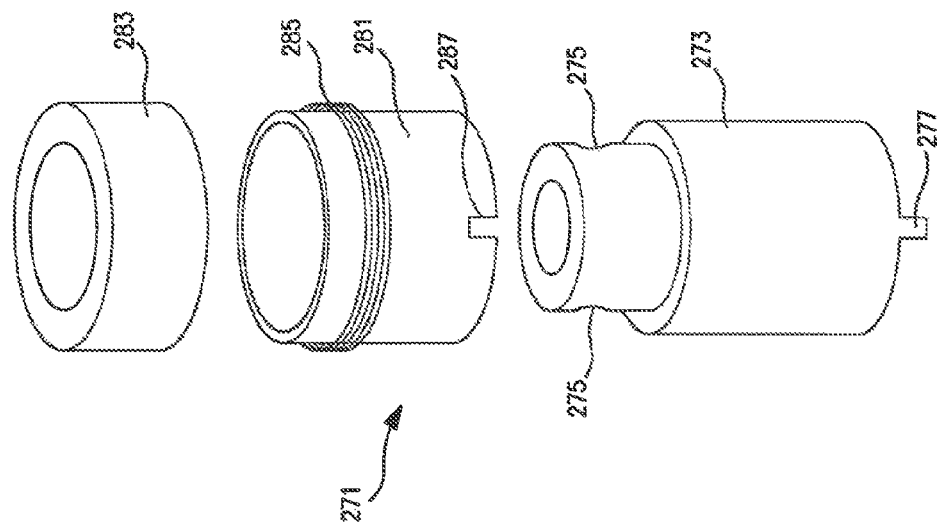

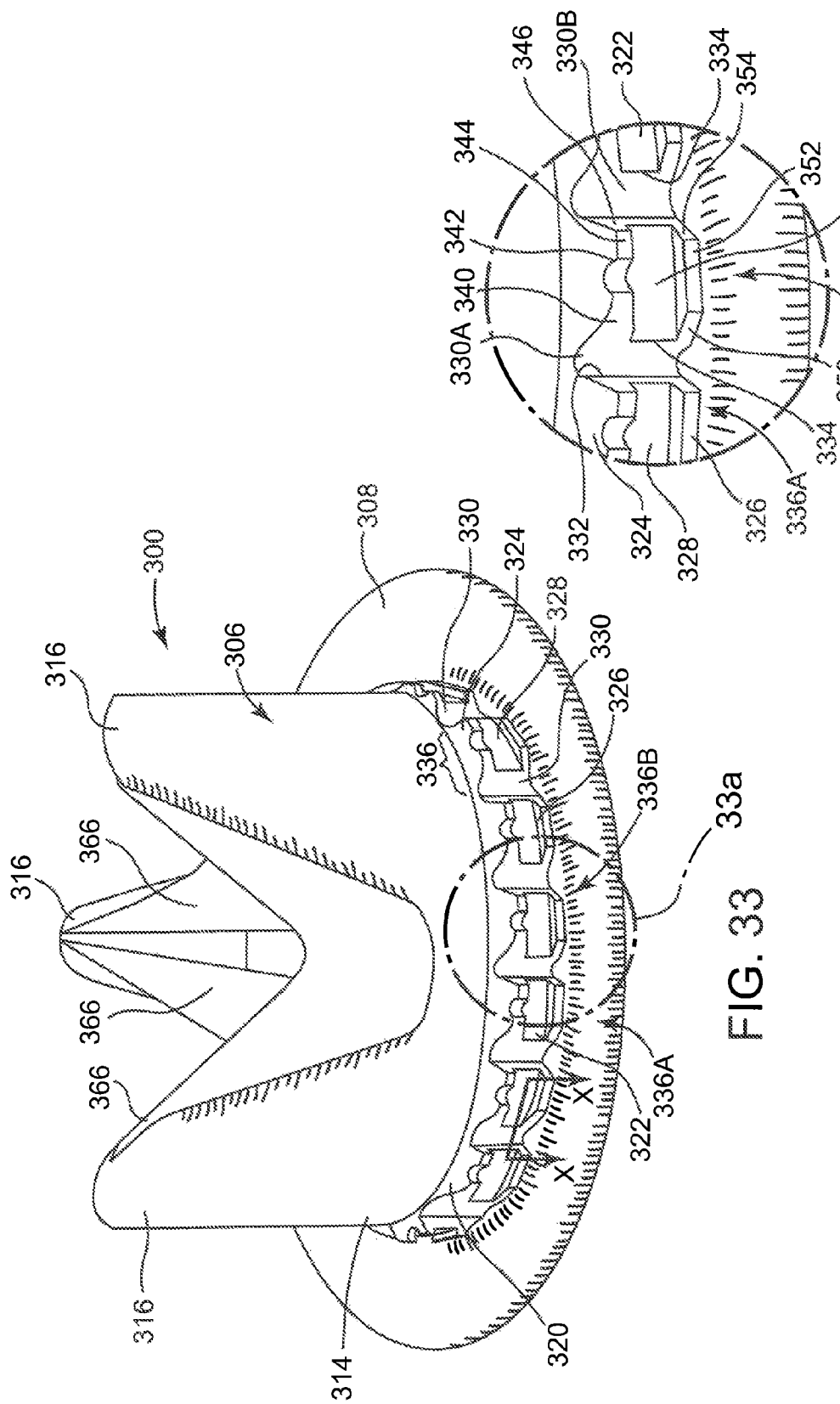

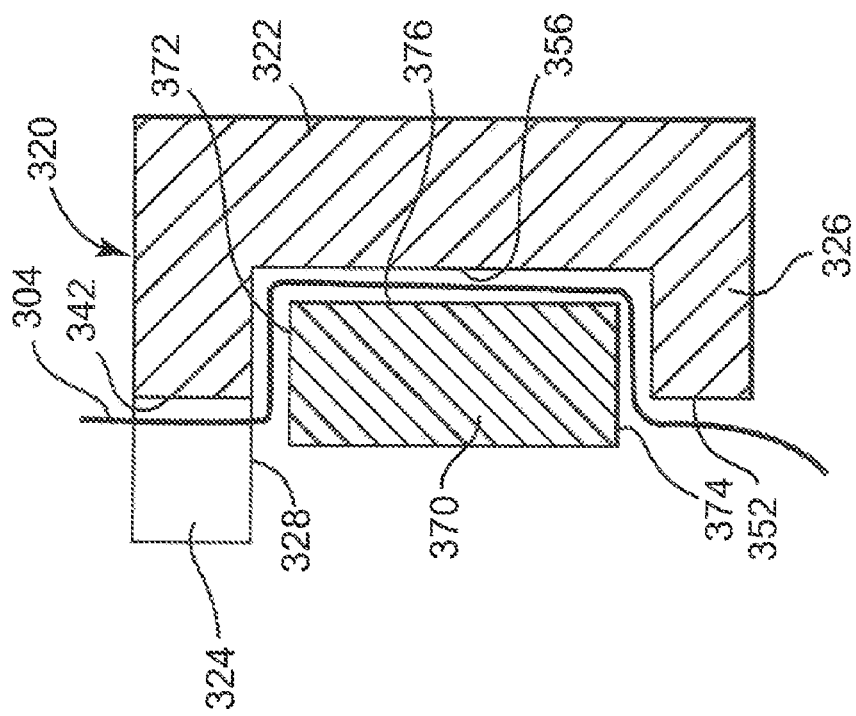
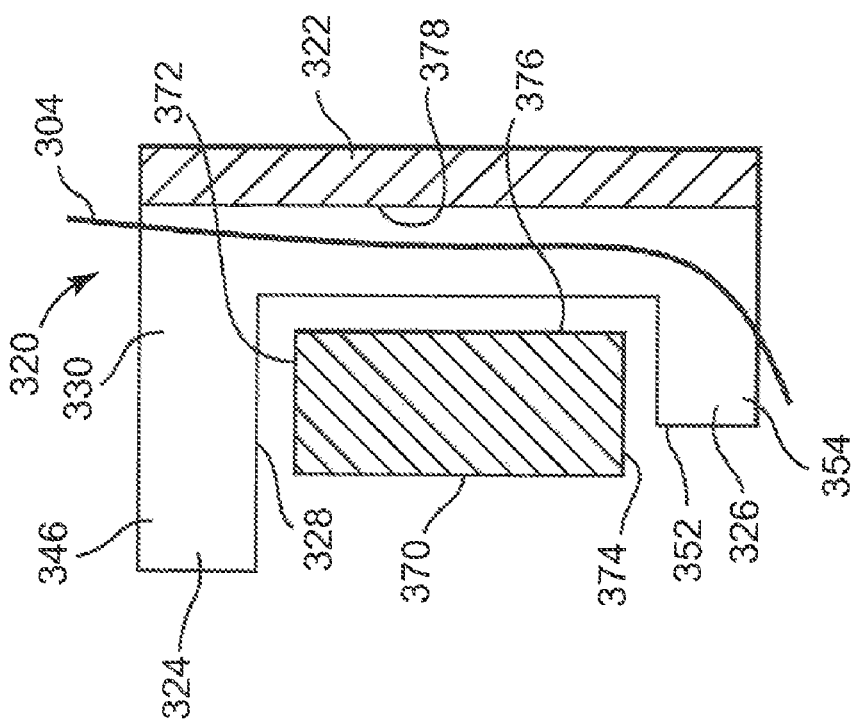

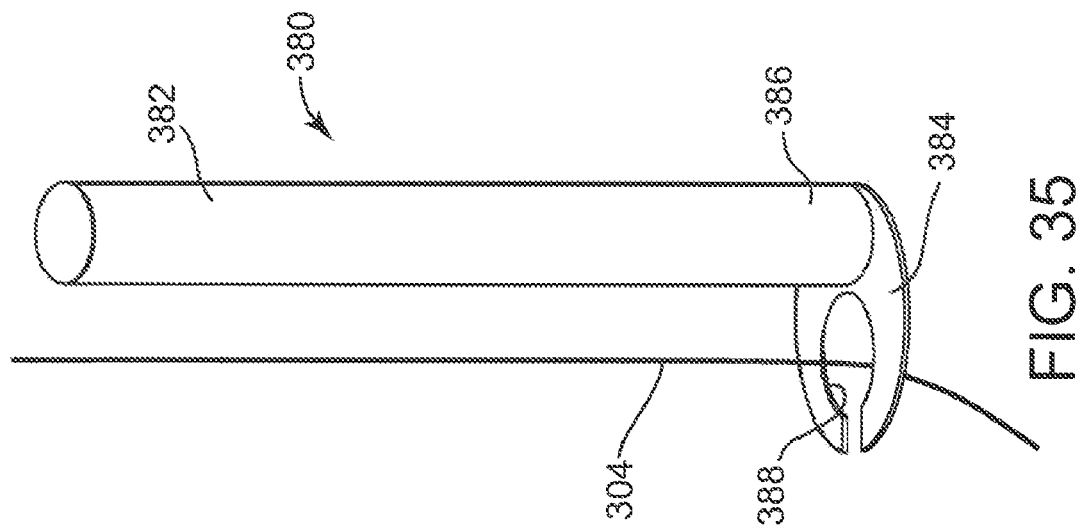

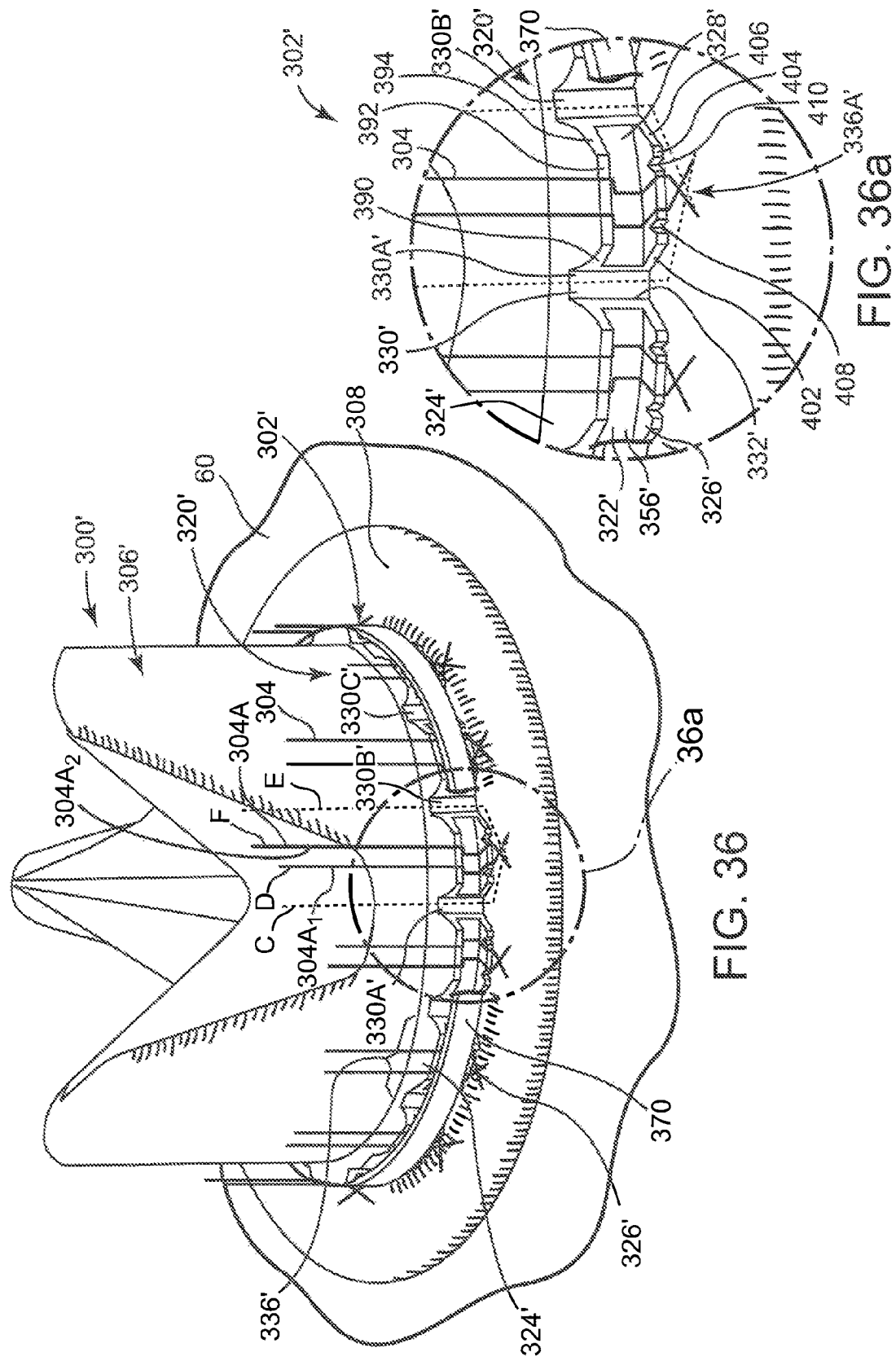

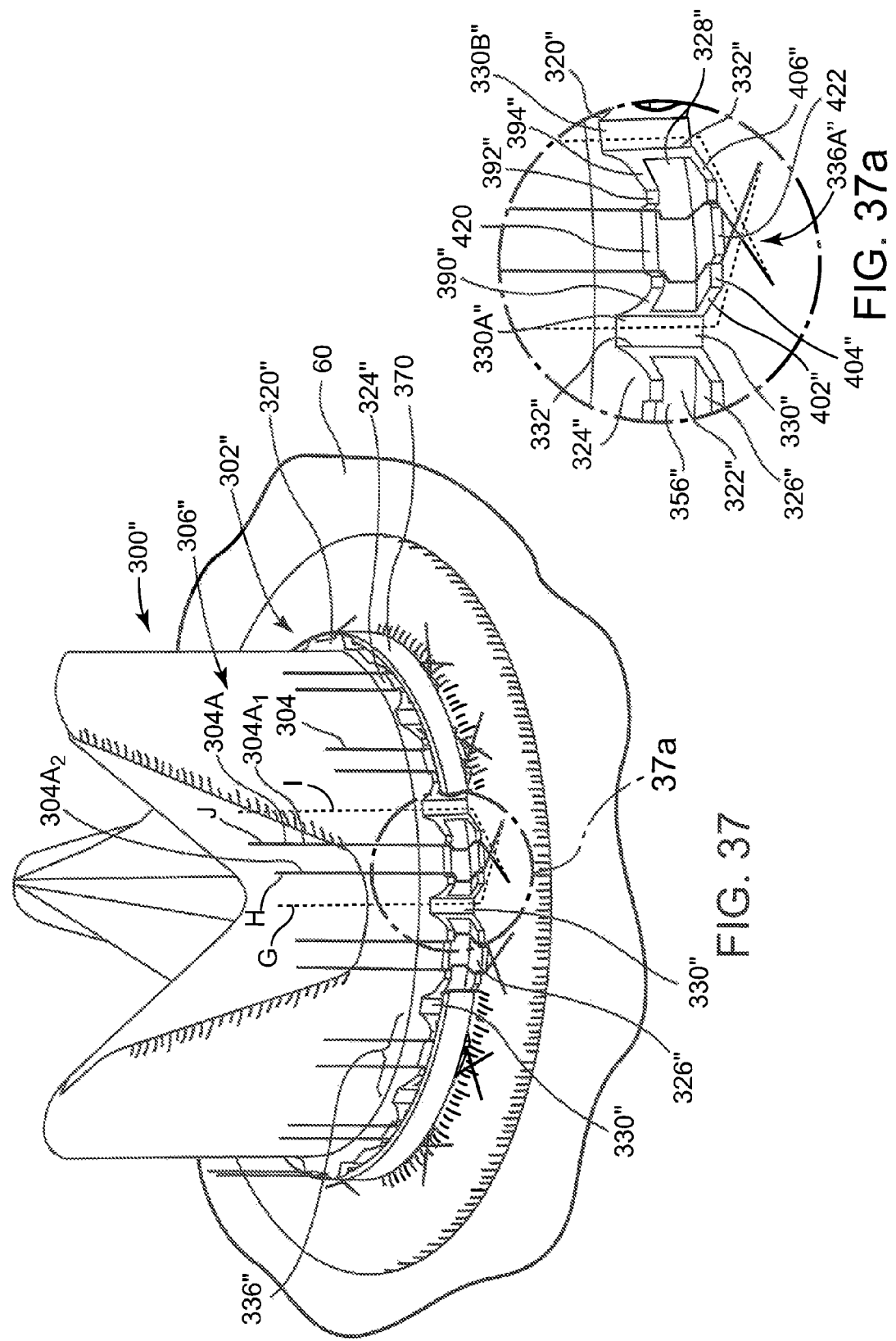

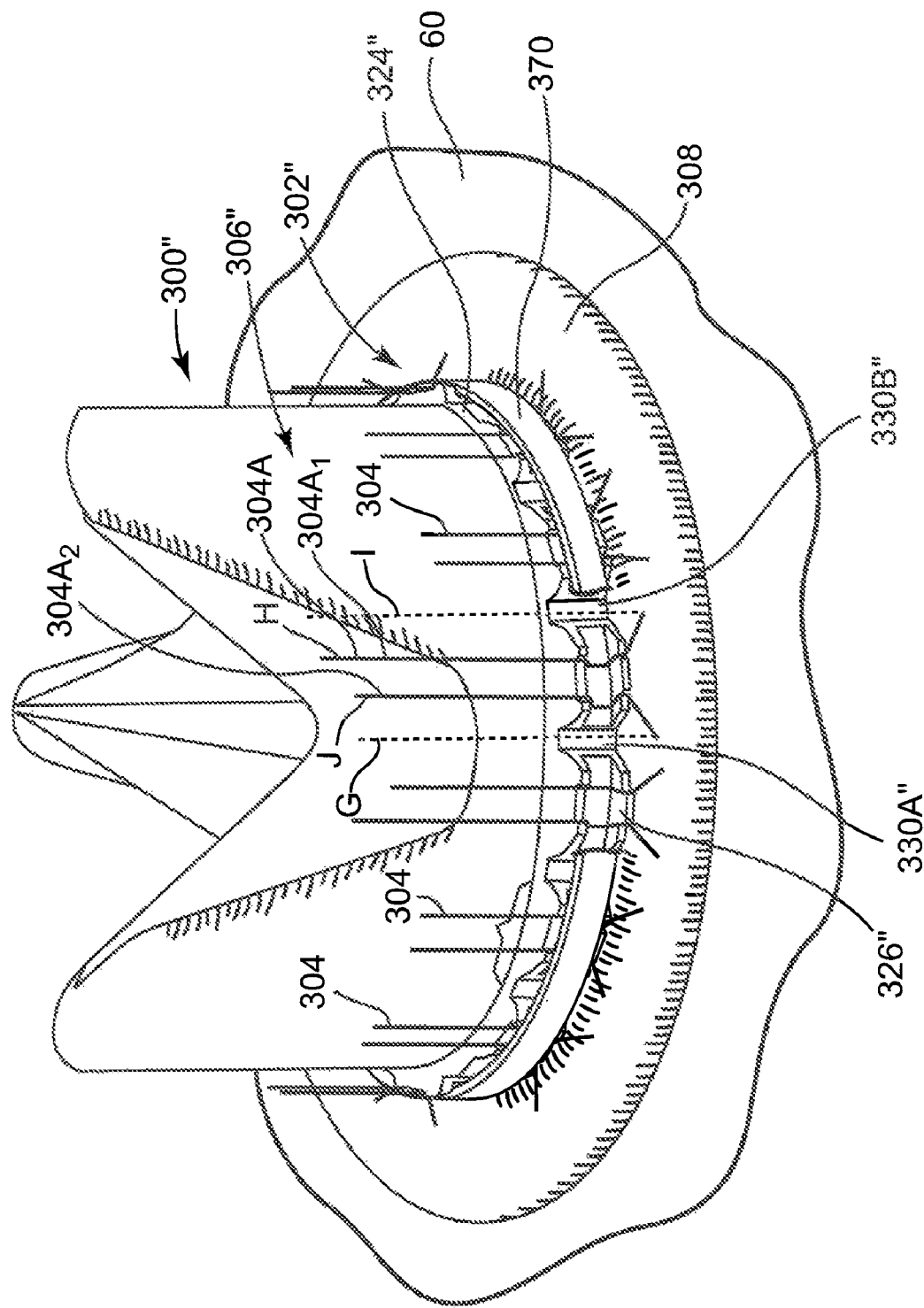

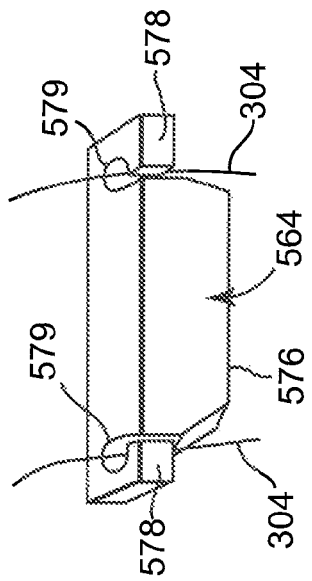
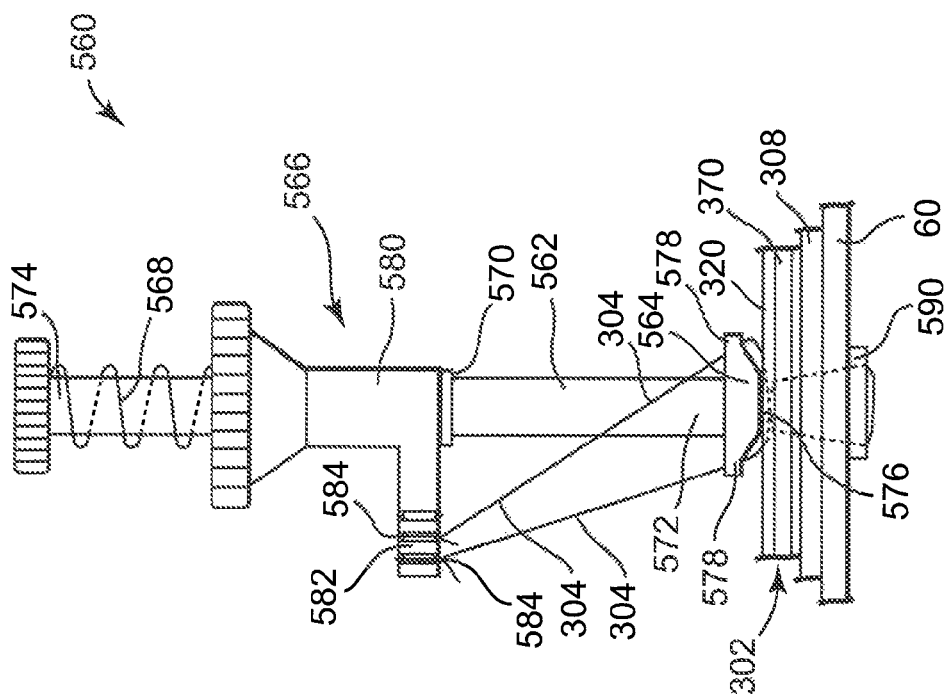

SUTURE LOCKING ASSEMBLY AND METHOD OF USE

CROSS-REFERENCE TO RELATED APPLICATIONS

This application is a divisional of co-pending U.S. patent application Ser. No. 10/792,186, filed Mar. 3, 2004, which is a continuation-in-part of U.S. patent application Ser. No. 10/404,233 filed Apr. 1, 2003 now U.S. Pat. No. 7,578,843, that is a continuation-in-part of U.S. patent application Ser. No. 10/196,527 filed Jul. 16, 2002, now U.S. Pat. No. 7,172,625, both of which are incorporated by reference herein in their entirety

FIELD OF THE INVENTION

The present invention relates generally to a suture locking assembly and method of use in implanting medical devices. More particularly, the present invention relates to a suture locking assembly for a heart valve repair device and related method of use

BACKGROUND

Implantable heart valve prostheses have been used to replace various diseased or damaged natural aortic valves, mitral valves, pulmonic valves and tricuspid valves of the heart. The aortic and mitral valves are most frequently replaced due to heart disease, congenital defects or injury. The mitral valve controls the flow of blood between the left atrium and the left ventricle and the aortic valve controls the blood flow from the left ventricle into the aorta. Generally, the known heart valve prostheses are either bioprostheses or mechanical heart valve prostheses.

The bioprostheses or "tissue valves" are generally made of a suitable animal tissue, e.g., harvested swine valve leaflets, mounted onto a stationary metal or plastic frame, referred to as a "stent." Exemplary tissue valves formed of swine valve leaflets mounted to struts of a stent are those disclosed in U.S. Pat. Nos. 4,680,031, 4,892,541, and 5,032,128 as well as the MEDTRONIC® Hancock II® and Mosaic® stented tissue valves. Some prosthetic tissue valves are formed from treated integral swine valve leaflets and valve annulus structure, e.g. the MEDTRONIC® Freestyle® stentless aortic root bioprostheses.

Modern mechanical heart valve prostheses are typically formed of an annular valve seat in a relatively rigid valve body and one or more occluding disk or pair of leaflets that is movable between a closed, seated position in the annular valve seat and an open position in a prescribed range of motion. Such mechanical heart valves are formed of blood compatible, non-thrombogenic materials, typically currently comprising pyrolytic carbon and titanium. Hinge mechanisms and/or pivoting guides entrap and prescribe the range of motion of the disk or leaflets between open and closed positions. Exemplary bi-leaflet mechanical heart valves are disclosed in commonly assigned U.S. Pat. Nos. 4,935,030 and 6,139,575 and in U.S. Pat. Nos. 6,176,877 and 6,217,611.

Mechanical and tissue valves have advantages and disadvantages. By their very nature, mechanical heart valves have metal or plastic surfaces exposed to the blood flow, which remain thrombogenic even long time after their implantation by major surgery. The opening and closing of mechanical heart valve occluders can damage blood elements and trigger a coagulation. Blood flow disturbances in certain mechanical valves are also believed to aggravate blood coagulation. Therefore, patients having such mechanical heart valves can avoid potentially life threatening embolus formation only by taking anti-thrombogenic or anti-coagulant medication on a regular basis. Porcine tissue valves include three cusps or leaflets of a heart valve excised from pigs and preserved by treatment with glutaraldehyde. The preserved porcine tissue is initially weakly thrombogenic, and therefore, the human patient takes anti-thrombogenic or anti-coagulant medication at least a period of time after the surgical implantation of a tissue valve. Valve leaflet opening and closing characteristics and blood flow past open tissue leaflets of tissue valves can be superior to those afforded by mechanical valves. However, tissue leaflets can become calcified over time distorting the leaflet shape and ultimately leading to failure of the tissue leaflets to fully close or open. Proposals have been advanced to form mechanical heart valve prostheses from flexible, anti-thrombogenic, polymeric sheets or fabrics that are resistant to calcification mounted to stents to function like stented tissue valves also been proposed as exemplified by U.S. Pat. No. 5,562,729. However, calcification and tear issues of polymeric materials remain to be solved before a polymeric valve can be realized.)

Such mechanical and tissue valve prostheses are intended to be sutured to peripheral tissue of a natural heart valve orifice (the "valvular rim") after surgical removal of damaged or diseased natural valve structure. Modern prosthetic heart valves are typically supplied with a sewing or suturing ring surrounding the valve body or stent that is to be sutured by the surgeon to the valvular rim. Suturing rings typically comprise a fabric strip made of synthetic fiber that is biologically inert and does not deteriorate over time in the body, such as polytetrafluoroethylene (PTFE), polyester (e.g., Polyethylene Terephthalate (PET)), or acetyl homopolymer that is woven having interstices permeable to tissue ingrowth. The valve body or stent is typically circular or ring shaped having an outer surface or sidewall shaped to fit with an inner sidewall of the suturing ring. In some cases, the suturing ring fabric is shaped to extend outward to provide a flattened collar or skirt that can be applied against and sutured to the valvular rim, as shown for example in U.S. Pat. No. 3,997,923.

It is proposed in the prior art to make the valve body or stent rotatable within the annulus of the suturing ring. The surgeon can first suture the suturing ring to the valvular rim and then rotate the valve body or stent within the annulus of the suturing ring in order to adjust the angular orientation of the valve mechanism in the path of blood flow. In this way, the valve mechanism can be rotated to minimize interference with the adjacent heart structure or to divert blood flow past the open valve leaflet(s) in an optimal flow direction. Such rotation of the valve mechanism with respect to and within the annulus of the suturing ring requires a rotational torque sufficiently small as to avoid damage to the sutured valvular rim or loosening of the sutures, and yet sufficiently great so that the valve mechanism, when properly positioned, does not further rotate after implantation. Moreover, the configuration and attachment methods should be such as to provide highly reproducible torques so as to maximize productivity in manufacture and minimize scrap and rework. Configurations and methods of attaching suturing rings to annular valve bodies to satisfy these requirements are disclosed in the prior art, e.g., those described in the above-referenced '240 patent and in U.S. Pat. Nos. 5,071,431, 5,397,346, 5,876,436, 6,113,632 for example. However, none of the current available tissue valves allows a surgeon to rotate the stent within the suturing ring because the suturing ring is an integral part of the stent.

Most suturing rings are formed of a radiopaque stiffening ring or band formed of stainless steel, titanium, titanium alloys (e.g. Ti₆Al₄V) and cobalt-based alloys (e.g. Eligiloy®, MP3®, and Stellite®) having an inner annular wall and an outer wall extending between axial ends of the band. The fabric is affixed either to the outer wall of the stiffening band as disclosed, for example, in the above-referenced '632 patent or surrounds the stiffening band as disclosed, for example, in the above-referenced '240 patent. The stiffening band of the '240 is a split band formed with split ends that are drawn against one another during assembly of the suturing ring about the valve stent or body to reduce the inner diameter of the split band in order to overcome difficulties encountered in fabrication employing a continuous ring or band that are described in detail in the '240 patent. The split ends are held together by a cord or heat shrink band or shape memory alloy band that is encased within the fabric when the fabric is sutured together. The interior space within the fabric can be filled with an elastomeric compound.

Separation of the finished suturing ring from the valve body or valve stent to replace the mechanical or tissue valve is not suggested in the '240 patent. Any attempt to do so by cutting the suturing ring assembly apart where the split ends abut one another would effectively destroy the suturing ring. Moreover, it would not be possible to locate the split ends beneath the fabric without disassembling the fabric as well as the cord or band.

Despite improvements in longevity, adverse reactions and complications with implanted mechanical heart valves and tissue valves of the types described above requiring surgical replacement can occur from time-to-time during the lifetime of a patient. It has long been recognized that it is desirable to avoid removing and replacing the suturing ring if it is intact and is not implicated in the adverse reaction or complication. Removal of the existing sutures to remove the suturing ring and re-stitching of a new suture ring in place can compromise the integrity of the valvular rim and lead to further recovery complications, morbidity and mortality. Therefore, attachment and detachment structures and methods have been proposed to enable the removal of the defective mechanical or tissue valve from the suturing ring and insertion of a replacement mechanical or tissue valve into the annulus of the suturing ring sutured to the valvular rim.

In one approach disclosed in the above-referenced '128 patent, the valve stent is sutured to the suturing ring upon initial implantation. Replacement of the tissue valve involves severing the sutures by a scalpel worked between the suturing ring annulus, withdrawing the released tissue valve, inserting a new tissue valve into the ring annulus and suturing it in place. This approach requires a valve design that can be stitched in place in the suturing ring annulus, does not allow the tissue valve to be easily rotated in the suturing ring in the manner described above, and requires considerable care and time to execute. Pannus overgrowth and calcification of the surfaces at the junction between the valve stem and the suturing ring occur over time that must be cut away or through without damaging the suturing ring. Consequently, other approaches have been devised allowing rotation of the replacement tissue or mechanical valve within the suturing ring annulus.

A detachable suturing ring having a shape-memory member that expands in diameter when cooled below blood temperature to allow release and replacement of a valve body or stent is disclosed by J. Jansen et al. in "Detachable Shape-Memory Sewing Ring for Heart Valves", (*Artificial Organs*, vol. 16, No. 3, pp. 294-7, 1992). While this approach would appear to be very beneficial, it has not been established that the temperature induced shape changes are robust enough to assure retention of the tissue or mechanical valve or large enough when cooled by cooling fluid to expand a chronically implanted suturing ring to allow removal of a valve body or stent. Pannus overgrowth and calcification about the suturing ring would likely reduce the amount of expansion or prevent any appreciable expansion of the ring when it is cooled in the attempt to expand it. Moreover, this concept is impractical because of high cost and difficulty in fabrication.

More typically, it has been proposed to use an interlocking mechanism of the suturing ring and the valve body or stent that can be operated by the surgeon to detach or attach valve body or stent from or to the suturing ring. Mating male and female screw threads, snaps, fabric hooks, screws, or other interlocking mechanisms are disclosed in the above-referenced '031 patent, '923 patent, '541 patent, and in U.S. Pat. Nos. 3,997,923, 4,078,268, 4,506,394, 4,705,516, 4,790,843, 6,217,611 and Re.31,040, for example.

These interlocking mechanisms necessarily must be robust enough to ensure that they do not fail during chronic implantation thereby loosening or releasing the tissue or mechanical valve and endangering the life of the patient. The interlocking mechanisms must be large enough to be readily manipulated and to not become frozen due to coagulation or exposure to blood and fluids. On the other hand, the interlocking mechanism must be minute in size in order to avoid taking up space that would reduce the size of the valve annulus or interfere with leaflet function. Consequently, none of these proposed interlocking mechanisms have been widely adopted or are in use today.

In the following description and claims, the term "heart valve mechanism" embraces a tissue valve mechanism comprising a stent supporting tissue leaflet(s) and a mechanical heart valve mechanism comprising a heart valve body supporting a pivotal disk or leaflet(s). For convenience, the term "valve frame" means a stent of a tissue valve or a valve body of a mechanical heart valve or equivalents thereof, and the term "occluder" means tissue leaflets of a tissue valve or pivotal disk or leaflets of a mechanical heart valve or equivalents thereof. The assembly of a tissue or a mechanical heart valve mechanism with a suturing ring can be characterized as a heart valve prosthesis.

Thus, there remains a need for improvements in suturing rings that facilitate the initial implantation and replacement of chronically implanted heart valve mechanisms supported by the suturing rings. Among other things, there remains a need for a system and method of implanting medical devices such as heart valve prostheses and annuloplasty rings that reduces the time of implantation thereby increasing patient well-being and outlook.

SUMMARY

One aspect of the present invention relates to a suture locking assembly for use with a heart valve repair device. The suture locking assembly includes a rim and a suture band. The rim defines a first flange and a second flange spaced from the first flange. The rim is configured to extend at least partially around a periphery of the heart valve repair device. The suture band is maintained between the first flange and the second flange. The suture locking assembly is configured to securely maintain a suture segment that is pulled from a first position to a second position relative the suture locking assembly, the second position being at least partially defined near an outer periphery of the rim.

BRIEF DESCRIPTION OF THE DRAWINGS

These and other features and advantages of the invention will become apparent to those skilled in the art from the following detailed description of a preferred embodiment, especially when considered in conjunction with the accompanying drawings in which:

FIG. 10 is an illustration of one method of securing the suturing ring to the valvular rim employing sutures through the suturing ring fabric;

FIG. 11 is an illustration of a further method of securing the suturing ring to the valvular rim employing sutures extending inside the suturing ring annulus in accordance with the second aspect of the invention;

FIG. 13 is a cross-section view taken along lines 13-13 of FIG. 12 illustrating the entrapment of a suture between the inner wall of the suturing ring and the outer wall of the stent;

FIG. 14 is a further cross-section view taken along lines 9-9 of FIG. 7 illustrating the entrapment of a suture between the inner wall of the suturing ring and the outer wall of the valve body of a mechanical heart valve;

FIG. 15 is a further cross-section view taken along lines 13-13 of FIG. 12 illustrating alternative configurations of the inner wall of the split stiffening band and the outer wall of the stent facilitating the entrapment of a suture between the inner wall of the suturing ring and the outer wall of the stent;

FIG. 16 is a still further cross-section view taken along lines 13-13 of FIG. 12 illustrating alternative configurations of the inner wall of the split stiffening band and the outer wall of the stent facilitating the entrapment of a suture between the inner wall of the suturing ring and the outer wall of the stent;

FIGS. 17-19 are plan schematic views of the split stiffening band illustrating an alternative or additional restraint mechanism for closing and opening the split stiffening band;

FIG. 26a is a perspective view of the band shown in FIG. 25a.

FIG. 26d is a partial perspective view of yet another embodiment of a band similar to that shown in FIG. 26a.

FIG. 28a is a cross sectional view of the engaged band taken at the cross section of FIG. 26b with the frame portion of FIG. 25a.

FIG. 28b is a cross sectional view of the engaged band taken at the cross section of FIG. 26c with the frame portion of FIG. 25a.

FIG. 29a is a perspective view of the band of FIG. 25a engaged with a band applicator tool for applying it to a frame portion as in FIG. 25a-b.

FIG. 29b is a cross sectional view of the band applicator tool and band of FIG. 29a.

FIG. 29c is an exploded perspective view of an alternative band applicator tool.

FIG. 29d is a perspective view of the applicator tool of FIG. 29c engaged with a band

FIG. 30b is a perspective view of the suture tensioning tool of FIG. 30a.

FIG. 31 is a perspective view of the valve and valve holder tool of FIG. 30a with the band and band applicator tool of FIG. 29a.

FIG. 33 is a perspective view of one embodiment of the heart valve mechanism with a flange of the suture locking assembly of FIG. 32.

FIG. 33a is a detail view of the heart valve mechanism with flange of FIG. 33.

FIG. 34a is a cross-sectional view of the suture locking assembly of FIG. 32 taken along the line 34A-34A with a suture in a first position "A".

FIG. 34b is a cross-sectional view of the suture locking assembly of FIG. 32 taken along the line 34B-34B with a suture in a second position "B".

FIG. 35 is a perspective view of one embodiment of a suture holder for use with the suture locking assembly of FIG. 32.

FIG. 36 is a perspective view of another embodiment of a heart valve mechanism with a suture locking assembly according to the present invention.

FIG. 36a is a detail view of the heart valve mechanism with the suture locking assembly of FIG. 36.

FIG. 37 is a perspective view of another embodiment of a heart valve mechanism with a suture locking assembly according to the present invention.

FIG. 37a is a detail view of the heart valve mechanism with the suture locking assembly of FIG. 37.

FIG. 37b is a perspective view of the heart valve mechanism with the suture locking assembly of FIG. 37 illustrating one embodiment of a suture technique.

FIG. 43 is a side view of one embodiment of a suture holder for use with a suture locking assembly in a first position.

FIG. 43a is a detailed perspective view of a holder support of the suture holder of FIG. 43.

DETAILED DESCRIPTION

The present invention can be implemented to improve implantation procedures and performance of a wide variety of heart valve prostheses of the various types currently existing or that may come into existence that are surgically attached to a prepared valvular rim. As noted above, the present invention involves improved suturing rings that support removable heart valve mechanisms, e.g., tissue or polymer valves and mechanical heart valves comprising a heart valve frame and occluder. The valve frames described in the exemplary embodiments are a tissue valve stent or a mechanical valve body, and the occluders include tissue leaflets of a tissue valve or pivotal disk or leaflets of a mechanical heart valve. The various aspects of the present invention may be utilized in attaching any such valve frame or any other valve frames that are devised in the future to a suturing ring.

Figure 1:
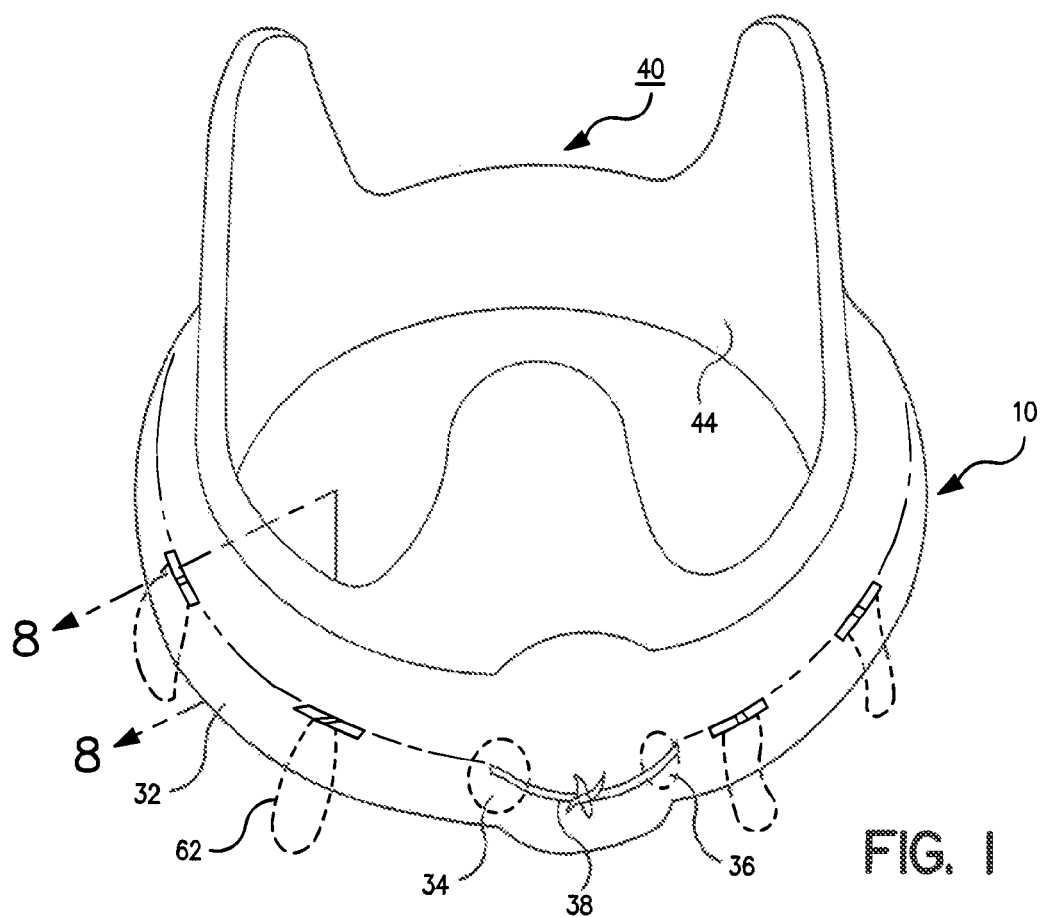
FIG. 1 is a perspective view of the assembly of a suturing ring and stent of a tissue valve formed in accordance with the present invention.
Figure 2:
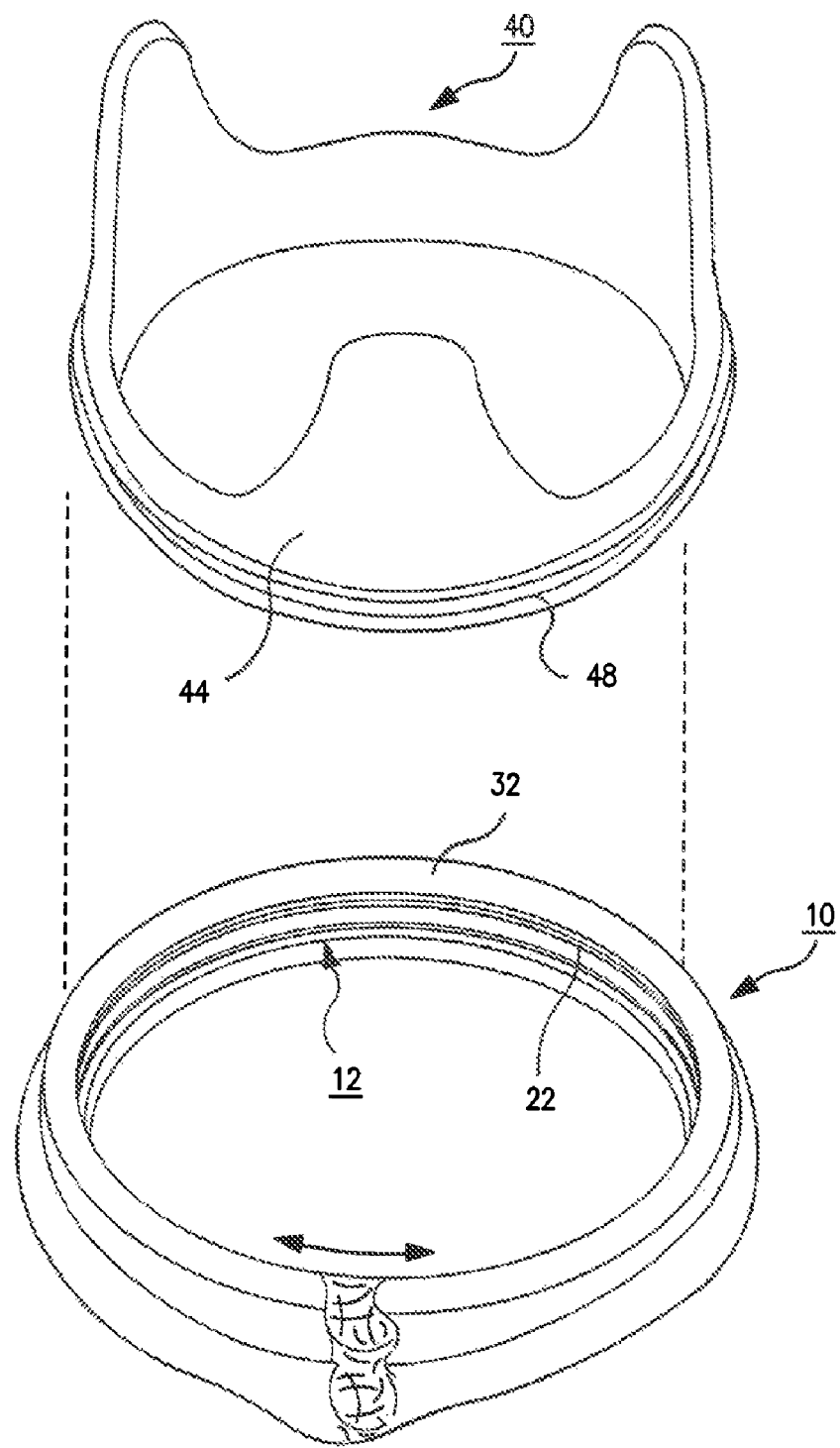
FIG. 2 is a perspective view of the stent of FIG. 1 arranged to be inserted into the annulus of the suturing ring of FIG. 1.
Figure 3:
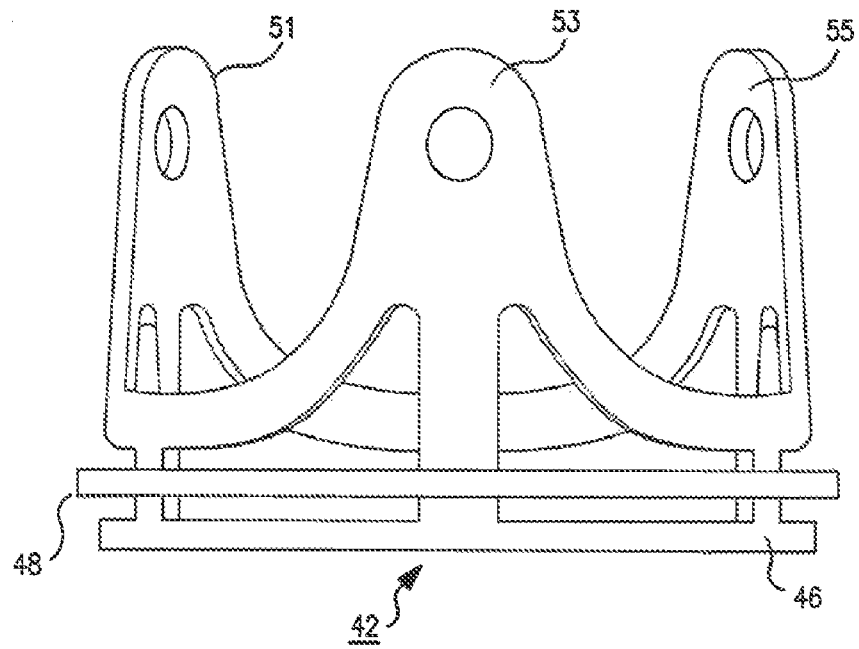
FIG. 3 is a side elevation view of the stent frame of the stent of FIG. 2.
Figure 6:
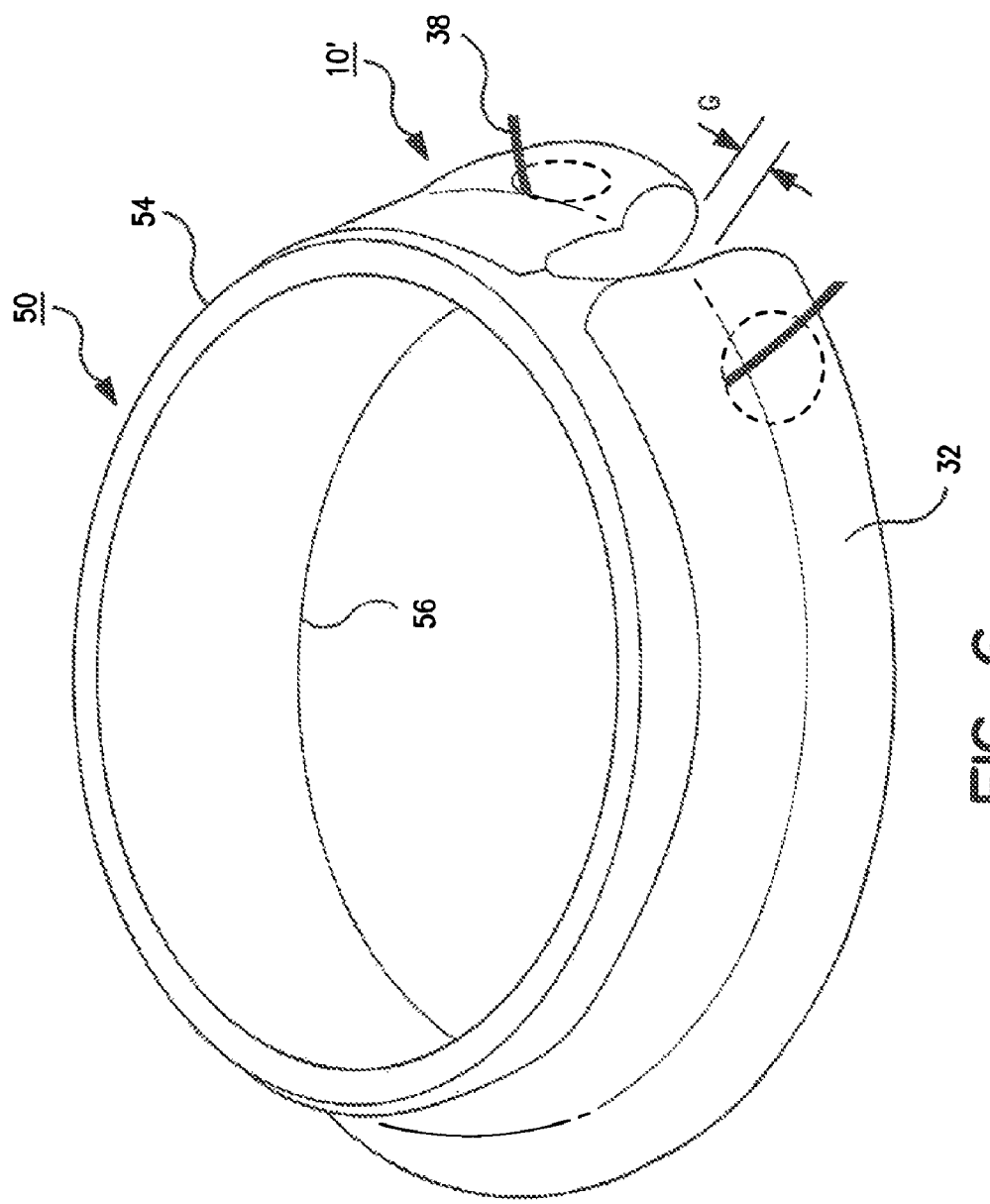
FIG. 6 is a perspective view of the released assembly of a further embodiment of the suturing ring of FIGS. 1 and 2 and a valve body of a mechanical valve formed in accordance with the present invention.
Figure 7:
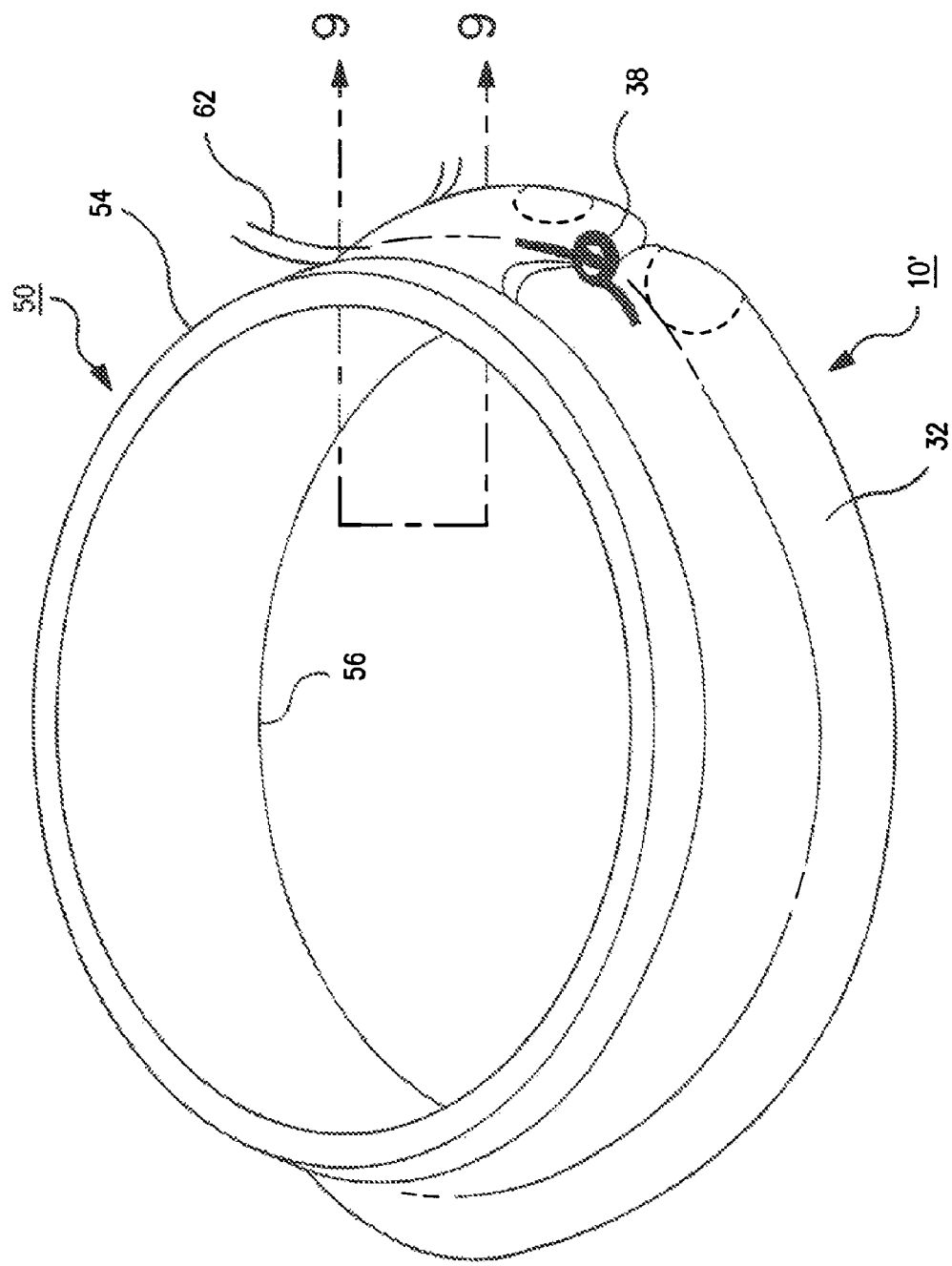
FIG. 7 is a perspective view of the tightened assembly of the suturing ring of FIG. 6 about the outer wall of the valve body of the mechanical valve of FIG. 6.

Thus, for example, FIGS. 1-3 depict a suturing ring 10 that is employed to support a fabric covered stent 40 of a tissue valve mechanism, and FIGS. 6 and 7 depict a suturing ring 10' that is employed to support a valve body 50 of a mechanical heart valve mechanism. The tissue leaflets supported by stent 40 are not show in the figures for convenience of illustrating the aspects and embodiments of the present invention. The stent 40 and tissue leaflets can take any of the forms known in the art such as those described in the background of the invention. Similarly, the pivotal disk or leaflet(s) and the valve seat and the hinging mechanisms of the valve body 50 enabling and controlling movement of the pivotal disk or leaflets may take any of the forms known in the art and are not shown in any of the figures for convenience of illustrating the aspects and embodiments of the invention.

Figure 5:
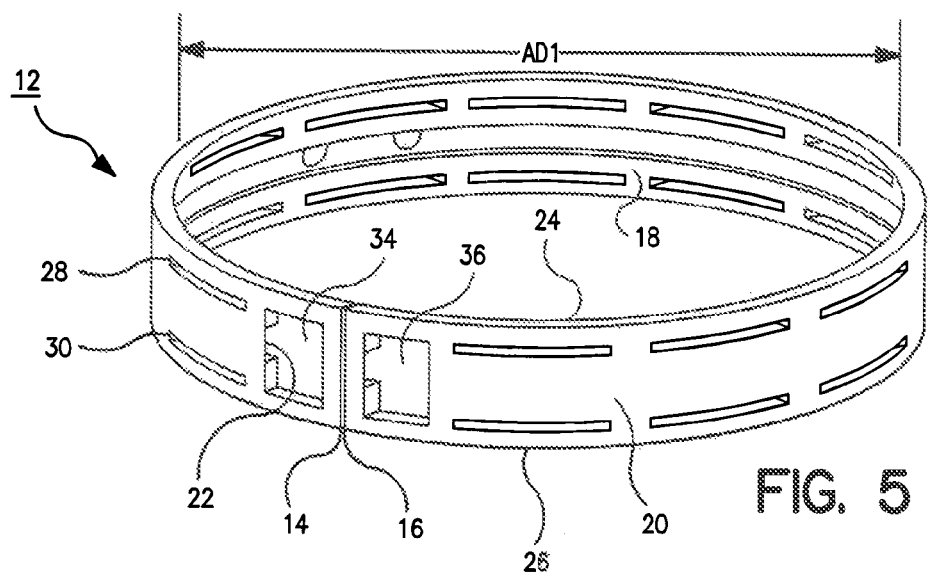
FIG. 5 is a perspective view of the split stiffening band enclosed within the suturing ring of FIGS. 1 and 2.
Figure 4:
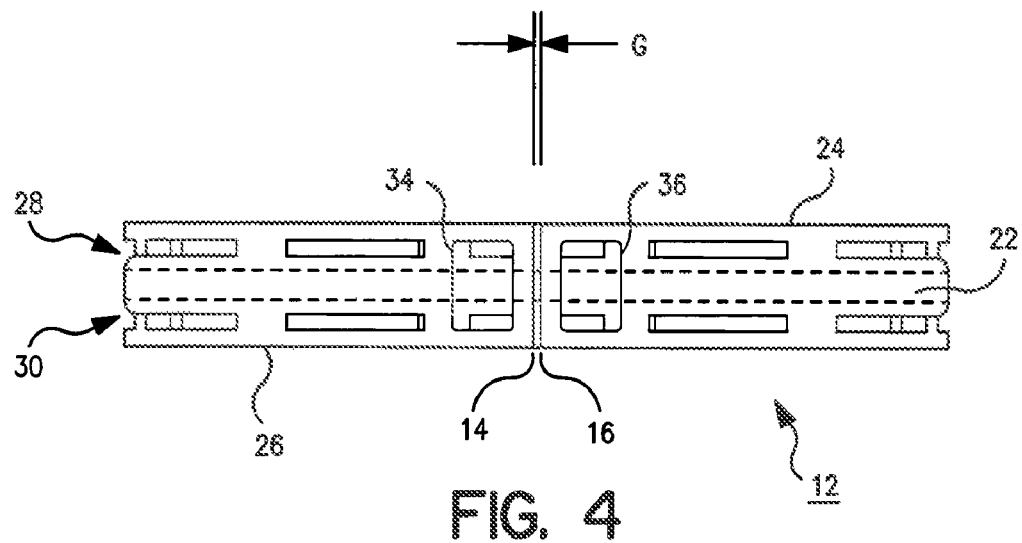
FIG. 4 is a side elevation view of the split stiffening band enclosed within the suturing ring of FIGS. 1 and 2.

In the first aspect of the present invention, the suturing rings 10 and 10' are formed of a generally annular, split stiffening band 12 depicted in FIGS. 2, 4 and 5 extending longitudinally between opposed band split ends 14 and 16 and that supports a stent fabric 32. The split stiffening band 12 can be formed of a biocompatible metal, e.g., titanium or tantalum, a plastic material, e.g., acetyl homopolymer plastic, reinforced pyrolytic carbon or of other material. The split stiffening band 12 has an interior band sidewall 18 formed with an outwardly extending annular groove 22 that engages the stent 40 as described further below and an exterior band sidewall 20 that is generally flat but may have any shape. The inner and exterior band sidewalls 18 and 20 are joined at the opposed band split ends 14 and 16 and at the upper and lower axial ends 24 and 26. A plurality of upper and lower suture receiving slots 28 and 30 extend through the inner and exterior band sidewalls 18 and 20 so that the suturing ring fabric 32 can be sutured to the split stiffening band 12.

The suturing ring fabric 32 comprises a fabric strip made of synthetic fiber, such as polytetrafluoroethylene (PTFE), polyester (e.g., Polyethylene Terephthalate (PET)), or acetyl homopolymer of a mesh weave having interstices permeable to tissue ingrowth. The longitudinal edges of the fabric strip are sewn together to form longitudinal seams. One longitudinal seam is wrapped over the upper axial end 24, fitted against the interior band sidewall 18 over the set of upper slots 28, and the fabric strip is sewn together through the set of upper slots 28. The other longitudinal seam is wrapped over the lower axial end 26, fitted against the interior band sidewall 18 over the set of lower slots 30, and the fabric strip is sewn together through the set of lower slots 30. The ends of the fabric strip are sewn together over the gap G (FIG. 4) separating the opposed band split ends 14 and 16 in the suturing ring 10 or left separated at the opposed band split ends 14 and 16 in the suturing ring 10'. In this way, groove 22 remains exposed, and the fabric strip is thereby formed into a torus shaped or annular shaped suturing ring fabric 32. The shape of the suturing ring fabric 32 may be relatively flat if the suturing ring is intended to be used in aortic valve replacement as shown in the above-referenced '575 patent. Suturing rings for heart valves intended for mitral valve replacement have pronounced radially extending flanges or skirts or collars formed of a wider fabric strip that is sewn or filled as shown, for example, in the above-referenced '030 and '346 patents, respectively. The suturing ring fabric 32 may also be filled with a biologically acceptable, spongy material, such as silicone rubber, polyurethane, hydrogel, silicone, polytetrafluorethylene (PTFE) felt, or Polyethylene Terephalate (PET) felt and the filled suturing ring fabric 32 may be formed and shaped as desired. However, the resulting suturing ring fabric 32 may have any desired cross-section profile.

As shown in FIG. 4, the band split ends 14 and 16 are separated apart by a gap G such that a first annulus diameter AD1 of the annulus of the suturing ring 10 is defined when the suturing ring 10 is unrestrained. The split stiffening band 12 is resilient, and the split stiffening ends 14 and 16 can be separated apart to widen gap G and increase the first annulus diameter AD1 to a second annulus diameter AD2 that accommodates a somewhat larger diameter valve frame or brought together to decrease gap G and the first annulus diameter AD1 to the second annulus diameter AD2 to accommodate a somewhat smaller diameter valve frame.

The suturing ring 10 is adapted to be surgically attached, as by suturing, to a prepared aortic or mitral valvular rim of a patient's heart with the suturing ring 10 unrestrained as described further below. The suturing ring first annulus diameter AD1 is sized with respect to the selected heart valve frame diameter to enable a valve body 50 of a mechanical heart valve or a stent 40 of a tissue valve to be inserted into the suturing ring annulus and rotated therein to a desired orientation. Then, the suturing ring split ends 14 and 16 are secured or restrained by an interlocking or restraining mechanism of one of the types described herein and equivalents thereto. The restraint is preferably accomplished by one or more of sutures, clamps, hooks, teeth, buttons, or other ring locking mechanisms that can released even after chronic implantation so that the heart valve mechanism can be replaced.

A preferred interlocking restraint comprises the use of one or more suture 38 sewn through the fabric 32 overlying and through a suitable suture retainer, e.g., the illustrated suture holes 34 and 36 extending through the stiffening band 12, adjacent the band split ends 14 and 16, respectively. The suture 38 is pulled tight to draw the band split ends 14 and 16 together to the extent permitted by the valve frame, and tied off. Thus, the stiffening band split ends 14 and 16 can be restrained such that the second annular diameter AD2 of the suturing ring 12 is defined, and the suturing ring 12 interference fits with and engages the valve frame exterior surface. In the following examples, it will be assumed that the second annulus diameter AD2 is smaller than the first annulus diameter AD1.

Preferably, the interior surface 18 of the split stiffening band 12 is shaped in a complimentary mating fashion to the exterior surface of the valve frame to entrap or lock the surfaces together when the band split ends 14 and 16 are restrained. For example, it will be assumed that the complimentary mating shapes can comprise one or more spiral or annular groove or array of groove segments or pin holes extending into the outer surface of the valve frame or into the inner surface 18 of the split stiffening band 12 that receives a mating one or more spiral or annular flange or array of flange segments or pins projecting outward from the other of the inner surface 18 of the split stiffening band 12 or the outer surface of the valve frame.

In the depicted tissue valve embodiments, the valve stent 40 comprises a wire or plastic or reinforced pyrolytic carbon stent frame 42 covered with stent fabric 44 of the same materials as the suturing ring fabric 32. The stent frame 42 shown in FIG. 3 can take any of the known configurations having a cylindrical frame base 46 and a plurality of frame posts 51, 53, and 55. An annular flange 48 is formed extending outward of the frame wall around the cylindrical frame base 46 that is dimensioned to be seated and retained in the annular groove 22 of the split stiffening band 12. The stent fabric 44 is sewn together to extend all over the interior surface of the stent frame 42, over the exterior surface of the posts 51, 53, and 55 and sewn together along either side of the stent flange 48, leaving the stent flange 48 exposed.

An alternate suturing ring 10' is depicted in FIGS. 6 and 7 that differs from suturing ring 10 only in that the fabric strip ends of the suturing ring fabric 32 are not sewn together over the band split ends 14 and 16, whereby the suturing ring 10' itself has split ends. Certain of the interlocking mechanisms contemplated by the invention may require direct access to the band split ends 14 and 16 in order open and close the restraints. The suture 38 can be used to interlock and restrain the band split ends 14 and 16 when the suturing ring fabric is sewn together as in suturing ring 10 shown in FIG. 1 or is not sewn together as in alternate suturing ring 10' shown in FIG. 7.

Figure 8:
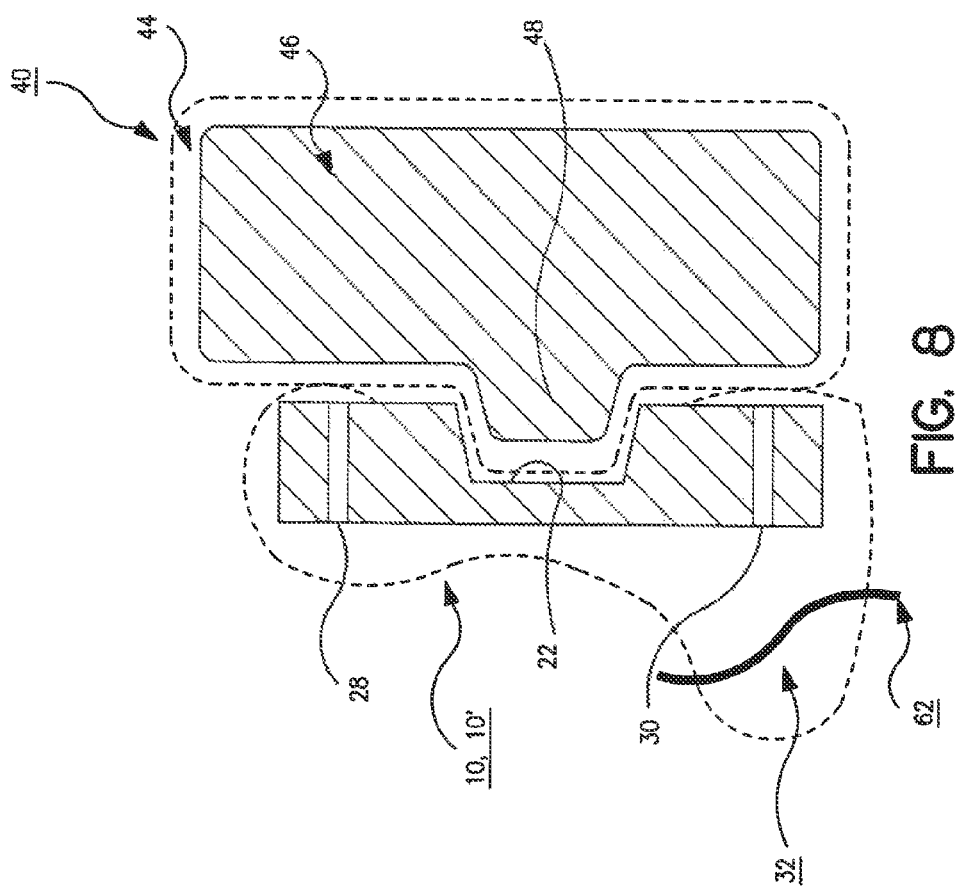
FIG. 8 is a cross-section view taken along lines 8-8 of FIG. 1 illustrating the mating engagement of the fabric covered split stiffening band of the suturing ring against the outer wall of the fabric covered stent.

FIG. 8 is a cross-section view taken along lines 8-8 of FIG. 1 illustrating the mating engagement of the fabric covered split stiffening band 12 of the suturing ring 10 or 10' against the outer wall of the fabric covered valve stent frame 46. In particular, the exposed annular flange 48 fits into the exposed band groove 22 in an interference fit that holds the stent 40 firmly but enables the stent 40 to be rotated when sufficient torque is applied to it during surgery.

Figure 9:
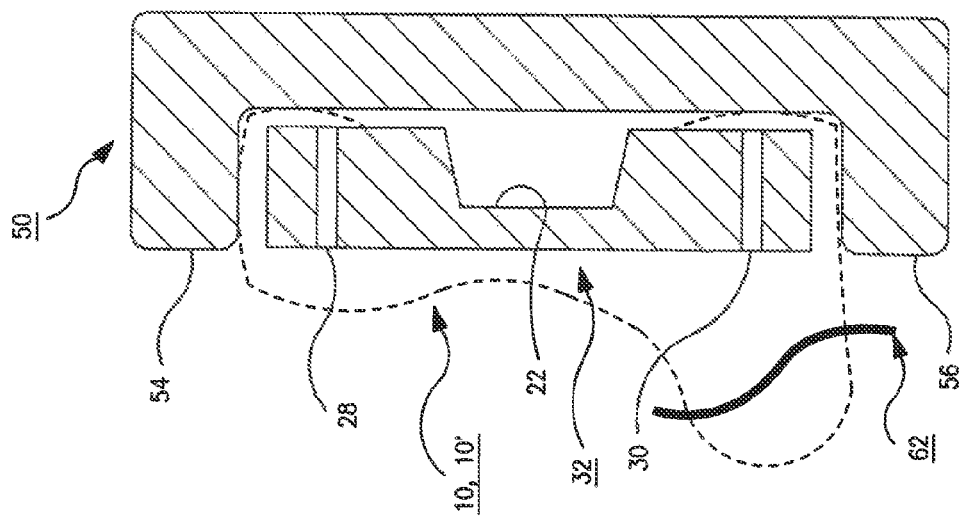
FIG. 9 is a cross-section view taken along lines 9-9 of FIG. 7 illustrating the mating engagement of the fabric covered split stiffening band of the suturing ring against the outer wall of the valve body.

The particular configuration of the suturing ring 10 enables suturing ring 10 or alternate suturing ring 10' to be used to engage and retain a conventional mechanical heart valve body 50 of the type depicted in FIGS. 6 and 7. The simplified depiction of the valve body 50 shows that the valve body outer wall 52 is cylindrical between upper and lower outwardly extending flanges 54 and 56. The annulus diameter AD2 and the width of the suturing ring 10 or 10' between axial ends 24 and 26 are selected so that the interior band sidewall 18 is seated and retained within the U-shaped annular channel formed between the upper and lower flanges 54 and 56. The inwardly extending groove 22 does not play any role in or interfere with retention of the suturing ring 10 or 10' within the U-shaped annular channel formed between the upper and lower flanges 54 and 56 as shown in FIG. 9.

The surgical steps of initially implanting a tissue valve or mechanical valve of the present invention are greatly simplified by the present invention. The surgical method comprises first surgically exposing and excising the dysfunctional native heart valve and preparing the valvular rim 60 shown in FIG. 10 in the conventional manner. An array of sutures 62 is extended through the valvular rim tissue and the suturing ring fabric 32 as shown in FIG. 10. The suturing thread is passed through the valvular rim tissue and then returned through the fabric 32. If desired, pledgets may be used to reduce the possibility of cutting or tearing the tissue when tightening the sutures 62. In this situation, double armed sutures are first passed through the valvular rim tissue and then through the suturing ring fabric 32.

The suturing ring 10 can then be advanced over the sutures 62 and against the valvular rim 60 while holding the sutures 62 taut. The suture ends are then tied together against the suturing ring fabric to fix the suturing ring 10 in place, and the suture ends are then trimmed. The sutures 62 through the suturing ring fabric 32 are also shown in FIGS. 1, 8 and 9. The connection between the suturing ring 10 and the valvular rim tissue is carefully checked in an effort to prevent development of perivalvular leaks or dehiscence after the heart valve mechanism is in place.

The suturing ring diameter AD1 is expanded if necessary so that the valve frame, e.g., the depicted valve stent 40 or the valve body 50, can then be inserted into the annulus of the suturing ring 10 and seated as described above. The unrestrained suturing ring annulus diameter AD1 is either expanded or compressed to the restrained suturing ring annulus diameter AD2 if necessary to seat the suturing ring 10 about the valve frame. The valve frame can then be rotated to the optimal orientation within the suturing ring 10. The restraint, that is the suture 38 or other interlocking mechanism is then affixed to inhibit any spontaneous rotation or detachment of the valve frame from the suturing ring annulus. The valve function is checked to make certain it is oriented optimally. If further rotation is necessary, it may be necessary to release the restraint, rotate the valve frame, and repeat the restraining steps. The conventional surgical closures are then made.

The initial implantation procedure can be further simplified by inserting the valve frame into the stiffening ring annulus while both are supported above and away from the valvular rim 60 by the extended array of sutures 62 held taut during the procedure. Thus, the valve stent 40 can be inserted into the annulus of the suturing ring 10 as shown in FIG. 10, and the assembly can be advanced over the taut array of sutures 62 to seat the suturing ring 10 against the valvular rim 60. The valve stent 40 can still be rotated within the suturing ring annulus to the optimal orientation before or after the suturing ring 10 is sutured against the valvular rim 60 and the restraint is affixed to the band split ends 14 and 16.

Figure 12:
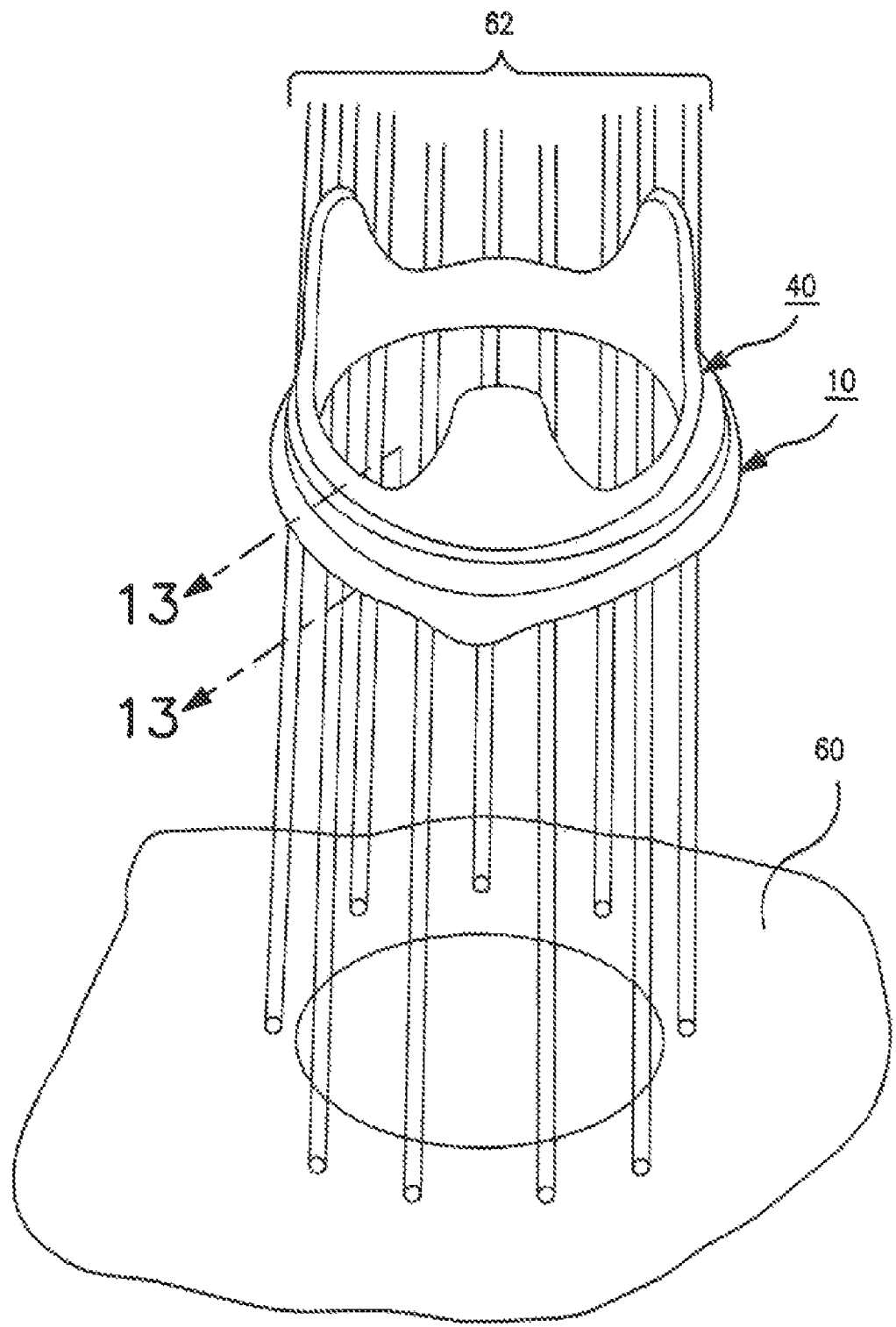
FIG. 12 is an illustration of the valve stent seated into the suturing ring annulus enabling the assembly to be advanced along the taut sutures and seated firmly against the valvular rim when the fabric covered, split stiffening band is restrained and the sutures are entrapped between the suturing ring inner wall and the stent outer wall.

In a further aspect of the invention, the sewing of the suturing ring to the valvular rim in the initial implantation steps is simplified such that suture knots about the suturing ring surface can be eliminated. In this aspect, the plurality of sutures 62 that are sewn through the valvular rim 60 around its circumference are extended through the suturing ring annulus (at least in part) as shown in FIG. 11. The sutures 62 are entrapped between the suturing ring annulus and the outer wall of the valve frame in the subsequent steps, e.g., by the valve stent 40 as shown in FIG. 12. The valve stent 40 can be inserted into the annulus of the suturing ring 10 as shown in FIG. 12, and the assembly can be advanced over the taut array of sutures 62 to seat the suturing ring 10 against the valvular rim 60. The valve stent 40 can still be rotated within the suturing ring annulus to the optimal orientation before or after the suturing ring 10 is sutured against the valvular rim 60 and the restraint is affixed to the band split ends 14 and 16. The free ends of the sutures 62 are then trimmed down to the surface of the suturing ring fabric 32 in the final implantation step prior to closure. The relatively bulky knots that can abrade tissue valve leaflets, be foci of coagulation or thrombus formation, and can interfere with blood flow or valve operation are eliminated.

It will be understood that a mechanical valve mechanism can be substituted for the tissue valve mechanism schematically illustrated in FIGS. 10-12.

In one simple implementation of this further aspect, the sutures 62 are sewn through an axial end band or both axial end bands of the suturing ring fabric 32 at spaced apart locations around the circumference of the suturing ring 10 so as to support the suturing ring 10 and to maintain the sutures generally evenly spaced apart. Then, the exposed ends of the sutures extending out of the suturing fabric 32 can be tied off.

Alternatively, each of the sutures 62 can be extended through the suturing fabric 32 and through an array of suture guides formed in or supported by the split stiffening band 12. For example, the sutures 62 can be sewn through the preformed holes or slots 28 through the split stiffening band 12 that are also used in stitching the suturing ring fabric 32 to the split stiffening band 12. The sutures 62 are brought up from the valvular rim 60 through the suturing ring annulus and then extended outward via an attached suture needle (not shown) through the overlying suturing ring fabric 32 and preformed holes or slots 28, back inward around the suturing ring fabric 32 overlying the band axial end 24, and then back outward through the overlying suturing ring fabric 32 and preformed holes or slots 28. Conversely, the sutures 62 are brought up from the valvular rim 60 through the suturing ring annulus, brought outward around the suturing ring fabric 32 overlying the band axial end 24, then extended via the attached suture needle back inward through the overlying suturing ring fabric 32 and preformed holes or slots 28, and then back outward around the suturing ring fabric 32 overlying the band axial end 24.

FIG. 13 illustrates the entrapment of a suture 62 extending from the valvular rim 60 between the inner wall of the suturing ring 10, 10' and the outer wall of the stent 40, particularly illustrating the seated stent flange 48 within the suturing ring groove 22. Advantageously, the free ends of the sutures 62 can routed through the suturing ring fabric 32 and upper suture grooves or holes 28, around the upper band axial end 24 and suturing ring fabric 32, pulled tight to affix the suturing ring 10, 10' snugly against the valvular rim 60, and tied off using a single hitch 64 as shown in FIG. 13. FIG. 14 illustrates the entrapment of a suture 62 extending from the valvular rim 60 between the inner wall of the suturing ring 10, 10' and the outer wall of the mechanical valve body 50, particularly illustrating the suturing ring 10, 10' seated in the U-shaped channel of the valve body 50 as described above. The free ends of the sutures 62 can routed through the suturing ring fabric 32 and upper suture grooves or holes 28, around the upper band axial end 24 and suturing ring fabric 32, pulled tight to affix the suturing ring 10, 10' snugly against the valvular rim 60, and tied off using a double hitch 66 as shown in FIG. 14. The single hitch 64 or double hitch 66 can be efficiently made by the surgeon manipulating the suturing needle to make the hitch loop(s), pulling the sutures 62 tight, and then snipping the suture off close to the single hitch 64 or double hitch 66. The single hitch 64 or double hitch 66 can be used to attach the suturing ring 10, 10' to the valvular rim 60 to receive any type of mechanical or tissue heart valve mechanism. The single hitch 64 or double hitch 66 is relatively easier to accomplish and smaller in comparison to the traditionally used single or double square knots.

Further implementations of the suture guides of this second aspect of the invention are illustrated in FIGS. 15 and 16, wherein the suturing ring fabric 32 and stent fabric 44 are not shown for convenience of illustration. In these embodiments, the routing of each suture 62 is accomplished using suture guides supported by or formed in the interior band sidewall 18. For example, a modified split stiffening band 12' is employed having a pair of flanges 70 and 72 extending inward above and below the groove 22 that fit on either side of the stent flange 48. A plurality of axially aligned pairs of suture guides or holes 74 and 76 are formed through the band flanges 70 and 72, respectively arrayed about the circumference of the split stiffening band 12'. One or more suture 62 can be extended through each axially aligned pair of suture holes 74, 76 and across the intervening groove 22. The sutures 62 can be employed to suture the suturing ring to the valvular rim 60 as shown in FIGS. 11 and 12 and are then entrapped within the groove 22 by the stent flange 48 when the band split ends 14 and 16 are restrained.

Furthermore, the band flanges 70 and 72 are preferably notched or slotted from the suture holes 74, 76 to the flange edges to enable the one or more suture 62 to be laterally, rather than axially, inserted into the axially aligned suture holes 74, 76. The split stiffening band 12 is flexible enough that the band split ends 14 and 16 can be separated apart to widen the slots or notches enough to pass the suture laterally into the axially aligned suture holes 74, 76 whereupon the slots or notches would then narrow upon release of the separation force.

The axially aligned suture holes are not employed in the further alternative split stiffening band 12" depicted in FIG. 16. Instead, the illustrated convoluted or circuitous path of each suture 62 around the stent flange 48 and the band flanges 70 and 72 and optionally through an upper suture slot 28 increases the resistance to release of each suture 62.

In these ways, the suturing of the suturing ring to the valvular rim is greatly simplified, resulting in fewer and smaller sized knots being required. Tissue ingrowth into the interstices of the suturing ring fabric occurs in time, and the sutures may become unnecessary to retain the suturing ring 10 in place. The single hitch 64 or double hitch 66 is expected to be sufficient to hold the suturing ring 10, 10' in place during the removal of a dysfunctional heart valve mechanism and replacement with a new heart valve mechanism.

FIGS. 17-19 illustrate alternative or additional restraint mechanisms incorporated into the split stiffening band 12 for closing and opening the split stiffening band 12. At least the restraint mechanisms depicted in FIGS. 17 and 18 can be enclosed within the suturing ring fabric sewn together as illustrated by suturing ring 10 of FIG. 1 or exposed at the ends of the suturing ring fabric as illustrated by the suturing ring 10' of FIGS. 6 and 7.

In FIG. 17, a spring 82 is integrally formed to extend between the band split ends 14 and 16 maintaining the first annulus diameter AD1. The split band ends 14 and 16 can be separated apart to the increased second annulus diameter AD2 through application of force overcoming the spring tension to receive or remove a valve frame. The spring force then brings the split band ends 14 and 16 together when the force is removed. The spring force retains the valve frame seated within the suturing ring annulus and any of the sutures 62 inserted between the valve frame and the suturing ring as described above.

In FIG. 18, the band split ends 14 and 16 are modified to have longitudinally extending mating teeth or hooks 84 and 86 that are normally interlocked to prevent spreading apart of the band split ends 14 and 16 and provide the first annulus diameter AD1. Opposed axial forces can be applied to release and then set the mating teeth or hooks 84 and 86 together to expand the annulus diameter to the second annulus diameter AD2 to receive or remove a valve frame. Force can then be applied longitudinally to reset the mating teeth or hooks 84 and 86 and brings the split band ends 14 and 16 back closer together. The mating teeth or hooks 84 and 86 retain the valve frame seated within the suturing ring annulus and any of the sutures 62 inserted between the valve frame and the suturing ring as described above.

In FIG. 19, the band split ends 14 and 16 are modified to have a longitudinally extending restraint band 88 having snaps or buttons that are received in the suture holes 34 and 36 to prevent spreading apart of the band split ends 14 and 16 and provide the first annulus diameter AD1. One of the snaps or buttons can be released from one of the suture holes 34 and 36 by use of a forceps or the like to expand the annulus diameter to the second annulus diameter AD2 to receive or remove a valve frame. The snaps or buttons can then be reapplied to retrain the split band ends 14 and 16 back closer together. The restraint band retains the valve frame seated within the suturing ring annulus and any of the sutures 62 inserted between the valve frame and the suturing ring as described above.

Figure 20:
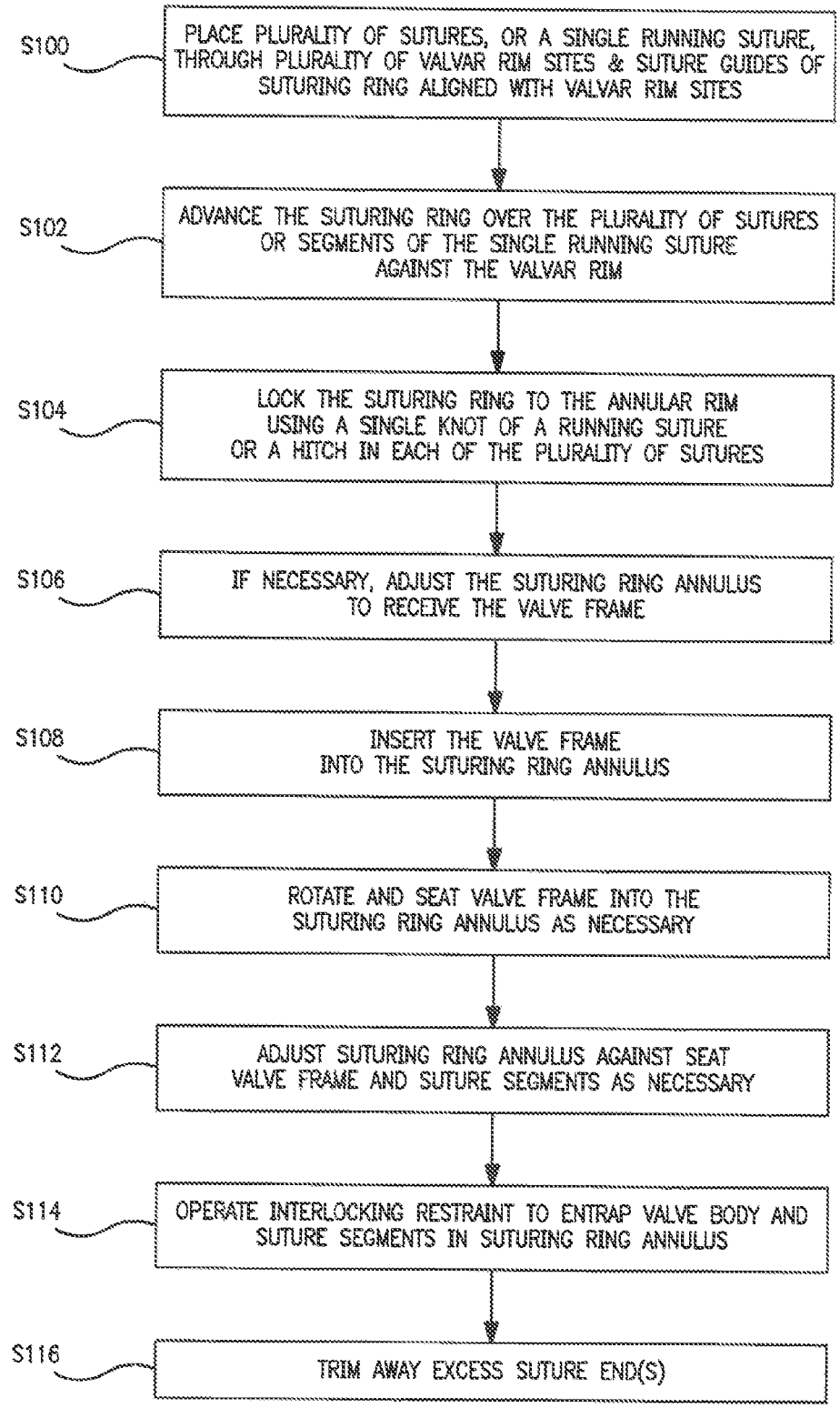
FIG. 20 is a flow chart illustrating one preferred embodiment of initially implanting a suturing ring and heart valve mechanism to form a heart valve prosthesis in accordance with the present invention.

A preferred method incorporating both aspects of the invention of surgical implantation of the suturing rings 10, 10' of the present invention and fixation of a tissue valve stent 40 or a mechanical valve body 50 into the suturing ring annulus is depicted in FIG. 20. In this method, the suturing ring 10, 10' is first surgically implanted in steps S100-S104 to the prepared valvular rim. The surgeon can either use a plurality of sutures 62 fitted through each one or adjacent pairs of the above-described suture guides or a single running suture fitted through all of the suture guides. The danger that the single running suture may break during chronic implantation and cause the suturing ring 10, 10' to loosen from the valvular rim 60 is overcome because multiple parallel segments of the single running suture are entrapped between the stiffening ring 12 and the valve frame 40 or 50 that would remain firmly attached to the valvular rim 60.

Preferably, in either case, the suture(s) 62 are sewn through a suture guide, then inferiorly through a site of the valvular rim that the suture guide will be aligned with, then back superiorly through a site of the valvular rim that the adjacent suture guide is aligned with, and then through the adjacent suture guide in step S100. The suturing is facilitated because the surgeon's view of the sites of the valvular rim is not obstructed by any valve structure. In addition, the surgeon can extend instruments or a finger through the empty suturing ring annulus to effect sewing the suture(s) through the sites of the valvular rim 60 to speed the process and avoid damage to the valvular rim that could other wise occur.

Figure 22:
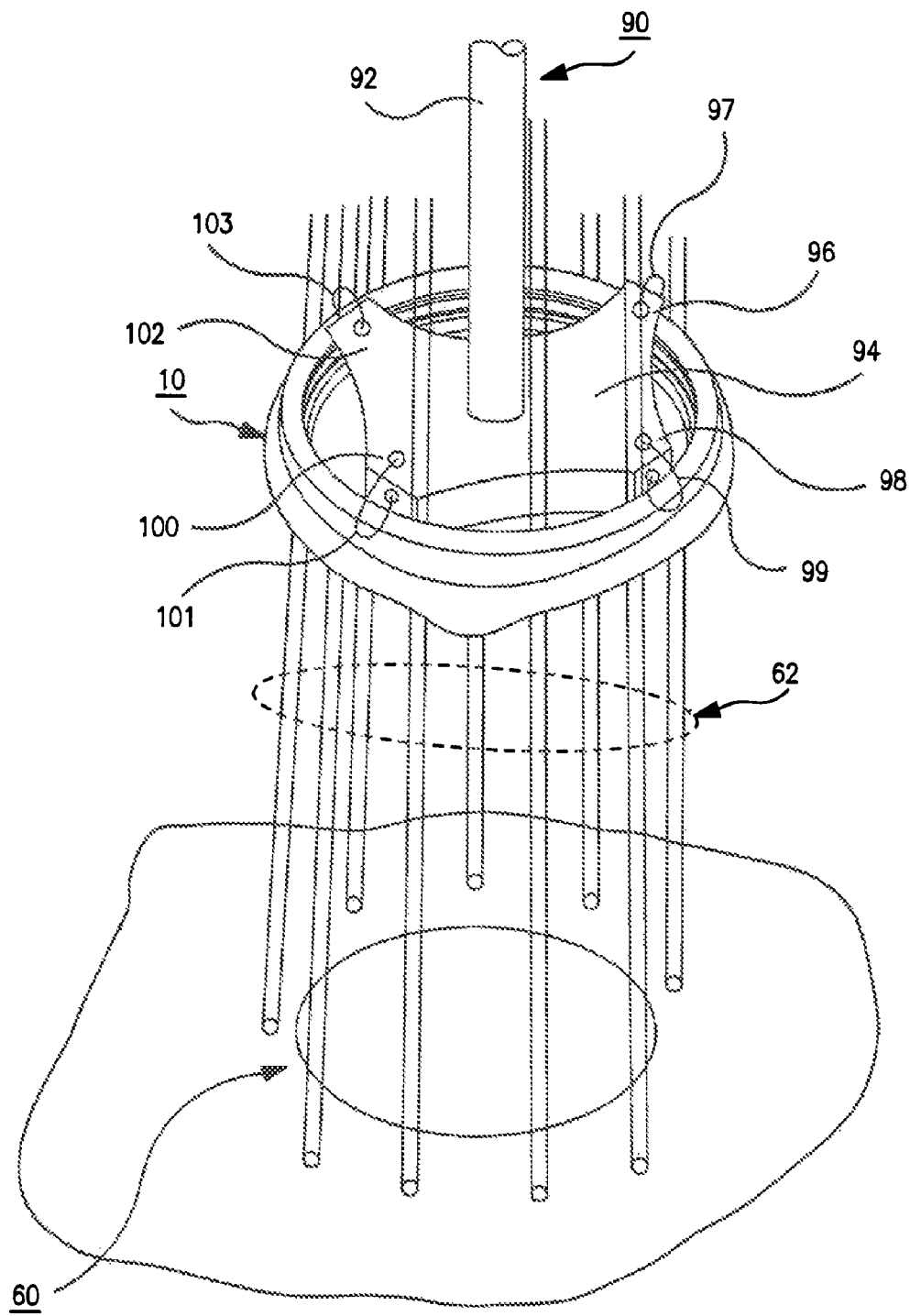
FIG. 22 is a perspective schematic view of a suture ring holder engaging the suturing ring by severable sutures to enable positioning and suturing of the suturing ring to the valvular rim.

The suturing ring 10, 10' can be suspended on taut suture(s) 62 in alignment with valvular rim 60 as shown in FIG. 11 and advanced against the valvular rim 60 over the taut suture(s) in step S102. One way of holding the suturing ring 10, 10' using a tool 90 is depicted in FIG. 22. Tool 90 is formed of an elongated handle 92 attached to a spanner 94 having a plurality of arms, e.g., arms 96, 98, 100, 102, that extend to the suturing ring annulus and are sutured to the stiffening ring 10, 10' by tool sutures 97, 99, 101 and 103. The stiffening band and the arms 96, 98, 100, 102 are formed with special suture holes that tool sutures 97, 99, 101 and 103 extend through and tied. The tool sutures 97, 99, 101 and 103 are adapted to be cut when the suturing ring 10, 10' is snugged up against the valvular rim 60.

The suturing ring 10, 10' is snugged up against and locked to the valvular rim 60 by tying a knot in the single running suture or knotting the ends of the individual sutures 62 in step 104. Preferably, the suture(s) 62 are inserted through the upper suture slots 28 as shown in the examples of FIGS. 13 and 14, and the single or double slip hitch 64 or 66 is formed in the turns of the suture extending over the suturing ring fabric 34. Slip hitches are easier to form by the surgeon using instruments than a square knot.

The suturing ring annulus is adjusted as necessary in step S106 so that the valve frame 40 or 50 is then inserted into it. For example, the gap G can be widened as necessary to receive the flange 48 within the slot 22 or to fit the suturing ring 10, 10' into the U-shaped channel of the mechanical valve body 50 as described above. The valve frame 40 or 50 is inserted into, rotated and seated in steps S108, S110, and S112 in the ways described above.

Figure 23:
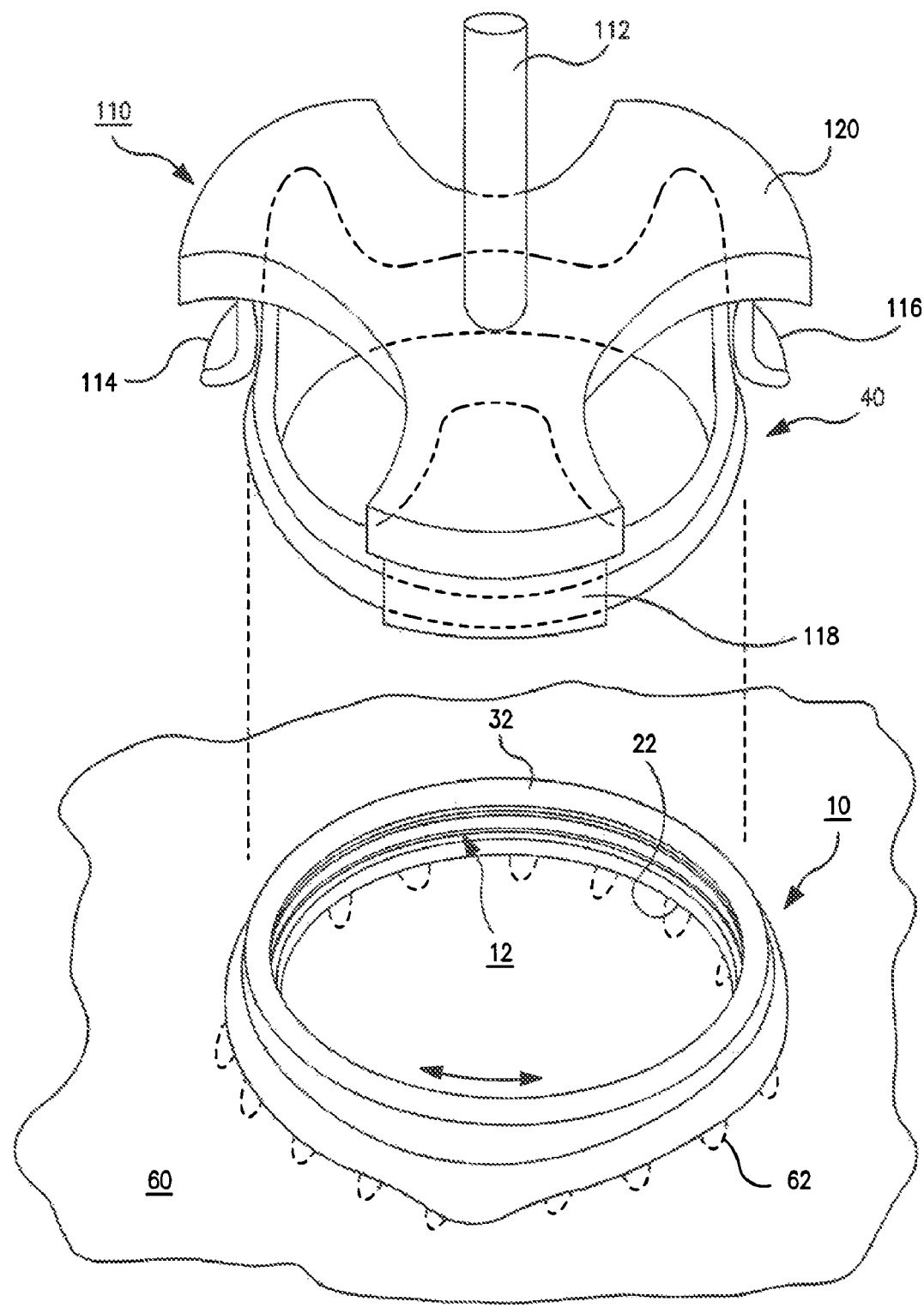
FIG. 23 is a perspective schematic view of a stent holder engaging the stent frictionally or by severable sutures to enable positioning of the stent into the suturing ring.

The valve mechanism is preferably mounted to a valve holder tool as it is inserted into and seated in the suturing ring annulus. For example, a stent holder 110 is illustrated in FIG. 23 comprising a stent holder handle 112 attached to a stent holder spanner 120 having three fingers 114, 116 and 118 that extend over and against the stent struts and thereby frictionally engage the stent 40. A suture may also be placed around or through holes in the three fingers 114, 116 and 118 and the corresponding stent struts to hold the stent 40. The stent holder 110 is manipulated to insert the stent 40 into the sewing ring annulus in step S108. The lengths of the three fingers 114, 116, 118 are selected so that the outwardly ending free ends of the three fingers 114, 116, 118 bear against the suturing ring 10, 10' when the stent flange is positioned to be seated in the groove of the stiffening ring as described above. The outwardly ending free ends of the three fingers 114, 116, 118 bearing against the suturing ring 10, 10' when the stent flange is properly seated in the groove of the stiffening ring 10. 10' prevent the surgeon from extending the stent 40 all the way through the suturing ring annulus.

The interlocking restraint of one of the above-described types is operated in step S114. Preferably, the interlocking restraint is the above-described suture 38, and that is sewn through the suture holes 34 and 36, drawn tight, and either tied or thermally welded against the suturing ring fabric in step S114.

The excess suture length of the running suture or lengths of the separate sutures 62 are then trimmed in step S116. Advantageously, tightened slip hitches 64 or 66 are small in size and will remain in place when a replacement surgical procedure of the types described above are undertaken.

The various aspects of the suturing ring 10, 10' of the present invention employing any of the interlocking restraints presents the surgeon with a wide range of possible ways of surgically implanting it upon or against the valvular rim 60. The suturing ring 10, 10' of the present invention can be supplied with the outwardly extending collar to enable traditional suturing through it as depicted in FIGS. 1, 8 and 9. However, the surgeon can ignore the suturing ring fabric collar and follow any of the above-described techniques, e.g., steps S100-S104 to entrap segments of the suture(s) 62 between the valve frame and the suturing ring annulus.

It is desirable in many instances to implant a heart valve prosthesis in or to a valvular rim 60 having as large a valve annulus as possible to enable maximal unobstructed blood flow through it when the occluder is not seated. Advantageously, a larger diameter suturing ring 10, 10' (accommodating a larger diameter valve mechanism and valve annulus) can be selected to fit the valvular rim if the surgeon follows any of the above-described techniques, e.g., steps S100-S104 to entrap segments of the suture(s) 62 between the valve frame and the suturing ring annulus rather than suturing through the fabric collar. Models of suturing ring 10, 10' can be provided with a minimal sized outwardly extending collar of the suturing ring fabric 32 and a relatively larger suturing ring annulus for selection by a surgeon intending to follow any of the above-described techniques, e.g., steps S100-S104 to entrap segments of the suture(s) 62 between the valve frame and the suturing ring annulus.

Figure 21:
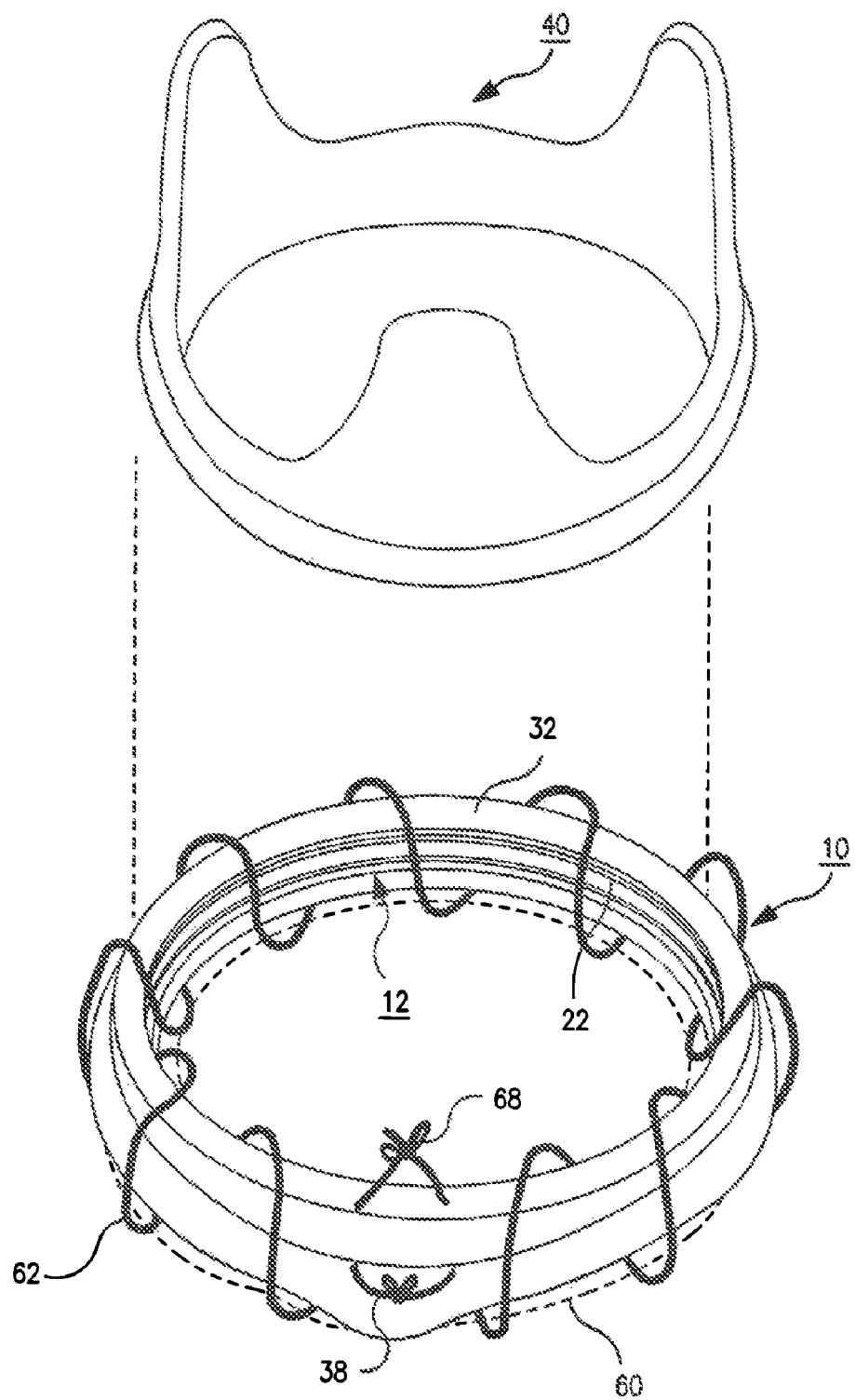
FIG. 21 is a perspective view of a stent arranged to be inserted into the annulus of a suturing ring of the present invention sutured by a single running suture to a valvular rim.

All of the above described methods of initially implanting the suturing ring 10, 10' are facilitated by having the ability to see through, extend the surgeon's finger or instruments through and extend sutures through the open suturing ring annulus. A further simplified way of suturing the suturing ring 10, 10' to a valvular rim 60 (which in practice may simply be the tubular valvular annulus remaining after surgical excision of the native heart valve) employing a single suture 62 is depicted in FIG. 21. This method, the suturing ring 10, 10' is held within or against the valvular annulus constituting the valvular rim 60 by a suitable instrument. A number of loops of the suture 62 are made by the surgeon extending entirely around the suturing ring 10, 10' via the open suturing ring annulus and through adjoining valvular tissue under or within valvular rim 60. The suture ends can be drawn through any selected adjacent pair of any of the suture holes 28, 30, 34, 36 depicted in FIG. 5 and/or just through the suturing ring fabric 32. The suture 62 is pulled taut, the suture ends are tied together in a suture knot 68, and the excess suture is trimmed away. In this way, the surgeon can implant the maximum diameter suturing ring 10, 10' in a tubular valvular annulus that is otherwise difficult sized only a single knot 68 is necessary. Of course, it would also be possible to form separate hitches in the suture ends as described above with respect to FIGS. 13 and 14.

Then, steps S106-S116 of FIG. 20 are followed to affix the valve mechanism in place. The suture segments are entrapped between the suturing ring annulus and the valve frame as described above. These entrapped segments of the suture 62 still hold the suturing ring 10, 10' in place even if the suture 62 happens to break at any point along its length.

The surgical steps of replacing a tissue valve or mechanical valve at a later time are greatly simplified by the present invention. All that is necessary to do is to: 1) Surgically expose the chronically implanted valve mechanism and suturing ring assembly and clean the tissue overgrowth away; 2) Locate the suturing ring restraint; 3) Release the restraint; 4) Insert a scalpel or a blunt probe into the interface between the split ring and the valve frame starting from the split end, 5) Gently peel the split ring from the valve frame along the circumferential direction using the same instrument, 6) Remove the valve mechanism from the annulus of the suturing ring; 7) Insert and seat the new replacement valve mechanism into the annulus; 8) Attach the replacement valve mechanism therein following any of the above-described techniques depending upon the particular design of the suturing ring and the replacement valve mechanism; and 9) Complete the surgical closure.

As noted above, the restraint can be a suture sewed through the suturing ring fabric and suture holes adjacent the split ends of the stiffening ring. The suture can be identified at the bunched fabric that the suture is sewn through. The fabric can be marked or colored to indicate where the suture is located to be cut in step 3), and a new suture is to be sewn in the attachment in step 8). If the alternative restraints illustrated in FIGS. 17-19 are employed, then they are opened in step 3) and closed in step 8).

Advantageously, this process allows the dysfunctional valve mechanism to be replaced by the same or a different type of valve mechanism that can be seated into the annulus of the suturing ring in step 7). However, the chronically sewn-in suturing ring can also be used as a docking station for an incompatibly dimensioned heart valve prosthesis comprising a tissue or mechanical heart mechanism that is supplied with an integral suturing ring. In this case, step 8) can be replaced by placing the integral valve suturing ring within or onto the annulus of the chronically sewn-in suturing ring and suturing them together.

Figure 24A:
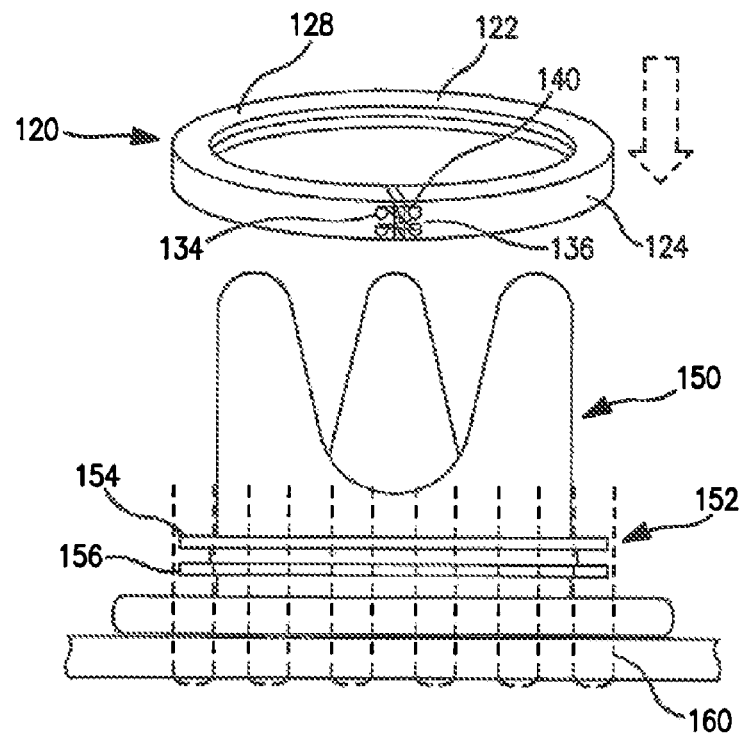
FIG. 24a-b are plan schematic views of one embodiment in which a band engages a circumferential frame portion on a valve body in order to capture sutures securing the valve to a valvular rim.
Figure 24B:
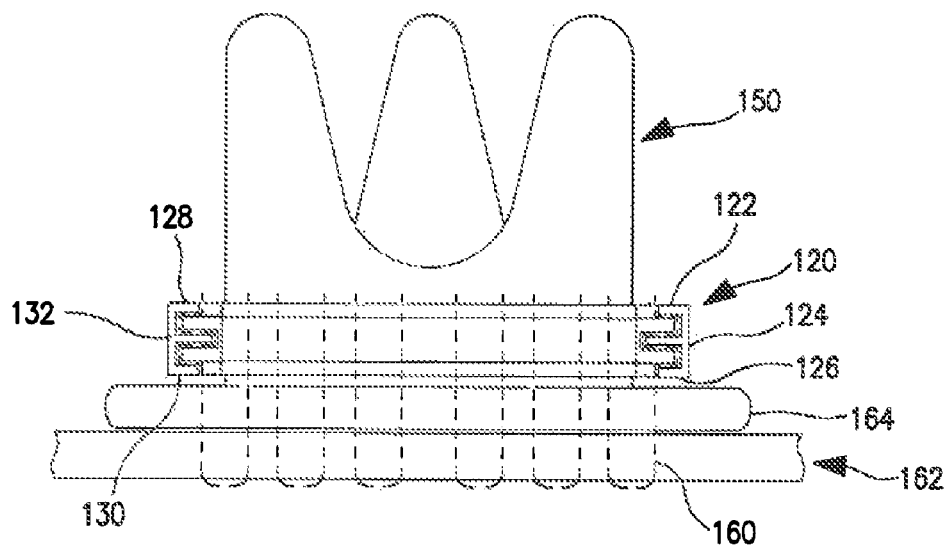

Referring now to FIGS. 24a-b, in yet another embodiment of the invention, a band 120 is applied to a valve having a suturing ring in order to secure sutures in place. The band 120 has substantially the same properties as the band 12 discussed previously. Band 120 has a top portion 122, an outside portion 124, and a bottom portion 126. The top portion 122 and bottom portion 126 include inwardly extending circumferential flanges 128, 130 respectively. Centrally located on the band 120 is a third inwardly extending circumferential flange 132 that is longer than the other flanges 128, 130. The band includes split ends 134, 136, which are secured together by a restraint mechanism such as a suture 140 that is capable of locking the position of the split ends 134, 136. The suture 140 or other restraint mechanism is preferable made from a resilient material such as nitinol, which can be pseudoelastically deformed to open the band 120 and then released to return it to an undeformed condition, thereby closing the band 120 by pulling the split ends 134, 136 together. Alternatively, a nitinol restraint mechanism can be used as a shape memory device in which the restraint mechanism responds to warming to body temperature by transforming the restraint from its martensitic state to its austenitic state. Such a phase transformation can pull the split ends 134, 136 together as the device is warmed. Other restraint mechanisms can be used as well, but most preferably the selected restraint mechanism permits the surgeon implanting the device to remove or loosen the restraint mechanism if the band 120 must be removed, released or repositioned.

Valve 150 can be a mechanical or tissue valve having a frame or stent. Valve 150 is shown to be a tissue valve having a frame portion 152 that includes a first, outwardly-extending circumferential flange 154 at the top of the frame portion 152 and a second, outwardly-extending circumferential flange 156 at the bottom of the frame portion 152. As shown in FIG. 24b, the flanges 154, 156 are sized to fit within recesses in the band 120 between inwardly extending flanges 128, 130, 132 and are spaced apart to permit the centrally located flange 132 to reside between the flanges 154, 156. The band 120 and frame portion 152 thereby cooperate to form an interlocking engagement that can engage and restrain the movement of a suture 160 that may be introduced and secured between them. It will be appreciated that many other configurations of interlocking elements can be used to engage and restrain the movement of a suture. Preferably, such interlocking elements are characterized by a tortuous path for the suture and closely mating surfaces between the band 120 and the frame portion 152.

In operation, the valve 150 is secured by a plurality of sutures 160 to a prepared valvular rim 162 by bringing the sutures through a suture ring 164, through a portion of the valvular rim 162 and returning the suture through the suture ring 164. The ends of the sutures 160 extending away from the valvular rim 162 preferably run through the suture ring 164 at points near the outer portion of the frame portion 152. When all of the sutures 160 have been positioned, the suture ring 164 is pressed against the valvular rim 162 and the sutures 160 are drawn away from the suturing ring 164 to take up any slack. The band 120 is then placed over the valve 150 and advanced into position over the frame portion 152. In order to permit the band 120 to achieve a mating engagement with the frame portion 152, the split ends 134, 136 are spaced apart sufficiently to permit the inwardly extending flanges 130, 132 to clear outwardly extending flanges 154, 156. The split ends 134, 136 may be brought to the spaced apart position by prying them apart slightly, if that is necessary. The restraint mechanism such as the suture 140 is preferably affixed to the split ends 134, 136 prior to the time the band 120 is placed over the frame portion 152. If the restraint mechanism is a resilient restraint, such as a spring, the restraint can be in place as the split ends 134, 136 are brought to a spaced apart position and then simply released. Alternatively, a nitinol restraint can be allowed to warm to body temperature to pull the split ends 134, 136 together. In yet another way, a restraint mechanism such as a suture 140 can be loosely positioned in apertures on the spilt ends 134, 136 and can be brought from an unsecured state to a taut, secured state by the surgeon after the band 120 is placed over the frame portion 152. If desired, a suitable ring-spreading tool such as those known in the art can be used to facilitate the correct positioning of the split ends 134, 136. Once the band is in a mating position with the frame portion 152, the split ends 134, 136 can be drawn together in order to urge the flanges 128, 130, 132 of the band 120 into contact with the sutures 160 and to drive the sutures 160 into the recesses in the frame portion 152 defined by the flanges 154, 156 and into recesses defined in the band 120 by the flanges 128, 130, 132. The band 120 then secures the sutures 160 from movement and excess suture material extending above the top portion 122 of the band may be removed. In order to facilitate a rapid surgical procedure, the sutures so secured between the band 120 and the frame portion 152 are secured entirely by the band 120 and frame portion 152 without the need to tie any knots in the sutures 160. If the surgeon finds it necessary to tighten any of the sutures 160 after the band 120 is secured over the frame portion 152, the split ends 134, 136 can be drawn apart until the sutures to be tightened are moveable. The sutures 160 can then be pulled tight and the band 120 drawn against the frame portion 152 to resecure the sutures 160.

Figure 25A:
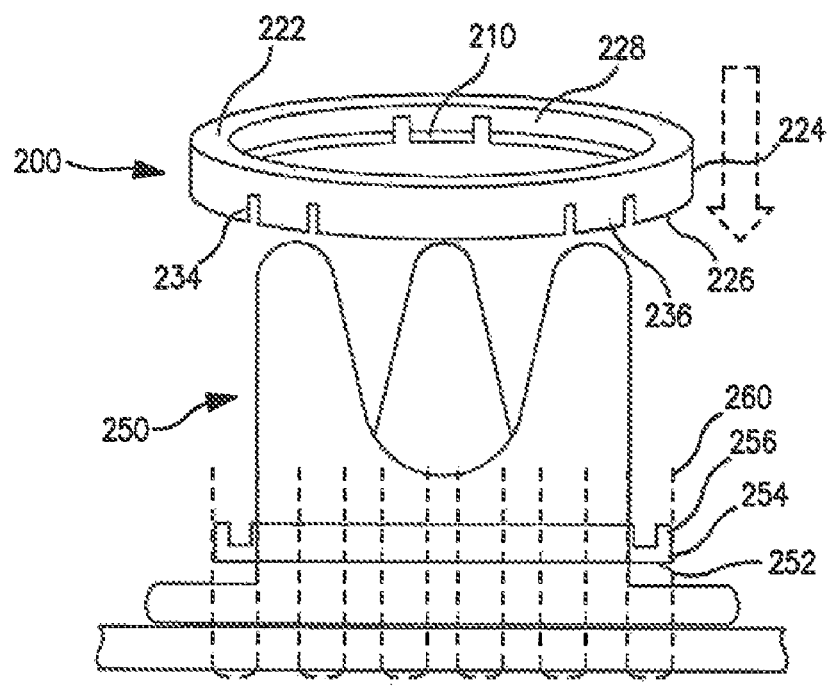
FIG. 25a-b are plan schematic views of another embodiment in which a band engages a circumferential frame portion on a valve body in order to capture sutures securing the valve to a valvular rim.
Figure 25B:
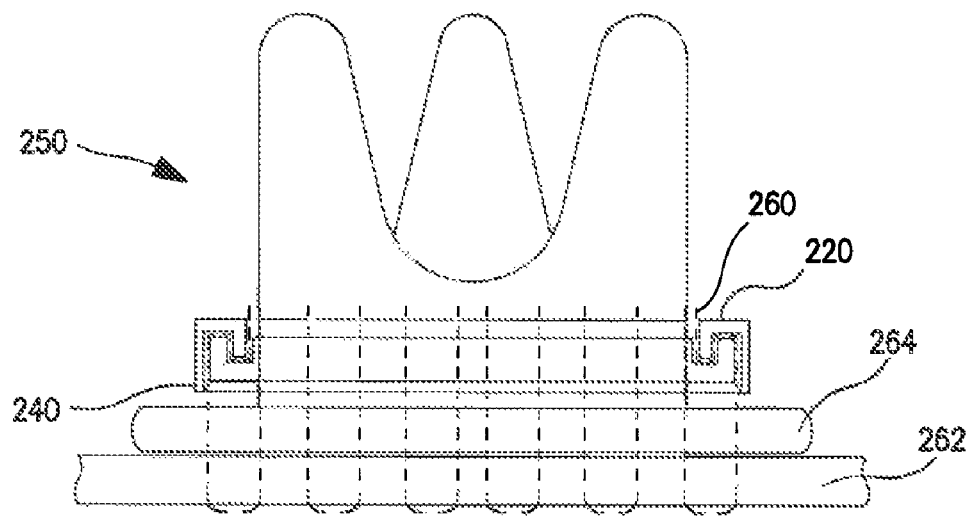
Figure 26A:
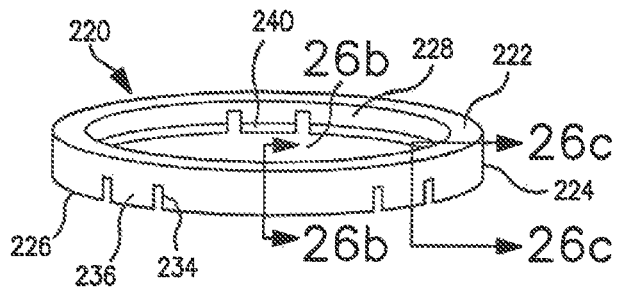
Figure 26B:
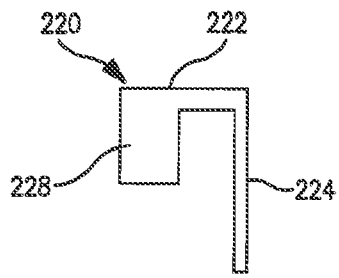
FIG. 26b is a cross sectional view of the band of FIG. 26a taken along the line 26b-26b.
Figure 26C:
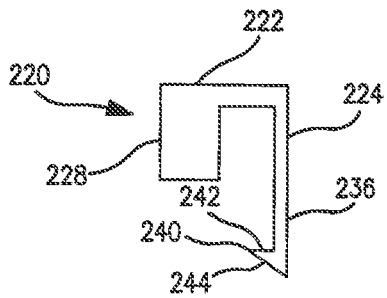
FIG. 26c is a cross sectional view of the band of FIG. 26a taken along the line 26c-26c.
Figure 26D:
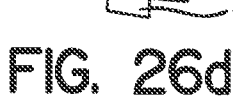
Figure 26E:
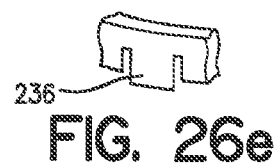
FIG. 26e is a partial perspective view of yet another embodiment of a band similar to that shown in FIG. 26a FIG. 27a is a cross sectional view of the band and frame portion of FIG. 25a moving into engagement.

Referring now to FIGS. 25a-b and FIGS. 26a-e, in yet another embodiment of the invention, a band 220 is also applied to a valve having a suturing ring in order to secure sutures in place. Band 220 is made in a closed ring configuration with a top portion 222 joined at an outside edge to an outside portion 224. The top portion 222 comprises an inwardly extending flange that also joins at an inner edge with a downwardly extending circumferential flange 228. The band 220 includes a plurality of splits 234 that extend through the outside portion 224 from a bottom edge 226 upward to a central portion of the outside portion 224. The splits 234 do not extend completely through the band 220. The splits 234 are preferably spaced around the circumference of the band 220 such that pairs of adjoining splits create tab portions 236 around the circumference of the band 220. The tab portions 236 can also extend partially below the bottom edge 226 of the ring as in FIG. 26e. Also, the tab portions 236 may be made independent of any splits as shown in FIG. 26d where the tab portions 236 are shown protruding below the bottom edge 226. A barbed portion 240 is on the lower edge of each of the tab portions 236, as best appreciated in cross-section in FIG. 26c. The barbed portions 240 include a substantially flat upper portion 242 and an angled lower portion 244. Portions of the band 220 between the tab portions 236 can be formed without a barbed portion as shown in FIG. 26b. The tab portions are designed so that they may be resiliently spread radially outwardly at the lower, barbed portion 240 and then released to return them to an unspread position. The tab portions 236 can, by their resilient deformation, form a locking mechanism with a complimentary structure on a frame portion 252 of a valve 250 in a locking fit. Locking mechanisms employing structures other than a barb shape can also be used so long as they provide a positive, locking attachment between the band 220 and the frame portion 252. Preferably, multiple tabs are used on the band 220 and are spaced around the circumference of the band 220 in order to provide an even locking attachment between the band 220 and frame portion. Two or more such tabs are preferred.

Figure 27A:
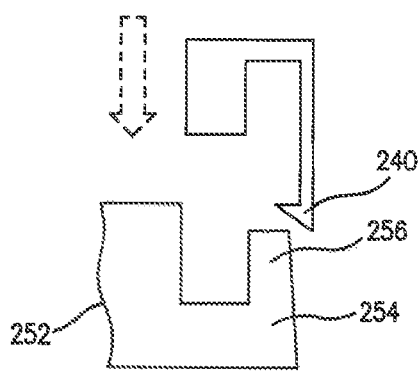
FIG. 27b is a cross sectional view of the band and frame portion of FIG. 27a in an engaged and locked position.
Figure 27B:
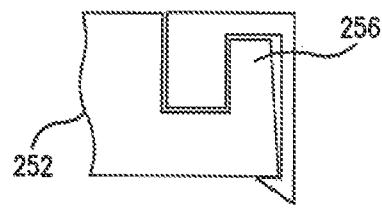
Figure 28A:
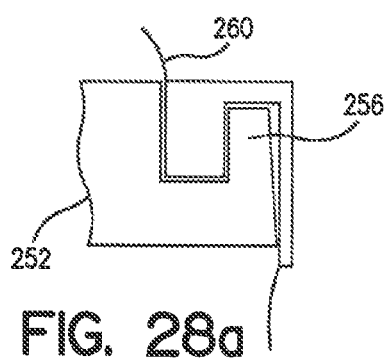
Figure 28B:
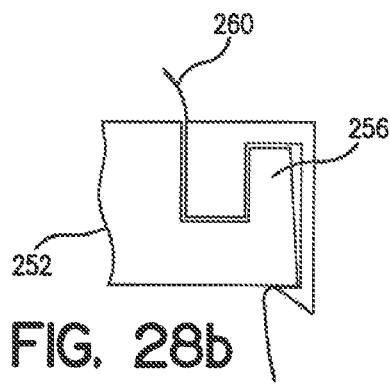

Referring now to FIG. 25a-b and FIG. 27a-b, valve 250 can be a mechanical or tissue valve having a frame or stent. Valve 250 is shown to be a tissue valve having the frame portion 252 that includes a first, outwardly-extending circumferential flange 254 with an upwardly extending portion 256 that forms a circumferential recess in the flange. The recess is therefore open in the outflow side of the valve. As shown in FIG. 25b and FIGS. 27a-b, the flange 254 and upwardly extending portion 256 are sized to fit within the recess in the band 220 while the downwardly extending flange 228 of the band is sized to fit within the recess in the flange 254. Preferably, the upwardly extending portion 256 is tapered slightly on its outer edge such that the tab portion 236 will be deflected outwardly by contact with the taper. The band 220 and frame portion 252 thereby cooperate to form an interlocking engagement in which the barb portion 240 catches on a portion of the frame portion 252 and holds the band 220 and frame portion together. As shown in FIG. 25b and FIG. 28a, the mating of the frame portion 252 and band 220 in this manner can prevent movement of a suture 260 that may be introduced and secured between them. Because the barb portion 240 has an angled lower portion 244, and because of the taper on the upward extending portion 256 the placement of the band on the flange is a simple press fit. That is, the band 220 can be readily pressed onto the flange 254 by a straight downward motion that deflects the tab portions 240 simultaneously and causes them to lock simultaneously in a locking fit onto a complementary structure on the flange 254. In the embodiment shown, the barb portion engages the inflow side of the flange 254. It will be appreciated that many other configurations of the locking mechanism can be used, including placing the locking barbs or elements on the flange rather than on the band and applying a band that has a complementary structure for locking the barbs to the band. Thus, a band without splits or tabs could be used according to the invention to engage and restrain the movement of a suture.

In operation, the valve 250 is secured by a plurality of sutures 260 to a prepared valvular rim 262 by bringing the sutures through a suture ring 264, through a portion of the valvular rim 262 and returning the suture through the suture ring 264. The ends of the sutures 260 extending away from the valvular rim 262 preferably run through the suture ring 264 at points near the outer portion of the frame portion 252. When all of the sutures 260 have been positioned, the suture ring 264 is pressed against the valvular rim 262 and the sutures 260 are drawn away from the suturing ring 264 to take up any slack. The band 220 is then placed over the valve 250 and advanced into position over the frame portion 252 and pressed onto the frame portion 252 until a locking fit is achieved between the barbs 240 and the frame portion 252. Preferably, the frame portion 252 is designed to provide a circumferentially cooperating portion that will receive the barbs 240 in any relative rotational orientation of the band 220. Alternatively, the frame portion could be provided with a mark or indicator that could be aligned with a similar mark or indicator on the band in order to align the components. If the surgeon finds it necessary to tighten any of the sutures 260 after the band 220 is secured over the frame portion 252, the tab portions 236 can be resiliently drawn away from the frame portion 252 so that the barbs 240 are released from engagement with the frame portion. The band 220 is then drawn upward until the sutures to be tightened are moveable. The sutures 260 can then be pulled tight and the band 220 can again be pressed against the frame portion 252 to resecure the sutures 260.

The process for pressing the band 220 onto the frame portion 252 can be facilitated by using a pressing tool 270 as set forth in FIGS. 29a-b. The pressing tool 270 includes a cylindrical body 272 and a handle portion 280. The cylindrical body 272 includes a shoulder portion 274 that is configured to engage the band 220. The handle portion 280 includes a portion that is interior to the body 272 and a portion that is exterior to the body and is free to rotate with respect to the body 272 on threads 282 engaging complimentary threads on the body 272. The interior of the body 272 is sized to receive the valve and any valve holder and handle that may be attached to the valve during the surgical procedure. The interior portion of the handle portion is sized to engage with the valve and valve holder. In operation, the pressing tool 270 is placed over the valve and with the band engaged with the body 272 and in place against the frame portion 252, the body is manually rotated to advance the body 272 over the threads 282 relative to the handle 280. This advances the band 220 onto the frame portion 252 until the closure is achieved between the band 220 and frame portion 252. Alternatively, another pressing tool 271 can be used to facilitate positioning of the band 220 as shown in FIGS. 29c-d. A cylindrical body portion 273 includes retention tabs 277 that are configured to grip the band 220. Preferably three or more such tabs 277 are evenly spaced around the body 273 to grip the band 220 evenly at several places. Threaded apertures 275 are on an upper portion of the body 273 in order to permit the body to be secured to the handle of a valve holder by locking elements 289. A sleeve 281 has screw threads 285 on an outer portion thereof and a notch 287 configured to provide an opening for tab 277. The sleeve 281 fits over the body 273. A cap 283 configured to fit over an upper portion of body 273 includes internal screw threads (not shown) which are intended to mate with screw threads 285 on the sleeve 281. In operation, the tool 271 slides over the handle 296 of the valve holder and the locking elements 289 are screwed into locking engagement with the handle 296. The cap 283 is then manually rotated which causes the sleeve 281 to be advanced over the body 273. As the sleeve 281 is advanced, it contacts the band 220 and pushes the band 220 off of the retention tabs 277 and into engagement with the flange of the frame portion.

Figure 30A:
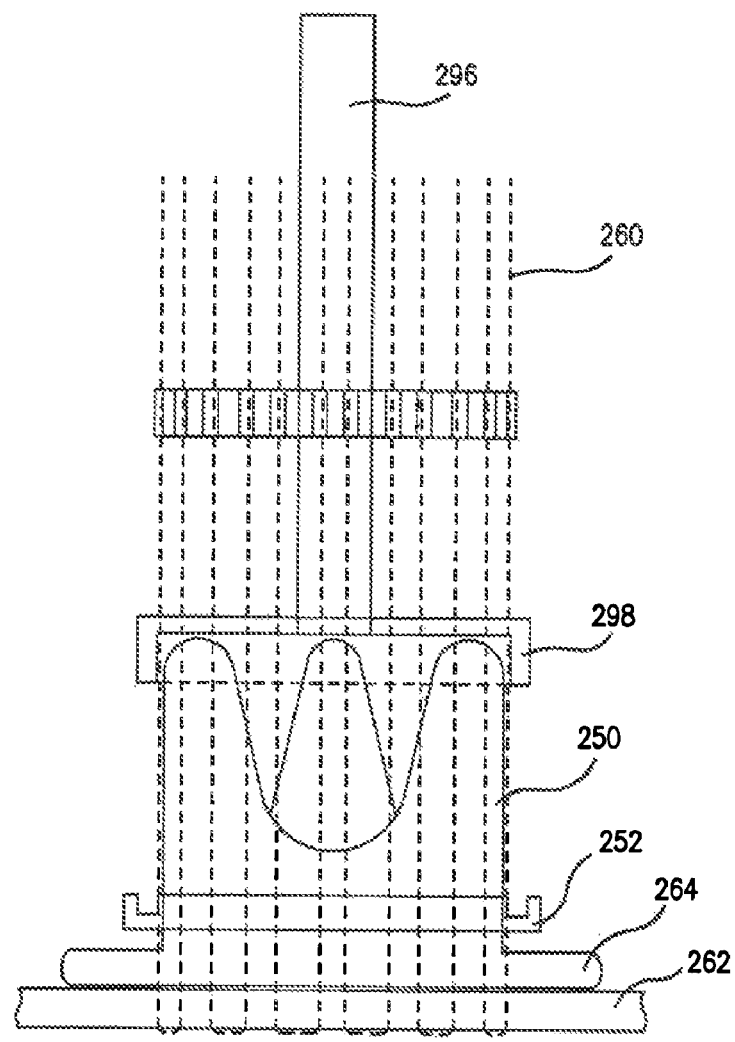
FIG. 30a is a plan schematic view of the valve of FIG. 25a including a valve holder tool and a suture tensioning tool.
Figure 30B:
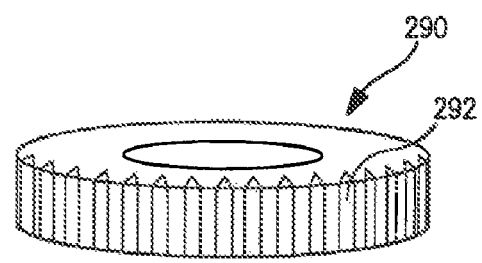
Figure 31:
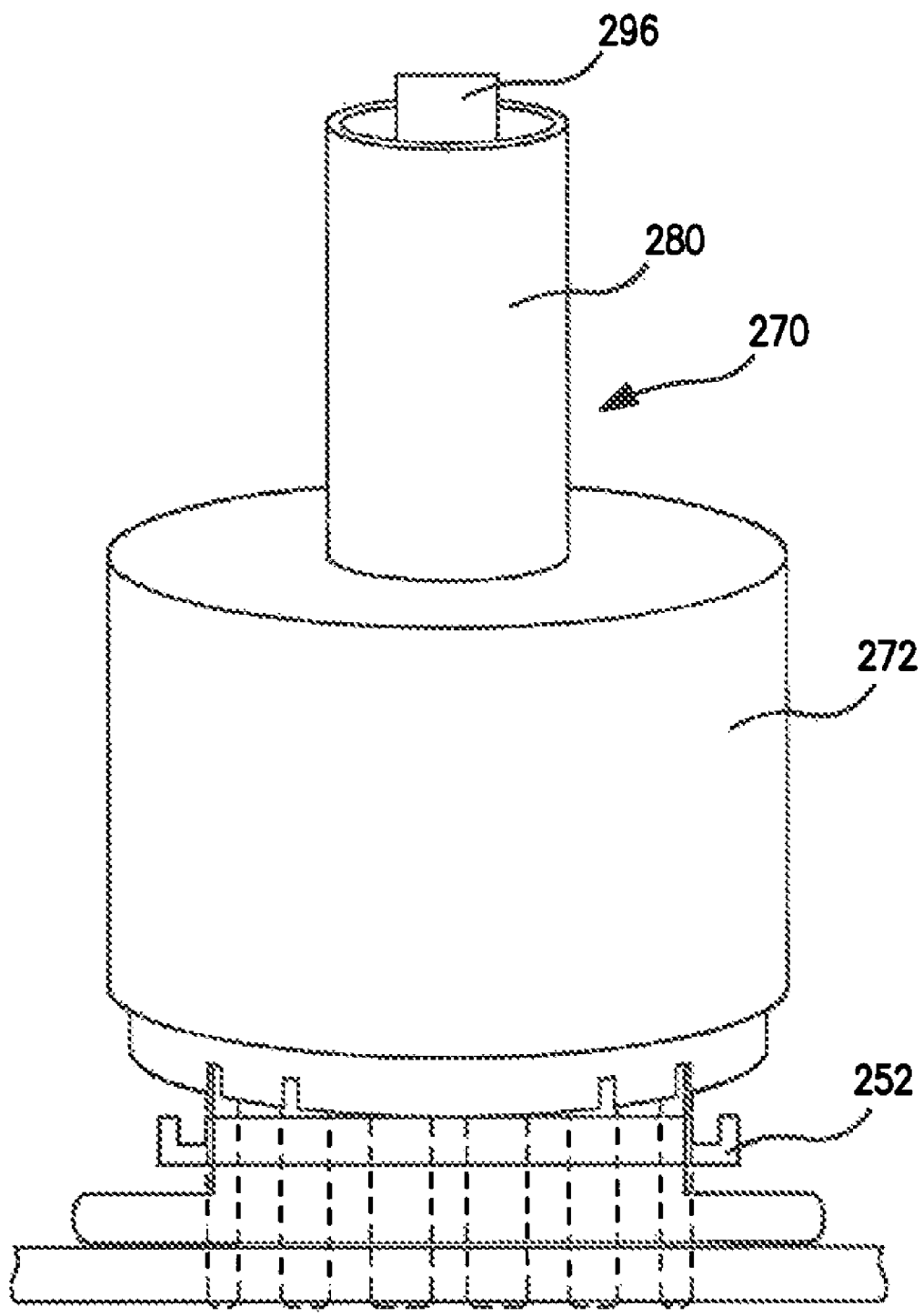

The process for pressing the band 220 onto the frame portion 252 can be facilitated by using a suture tensioning tool 290 as set forth in FIGS. 30a-b and 31. The suture tensioning tool 290 is mounted to the handle 296 for the valve holder 298. The suture tensioning tool 290 includes notches 292 or other suture tensioning devices around its circumference. In operation, the valve 250 is secured by a plurality of sutures 260 to a prepared valvular rim 262 by bringing the sutures through a suture ring 264, through a portion of the valvular rim 262 and returning the suture through the suture ring 264. The ends of the sutures 260 extending away from the valvular rim 262 are drawn up to the suture tensioning tool 290 and are retained thereto in the notches 292. After each of the sutures 260 is secured in position on the suture retaining tool, with any slack in the sutures 260 removed, the band 220 and pressing tool 270 are advanced over the handle 296, suture tensioning tool 290 and valve 250. With the handle 296 of the valve holder 298 and the handle of the pressing tool held stationary in one hand of the surgeon, the surgeon turns the body 272 until the band 220 locks onto the frame portion 252. The tools 270, 290 can then be removed and any excess material can then be removed from the ends of the sutures 260.

Figure 32:
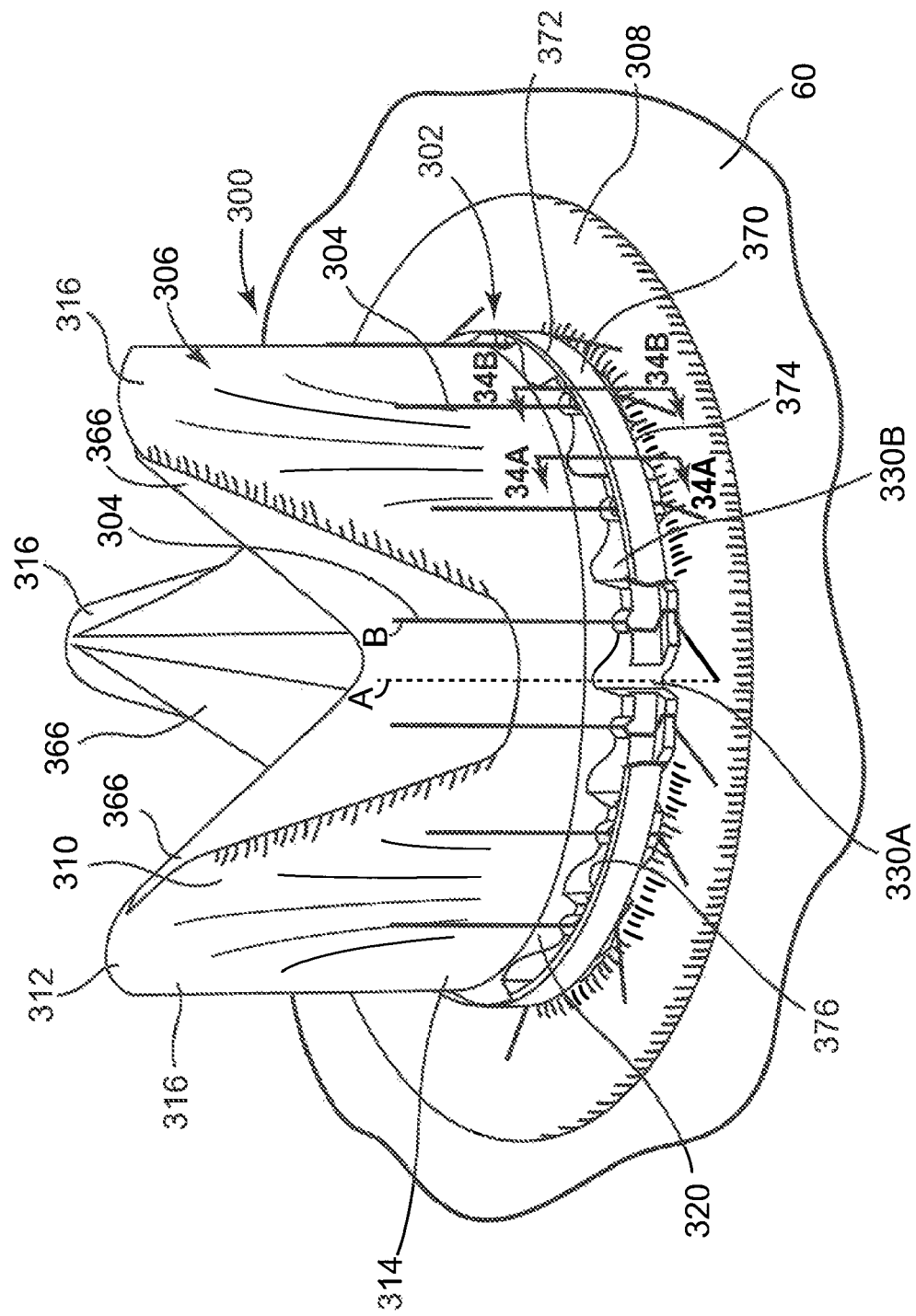
FIG. 32 is a perspective view of one embodiment of a heart valve mechanism with a suture locking assembly according to the present invention.

Other embodiments of the present invention related to a suture locking assembly for use with a heart valve repair device, such as prosthetic valve repair devices or annuloplasty repair devices (e.g., annuloplasty ring or band). For example, FIG. 32 illustrates a heart valve repair device, more particularly a heart valve mechanism 300, in conjunction with a suture locking assembly 302 positioned for attachment to the valvular rim 60. The suture locking assembly 302 is coupled with the heart valve mechanism 300 and is configured to receive each of a plurality of sutures 304, which are sewn through the valvular rim 60 in a first, unlocked position "A" and to maintain each of the sutures 304 in a second, locked position "B". When in the second position "B," the sutures 304 are tightly maintained by the suture locking assembly 302, thereby, securing the heart valve mechanism 300 to the valvular rim 60.

The heart valve mechanism 300 is a tissue valve mechanism and includes a valve frame or, more precisely, a fabric covered stent 306 and a sewing ring 308. In a similar manner as described above with respect to the stent 40, the fabric covered stent 306 includes a wire, plastic, or reinforced pyrolytic carbon stent frame 310 (generally indicated) substantially covered with a stent fabric 312. The stent frame 310 includes a cylindrical frame base 314 (generally indicated) and a plurality of frame posts 316 (generally indicated) spaced from one another and similarly extending from the cylindrical frame base 314. Notably, although the heart valve mechanism 300 is described and illustrated as a tissue valve mechanism, in other embodiments, the heart valve mechanism 300 could also be a mechanical heart valve mechanism similar to that illustrated in FIGS. 6 and 7 including a sewing ring or cuff (not shown).

As illustrated in FIGS. 33 and 33a, in one embodiment, the stent 306 additionally defines an annular rim 320 opposite the frame posts 316. The rim 320 defines a rim wall 322, a first or outflow flange 324, and a second or inflow flange 326. The rim wall 322 extends circumferentially around the frame base 314. The outflow flange 324 extends outwardly from and circumferentially around the rim wall 322 relatively near the frame posts 316. The inflow flange 326 extends outwardly from and circumferentially around the rim wall 322 opposite the outflow flange 324 near the sewing ring 308. As such, a circumferential groove 328 is defined by the rim wall 322, the outflow flange 324, and the inflow flange 326. In one embodiment, the outflow flange 324 extends outwardly from the rim wall 322 further than the inflow flange 326 extends outwardly from the rim wall 322. Note, that directional terminology, such as "outwardly," "inwardly," "up," "down," etc., is used with reference to the orientation of the Figure(s) being described for purposes of illustration only and is in no way limiting.

The rim 320 forms a plurality of recesses 330 spaced circumferentially and periodically about the rim 320. Each recess 330 laterally extends through the rim 320, more particularly, through the outflow flange 324, the inflow flange 326, and at least partially through the rim wall 322 to define a first lateral edge 332 and a second lateral edge 334 opposite the first lateral edge 332. In one embodiment, there are twenty-four recesses 330 evenly spaced around the rim 320, although other numbers are equally acceptable. The recesses 330 divide the rim 320, and therefore, the flanges 324 and 326 and the rim wall 322, into a plurality of segments 336. In particular, where adjacent segments 336 are considered to be a segment 336A and a segment 336B, as illustrated in FIG. 33a, the first lateral edge 332 of the recess 330 indicates the end of the segment 336A and the beginning of the adjacent segment 336B of the rim 320. Each of the segments 336 is similarly joined lateral edge-to-lateral edge to define the rim 320.

As illustrated in detail FIG. 33a, in the segment 336B, the outflow flange 324 includes a leading surface 340, a stop site 342, a stop surface 344, and a return surface 346. Considering the adjacent recesses 330 to be a recess 330A and a recess 330B, as illustrated in FIG. 33a, the leading surface 340 extends from the second lateral edge 334 of a recess 330A progressively outwardly to and circumferentially towards the adjacent recess 330B, terminating at the stop site 342 opposite the rim wall 322. In one embodiment, the stop site 342 is a groove or notch having a diameter or outside dimension larger than one of the sutures 304. The stop surface 344 extends circumferentially from the stop site 342 opposite the leading surface 340. In one embodiment, the stop surface 344 is positioned further from the rim wall 322 than the leading surface 340 is positioned from the rim wall 322. The return surface 346 extends inwardly from the stop surface 344 opposite the stop site 342 to the first lateral edge 332 of the adjacent recess 330B and, therefore, to the next segment 336.

Similarly, in the segment 336B the inflow flange 326 includes a leading surface 350, an outer surface 352, and a return surface 354. The leading surface 350 extends progressively outwardly from the recess 330A and circumferentially towards the adjacent recess 330B. The outer surface 352 extends circumferentially from the leading surface 350 opposite the recess 330 towards the adjacent recess 330B. The return surface 354 extends inwardly from the outer surface 352 opposite the leading surface 350 to the first lateral edge 332 of the adjacent recess 330B and, therefore, to the next segment 336. Notably, both the outflow flange 324 and the inflow flange 326 extend outwardly past an outer surface 356 of the rim wall 322, which circumferentially extends between each recess 330. As such, the outflow flange 324, the inflow flange 326, and the outer surface 356 collectively define the circumferential groove 328 there between. Each of the segments 336 is formed similar to the segment 336B described above.

Figure 33B:
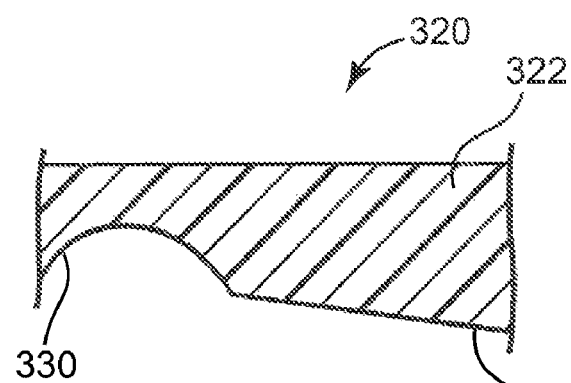
FIG. 33b is a cross-sectional view of one embodiment of the flange of FIG. 33 taken along the line X-X.
Figure 33C:
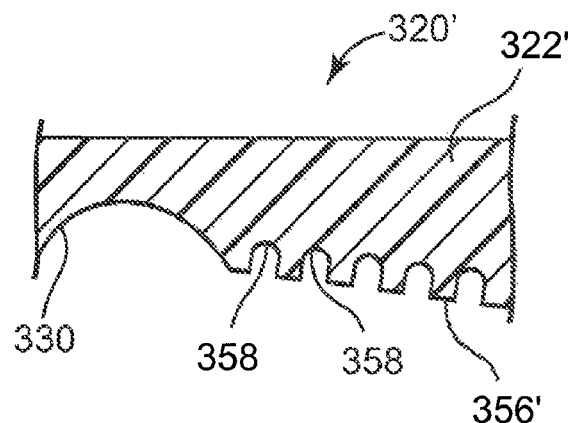
FIG. 33c is a cross-sectional view of another embodiment of the flange of FIG. 33 taken along the line X-X.
Figure 33D:
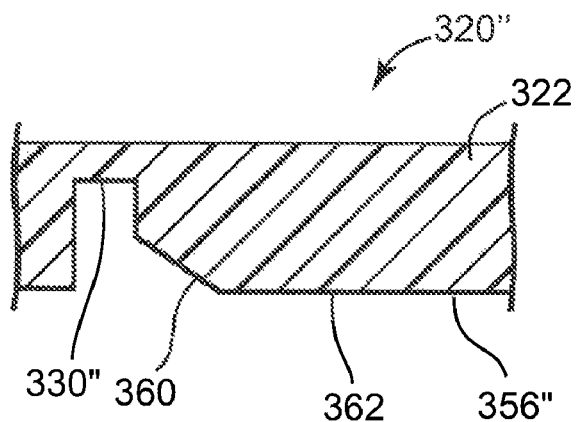
FIG. 33d is a cross-sectional view of another embodiment of the flange of FIG. 33 taken along the line X-X.

As illustrated in the cross-sectional views of FIGS. 33b-33d taken along the line of X-X of FIG. 33, the recess 330 and the outer surface 356 can be formed in a variety of manners. In one embodiment, illustrated in the cross-sectional view of FIG. 33b, the recess 330 is rounded to receive one of the sutures 304 (FIG. 32). The outer surface 356 extends from the recess 330 in a progressively outward manner relative a center (not shown) of the heart valve mechanism 300. In this embodiment, the outer surface 356 of the rim wall 322 is a relatively smooth surface. Alternatively, as illustrated in the cross-sectional view of FIG. 33c, an alternative rim 320' includes a rim wall 322' that forms an outer surface 356', which is a relatively rough surface forming multiple indentations 358. In yet another embodiment, as illustrated in the cross-sectional view of FIG. 33d, an alternative rim 320" forms a recess 330" that is relatively rectangular in cross-section. The rim wall 322" forms a rim wall surface 356", which extends in two sections from the recess 330". In particular, the rim wall surface 356" includes a first section 360 and a second section 362. The first section 360 extends progressively outwardly and circumferentially from the recess 330" to the second section 362. The second section 362 uniformly extends circumferentially from the first section 360 opposite the recess 330". Other embodiments of the recess 330 and rim wall surface 356 will be apparent to those of ordinary skill in the art. Preferably, each of the segments 336 of the rim 320 is similarly formed.

Referring again to FIGS. 32 and 33, the stent fabric 312 covers the stent frame 310 entirely except for the rim 320. In one embodiment, the stent fabric 312 is attached to the stent frame 310 by sutures (not shown). In one embodiment, the stent fabric 312 is a fabric made of a synthetic fiber, such as polytetrafluoroethylene (PTFE), polyester (e.g., polyethylene terephthalate (PET)), or acetyl homopolymer of a mesh weave having interstices permeable to tissue growth.

The sewing ring 308 is attached around and extends outwardly from the bottom of the fabric covered stent 306, namely the bottom of the frame base 314 adjacent the rim 320. In one embodiment, the sewing ring 308 is formed of a material similar to the stent fabric 312 and is sutured to the frame base 314. The sewing ring 308 outwardly extends from the frame base 314 a distance further than a distance the rim 320 extends from the frame base 314. Three occluders, more precisely, three flexible valve leaflets 366 are secured to and extend between the frame posts 316 of the stent frame 310 in a manner apparent to one of ordinary skill in the art, such as by sutures.

The suture locking assembly 302 includes the rim 320 and a suture band 370, illustrated in FIG. 32. The suture band 370 is a relatively rigid, closed ring sized to be tightly maintained within the circumferential groove 328. Notably, the suture band 370 is illustrated with a broken section (i.e., non-closed section) for illustrative purposes only. The suture band 370 includes an outflow side 372 and an inflow side 374 as illustrated in FIGS. 34a and 34b taken along the lines A-A and B-B, respectively. The distance between the outflow side 372 and the inflow side 374 is substantially similar to the height of the rim wall 322 between the outflow flange 324 and the inflow flange 326. In addition, an inner surface 376 of the suture band 370 has a diameter just slightly larger than the diameter of the outer surface 356 of the rim wall 322. In one embodiment, the suture band 370 is formed of a biocompatible, anti-thrombogenic material. In one embodiment, the suture band 370 is formed of any metallic material. In a preferred embodiment, the suture band 370 is formed of titanium, stainless steel, or other metal alloy.

As illustrated in FIG. 32 and the cross-sectional views of FIGS. 34a and 34b taken about the lines 34A-34A and 34B-34B, respectively, during assembly, the suture band 370 is placed within the circumferential groove 328 such that the outflow side 372 interacts with the outflow flange 324 of the rim 320 and the inflow side 374 interacts with the inflow flange 326 of the rim 320. Note that in FIGS. 34a and 34b, the gap between the suture band 370 and the rim 320 is greatly exaggerated for illustrative purposes. More specifically, although illustrated with a gap, the outflow side 372 and the outflow flange 324, the inner surface 376 of the suture band 370 and the outer surface 356 of the rim wall 322, and the inflow side 374 and the inflow flange 326 abut or nearly abut one another upon assembly. Most preferably, the suture band 370 is coupled with the rim 320 of the heart valve mechanism 300 prior to implantation within a patient (not shown).

Referring collectively to FIGS. 32, 34a, and 34b, during surgery, after the heart annulus (not shown) including the valvular rim 60 is cleaned, the sutures 304 are sewn through the valvular rim 60. More specifically, each suture 304 is sewn through the valvular rim 60 and back up through the valvular rim 60 to form two suture segments (one into and one out of the valvular rim 60). Preferably, the segments of the sutures 304 are spaced around the valvular rim 60 to mimic the spacing of the recesses 330 around the rim 320.

Upon initial placement of the sutures 304, the heart valve mechanism 300 with the suture locking assembly 302 is placed within the heart valve replacement patient (not shown). In particular, the heart valve mechanism 300 is placed upon the valvular rim 60 such that the sewing ring 308 at least partially extends over the material of the valvular rim 60 about the entire perimeter of the valvular rim 60, and the sewing ring 308 is positioned between the suture locking assembly 302 and the valvular rim 60. Upon positioning of the heart valve mechanism 300 with the suture locking assembly 302, a surgeon (not shown) pulls each segment of the sutures 304 through the sewing ring 308 and a corresponding recess 330 of the suture locking assembly 302. With this in mind, after pulling each segment of the sutures 304 through the sewing ring 308 and a corresponding recess 330, a single suture 304 extends down through the recess 330A, through the sewing ring 308, and into the valvular rim 60. More preferably, the same suture 304, described in the previous sentence, extends back out of the valvular rim 60, through a new area of the sewing ring 308, and up through the adjacent recess 330B. The process of sewing the sutures 304 through the sewing ring 308 and recesses 330 is repeated until each of the recesses 330 houses a single segment of the suture 304. As such, in one embodiment, twenty-four segments of the suture 304 (i.e. twelve lengths of suture 304) are inserted into the valvular rim and through the suture locking assembly 302 that has twenty-four recesses 330.

Upon placement of an individual suture 304 through an individual recess 330, the suture 304 is loosely maintained within the recess 330, more particularly, between the inner surface 376 of the suture band 370 and an outer surface 378 of the recess 330. Since each suture 304 is loosely maintained between the inner surface 376 and an outer surface 378 of the recess 330, the position of the heart valve mechanism 300 can be slightly adjusted with respect to the valvular rim 60 after each of the sutures 304 is in place. In one embodiment, the heart valve mechanism 300 with the suture locking assembly 302 is spaced from the valvular rim 60 during suturing and is slid along the sutures 304 to the valvular rim 60 following positioning of each of the sutures 304 through the suture locking assembly 302, the sewing ring 308, and the valvular rim 60.

In order to secure the heart valve mechanism 300 to the valvular rim 60, each of the sutures 304 is pulled by a surgeon (not shown) from the original or insertion position "A" as illustrated in FIGS. 32 and 34a to the second or locked position "B" as illustrated in FIGS. 32 and 34b. More particularly, each suture 304 is pulled from position "A" within the recess 330 to position "B" within the stop site 342 of the respective segment 336. With additional reference to FIG. 33, while being pulled toward position "B," each suture 304 is slid along the leading surface 340 of the outflow flange 324 and the leading surface 350 of the inflow flange 326 to the stop site 342 and to and at least partially along the outer surface 352 of the inflow flange 326. While sliding upon the leading surfaces 340 and 350, the suture 304 eventually contacts the inner surface 376 of the suture band 370. Upon contacting the inner surface 376, the suture 304 is forced within the circumferential groove 328, as best illustrated in FIG. 34b. More particularly, the suture 304 is pulled between the suture band 370 and the rim 320 of the suture locking assembly 302.

In particular, the suture 304 extends between the outflow flange 324, the rim wall outer surface 356, and the inflow flange 326 of the rim 320 and the outflow side 372, the inner surface 376, and the inflow side 374 of the suture band 370, respectively. As such, the suture band 370 is sized within the circumferential groove 328 such that the outflow flange 324 and the inflow flange 326 closely interact with the outflow side 372 and the inflow side 374 of the suture band 370, respectively, to pinch the suture 304 in place, thereby securing the suture 304 within the suture locking assembly 302. Securing the sutures 304 to the suture locking assembly 302 also secures the heart valve mechanism 300 to the valvular rim 60. Notably, locked position "B" is located at least partially along an outer periphery or external boundary of the rim 320.

The process of transitioning the suture 304 from position "A" to position "B" is repeated for each of the sutures 304 in the respective segments 336. Upon transitioning each of the sutures 304 to position "B," each of the sutures 304 can be trimmed near the suture locking assembly 302, and the excess portion of each of the sutures 304 discarded. Notably, since the suture 304 is tightly maintained within the suture locking assembly 302, the method of attaching the heart valve mechanism 300 to the valvular rim 60 is characterized by the absence of suture knots.

In one embodiment, the surgeon (not shown) may utilize a suture holder 380 as illustrated in FIG. 35 to facilitate transitioning of each suture 304 from position "A" to position "B." In one embodiment, the suture holder 380 includes a handle 382 and an interface plate 384. The interface plate 384 is coupled with a distal end 386 of the handle 382. The handle 382 serves as an extension of the surgeon. The interface plate 384 provides a surface or edge 388 to selectively interact with each suture 304 upon manipulation of the handle 382 by the surgeon to transition the suture 304 from position "A" to position "B" (FIG. 32). Notably, other suture holder embodiments will be apparent to those of ordinary skill in the art. Furthermore, in one embodiment, the surgeon does not utilize the suture holder 380 during the implant surgery.

FIGS. 36 and 36a illustrate another embodiment in accordance with the present invention including a heart valve mechanism 300' with a suture locking assembly 302'. Notably, the heart valve mechanism 300' and the suture locking assembly 302' are similar to the heart valve mechanism 300 and the suture locking assembly 302 described above and illustrated in FIGS. 32-34b except for the differences enumerated herein. The heart valve mechanism 300' includes a fabric covered stent 306' that defines a rim 320'. The rim 320' defines a circumferential rim wall 322', an outflow flange 324', and an inflow flange 326'.

The outflow flange 324' and the inflow flange 326' extend from the circumferential rim wall 322' in a manner similar to that described with respect to the outflow flange 324, the inflow flange 326, and the circumferential rim wall 322. Similarly, the rim 320' defines a plurality of recesses 330' circumferentially and periodically spaced about the rim 320'. Each recess 330' laterally extends through the outflow flange 324', the inflow flange 326' and at least partially through the circumferential rim wall 322'. In one embodiment, the rim 320' defines twelve recesses 330', including the recesses 330A', 330B', and 330C' in which the recesses 330A' and 330C' flank the recess 330B', although other numerals are equally acceptable. Each recess 330', in particular recess 330B', defines a first lateral edge 332', with the lateral edge 332' of adjacent recesses 330' defining the boundary of the segment 336' disposed there between. For example, as illustrated in FIG. 36a, a segment 336A' extends between the lateral edge 332' of the recess 330A' and the lateral edge 332' of the recess 330B'.

The outflow flange 324' of each segment 336' defines a leading surface 390, an outer surface 392, and a return surface 394. With respect to the segment 336A, the leading surface 390 extends from the recess 330A' opposite the first lateral edge 332' progressively outwardly and circumferentially towards the recess 330B'. The outer surface 392 extends from the leading surface 390 opposite the recess 330A' in a circumferential manner. The return surface 394 extends from the outer surface 392 opposite the leading surface 390 circumferentially towards the first lateral edge 332' of the adjacent recess 330B'.

Similarly, the inflow flange 326' includes a leading surface 402, an outer surface 404, and a return surface 406. The leading surface 402, the outer surface 404, and the return surface 406 extend between neighboring recesses 330' in a similar manner as described with respect to the leading surface 390, the outer surface 392, and the return surface 394 of the outflow flange 324'. However, the outer surface 404 of the inflow flange 326' includes a first stop site 408 and a second stop site 410 spaced circumferentially from the first stop site 408. Each of the stop sites 408 and 410 extend inwardly from the remainder of the outer surface 404 as a V-cutout or notch. In one embodiment, the stop sites 408 and 410 have an outer dimension sized to accommodate a suture 304 as will be described further below.

The rim wall 322' defines an outer surface 356' extending between the outflow flange 324' and inflow flange 326' in a similar manner as described above with respect to the outer surface 356. The suture band 370 is assembled with the rim 320' in a similar manner as described above with respect to the rim 320. The rim 320' and the suture band 370 collectively form the suture locking assembly 302'.

During surgery, a plurality of sutures are sewn around the valvular rim in a manner corresponding with the spacing of the recesses 330' around the rim 320', which will become more apparent below. After sewing the sutures 304 through the valvular rim 60, the heart valve mechanism 300' is aligned with the valvular rim 60, such that the sewing ring 308 is positioned between the suture locking assembly 302' and the valvular rim 60. Individual sutures 304 extending from the valvular rim 60 are sewn through the sewing ring 308 and to respective ones of the segments 336' through the corresponding recesses 330'. For example, upon placement of the sutures 304 through the corresponding recesses 330', a suture 304A extends through the recess 330A', through the sewing ring 308, into, through, and out of the valvular rim 60, and up through the adjacent recess 330B'. Similarly, another suture 304 extends into the recess 330B', through the valvular rim 60, and out the recess 330C'.

Using this technique, the suture 304A defines a first suture segment $304A_1$, extending into the valvular rim 60 and a second suture segment $304A_2$ extending out of the valvular rim 60. In one embodiment, the suture segments $304A_1$ and $304A_2$ are crisscrossed between exiting the sewing ring 308 and entering the recesses 330A' and 330B', respectively. This method of suturing the heart valve mechanism 300' to the valvular rim 60 is repeated for each of the recesses 330'. As described above, following insertion of each of the sutures 304 through the respective recesses 330', the heart valve mechanism 300' is positioned more precisely with respect to the valvular rim 60.

Upon proper positioning of the heart valve mechanism 300' with respect to the valvular rim 60, a surgeon (not shown) pulls or transitions each of the sutures 304 from a first or inserted position into a second or locked position. For example, the surgeon selects the sutures segment $304A_1$ within the recess 330A' and pulls or transitions the suture segment $304A_1$ along the leading surface 390 of the outflow flange 324' and the leading surface 402 of the inflow flange 326' towards and over the respective outer surfaces 392 and 404 of the segment 336' (i.e., towards the recess 330B'). Preferably, the suture segment $304A_1$ is pulled along the outer surfaces 392 and 404, a distance sufficient to cross the first stop site 408. Upon transitioning of first suture 304A to the locked position "D," the first suture segment $304A_1$ is tightly secured between the suture band 370 and the circumferential groove 328' of the rim 320', similarly as described above with respect to the rim 320.

After positioning the suture segment $304A_1$ in the locked position "D," the surgeon (not shown) selects the suture segment $304A_2$ from within the adjacent recess 330B'. The suture segment $304A_2$ is pulled or transitioned away from the recess 330B', in particular, from a first position "E," in the opposite direction as the suture segment $304A_1$. Otherwise stated, the suture segment $304A_2$ is pulled towards the recess 330A'. As such, the suture segment $304A_2$ is pulled along the return surface 394 of the outflow flange 324' and the return surface 406 of the inflow flange 326' of the adjacent segment 336'. Preferably, the suture segment $304A_2$ is pulled over the outer surfaces 392 and 404 of the outflow flange 324' and the inflow flange 326', respectively, until the suture segment $304A_2$ crosses over the second stop site 410 of the outer surface 404 of the segment 336' to a locked position "F". The suture segment $304A_2$ is securely maintained between the suture band 370 and the circumferential groove 328' of the rim 320'. In one embodiment, the suture segments $304A_1$ and $304A_2$ are simultaneously pulled to the respective locked positions "D" and "F." Notably, the locked positions "D" and "F" of the suture segments 304A₁ and 304A₂ are each at least partially defined along an outer periphery or external boundary of the rim 320'.

The process of transitioning the suture segments 304A₁ and 304A₂ from the first position "C" or "E" to the locked position "D" or "F" is repeated for each of the sutures 304. Once again, upon transitioning each of the suture segments 304A₁ and 304A₂ to a locked position "D" or "F," each suture 304 is trimmed and the excess suture material discarded. Also as described above, the surgeon (not shown) may choose to use a suture holder 380 (FIG. 35) to facilitate transitioning of each suture segment 304A₁ and 304A₂ from position "C" or "E" to position "D" and "F." When all sutures 304 are locked in position D or F, the heart valve mechanism 300' is secured to the valvular rim 60. Notably, since each of the sutures 304 is secured within the suture locking assembly 302', the method of attaching the heart valve mechanism 300' to the valvular rim 60 is characterized by the absence of suture knots.

FIGS. 37 and 37a illustrate another embodiment in accordance with the present invention including a heart valve mechanism 300" with a suture locking assembly 302". Notably, the heart valve mechanism 300" and the suture locking assembly 302" are similar to the heart valve mechanism 300' and the suture locking assembly 302' described above and illustrated in FIGS. 36 and 36a except for the differences enumerated herein. The heart valve mechanism 300" includes a fabric covered stent 306" that defines a rim 320". The rim 320" defines a circumferential rim wall 322", an outflow flange 324", and an inflow flange 326".

The outflow flange 324" and the inflow flange 326" extend from the rim wall 322" in a manner similar to that described with respect to the outflow flange 324', the inflow flange 326', and the rim wall 322'. Similarly, the rim 320" defines a plurality of recesses 330" circumferentially and periodically spaced about the rim 320". Each recess 330" laterally extends through the outflow flange 324", the inflow flange 326" and at least partially through the rim wall 322". In one embodiment, the rim 320" defines twelve recesses 330" including the adjacent recesses 330A' and 330B", although other numbers are equally acceptable. Each recess 330", in particular the recess 330A", defines a first lateral edge 332", with the lateral edge 332" of adjacent recesses 330" defining the boundary of the segment 336" disposed therebetween. For example, as illustrated in FIG. 37a, a segment 336A" extends between the lateral edges 332" of the recesses 330A' and 330B'.

The outflow flange 324" of each segment 336" defines a leading surface 390", an outer surface 392", and a return surface 394". With respect to the segment 336A", the leading surface 390" extends from the recess 330A" opposite the first lateral edge 332" progressively outwardly and circumferentially towards the recess 330B". The outer surface 392" extends from the leading surface 390" opposite the recess 330A" circumferentially towards the recess 330B". The outer surface 392" of the outflow flange 324" includes a stop site 420. The stop site 420 is an elongated notch that extends inwardly from the remainder of the outer surface 392". The return surface 394" extends from the outer surface 392" opposite the leading surface 390" circumferentially and progressively inwardly towards the first lateral edge 332" of the adjacent recess 330B".

Similarly, the inflow flange 326" includes a leading surface 402", an outer surface 404", and a return surface 406". The leading surface 402", the outer surface 404", and the return surface 406" extend between neighboring recesses 330" in a similar manner as described with respect to the leading surface 390", the outer surface 392", and the return surface 394" of the outflow flange 324". However, the outer surface 404" of the inflow flange 324" includes a stop tab 422 rather than the stop site 420. The stop tab 422 is an elongated tab that extends outwardly from the remainder of the outer surface 404". In one embodiment, the stop tab 422 has a length and a position along the outer surface 404" of the inflow flange 326" in a similar manner as the stop site 420 has a length and a position along the outer surface 392" of the outflow flange 324"

The rim wall 322" defines an outer surface 356" extending between the outflow flange 324" and inflow flange 326". The suture band 370 is assembled to the rim 320" in a similar manner as described above with respect to the rims 320 and 320'. The rim 320" and the suture band 370 collectively form the suture locking assembly 302".

During use, a plurality of sutures are sewn around the valvular rim 60 in a manner corresponding with the spacing of the recesses 330" around the rim 320", which will become more apparent below. After sewing the sutures 304 through the valvular rim 60, the heart valve mechanism 300" is aligned with the valvular rim 60, such that the sewing ring 308 is positioned between the suture locking assembly 302" and the valvular rim 60. Individual sutures 304 extending from the valvular rim 60 are sewn through the sewing ring 308 and to respective ones of the segment's 336' through corresponding recesses 330'. For example, upon placement of the sutures 304 through the corresponding recesses 330", a suture 304A extends through the recess 330A", through the sewing ring 308, into, through, and out of the valvular rim 60, and up through the adjacent recess 330B".

Using this technique, the suture 304A defines a first suture segment 304A₁, extending into the valvular rim 60 and a second suture segment 304A₂ extending out of the valvular rim 60. In one embodiment, the suture segments 304A₁ and 304A₂ are crisscrossed between exiting the sewing ring 308 and entering the recesses 330A" and 330B", respectively. This method of suturing the heart valve mechanism 300" to the valvular rim 60 is repeated for each of the recesses 330". As described above, following insertion of each of the sutures 304 through the respective recesses 330", the heart valve mechanism 300" is positioned more precisely with respect to the valvular rim 60.

Upon proper positioning of the heart valve mechanism 300" with respect to the valvular rim 60, a surgeon (not shown) pulls or transitions each of the sutures 304 from a first or inserted position into a second or locked position. For example, the surgeon selects the suture segment 304A₁ from within the recess 330A" and pulls or transitions the suture segment 304A₁ from a first or inserted position "G" along the leading surface 390" of the outflow flange 324" and the leading surface 402" of the inflow flange 326" towards and over the respective outer surfaces 392" and 404" of the segment 336" towards the recess 330B". Preferably, the suture segment 304A₁ is pulled along the outer surfaces 392" and 404", a distance sufficient to enter the stop site 420 and move to a locked position "H". In transitioning to the locked position "H," the suture segment 304A₁ does not pass over the stop tab 422. Upon transitioning of the suture segment 304A₁ to position "H," the suture segment 304A₁ is tightly secured between the suture band 370 and the circumferential groove 328" of the rim 320", in a similar manner as described above with respect to the rims 320 and 320'.

The surgeon (not shown) also selects the suture segment 304A₂ from within the adjacent recess 330B". The suture segment 304A₂ is pulled or transitioned away from the recess 330B", in particular, from a first position "I," in the opposite direction as the suture segment 304A₁. Otherwise stated, the suture segment 304A₂ is pulled towards the recess 330A". As such, the second suture 304B is pulled along the return surface 394" of the outflow flange 324" and the return surface 406" of the inflow flange 326" of the adjacent segment 336". Preferably, the suture segment 304A$_2$ is pulled over the outer surfaces 392" and 404" of the outflow flange 324" and the inflow flange 326", respectively, until the suture segment 304A$_2$ enters into the stop site 420 and moves into a locked position "J". In transitioning to the locked position "J," the suture segment 304A$_2$ does not pass over the stop tab 422. The suture segment 304A$_2$ is securely maintained between the suture band 370 and the circumferential groove 328" of the rim 320". In one embodiment, the suture segments 304A$_1$ and 304A$_2$ are simultaneously pulled to the respective locked positions "H" and "J."

Figure 37C:
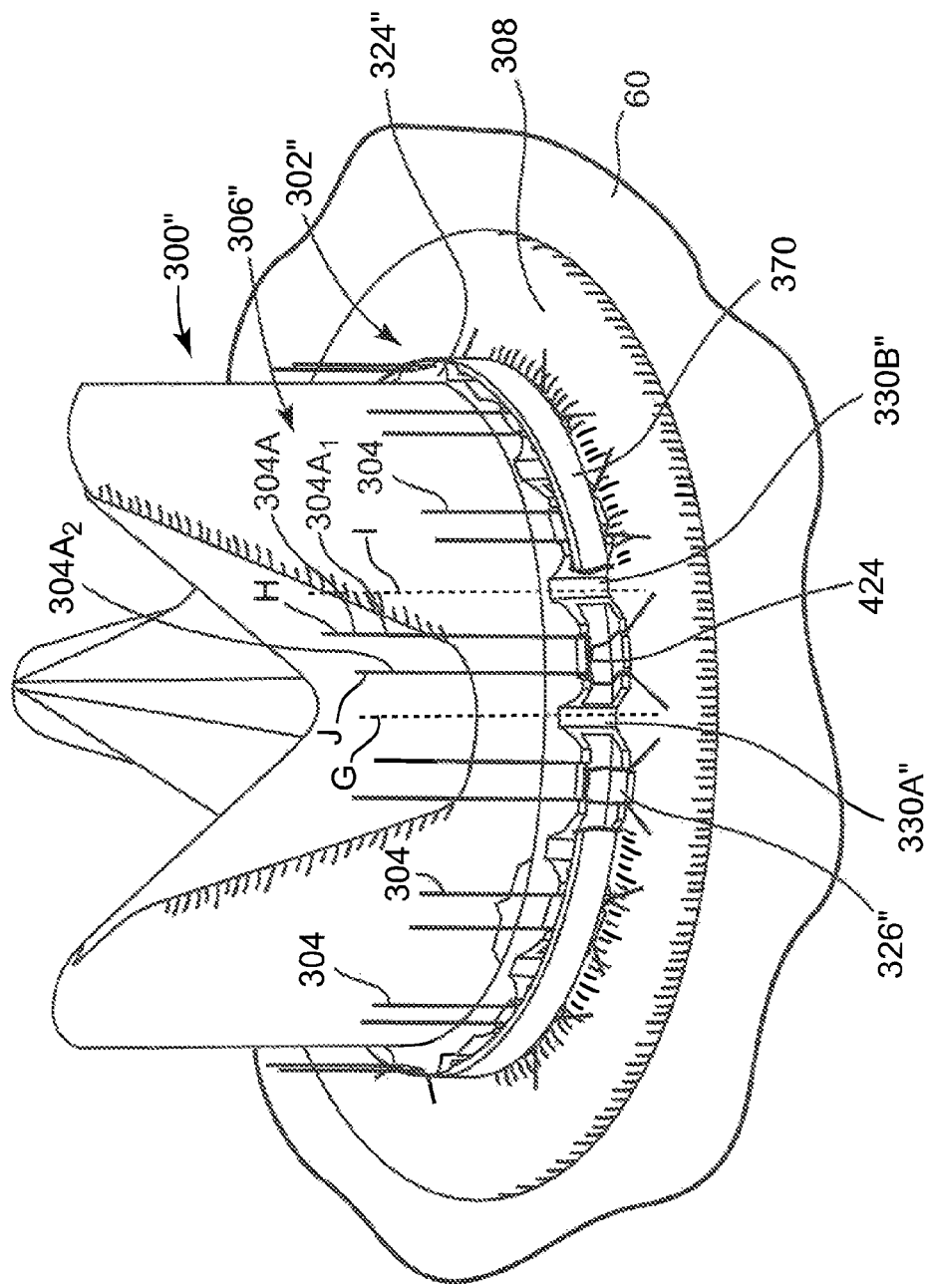
FIG. 37c is a perspective view of the heart valve mechanism with the suture locking assembly of FIG. 37 illustrating another embodiment of a suture technique.

In another embodiment, as illustrated in FIG. 37b, the suture segments 304A$_1$ and 304A$_2$ do not cross between exiting the sewing ring 308 and entering the recesses 330". In yet another embodiment illustrated in FIG. 37c, the suture segments 304A$_1$ and 304A$_2$ do not cross each other between exiting the sewing ring 308 and entering the recesses 330", in a similar manner as illustrated in FIG. 37b. However, after transitioning the suture segments 304A$_1$ and 304A$_2$ into the respective locked positions "H" and "J," the surgeon (not shown) manipulates the suture segments 304A$_1$ and 304A$_2$ to form a hitch 424 and pulls the suture segments 304A$_1$ and 304A$_2$ to position the hitch 424 between the outflow flange 324" and the suture band 370. In one embodiment, the hitch is a one half flat square knot. Notably, the locked positions "H" and "J" of the suture segments 304A$_1$ and 304A$_2$ are each at least partially defined along an outer periphery or external boundary of the rim 320".

The process of transitioning the suture segments 304A$_1$ and 304A$_2$ from the first position "G" or "I" to the locked position "H" or "J" is repeated for each of the sutures 304. Once again, upon transitioning of each of the suture segments 304A$_1$ and 304A$_2$ to the locked position "H" or "J," each suture segment 304A$_1$ and 304A$_2$ is trimmed and the excess suture material discarded. Also as described above, the surgeon (not shown) may chose to use a suture holder 380 (FIG. 35) to facilitate transitioning of each suture segment 304A$_1$ and 304A$_2$ from the first position "G" or "I" to the locked position "H" or "J." When all sutures 304 are in the locked position "H" or "J," the heart valve mechanism 300" is secured to the valvular rim 60. In one embodiment, since each of the sutures 304 is secured within the suture locking assembly 302", the method of attaching the heart valve mechanism 300" to the valvular rim 60 is characterized by the absence of suture knots. In other embodiments, the surgeon may knot the sutures 304 to further secure heart valve mechanism 300".

Figure 38:
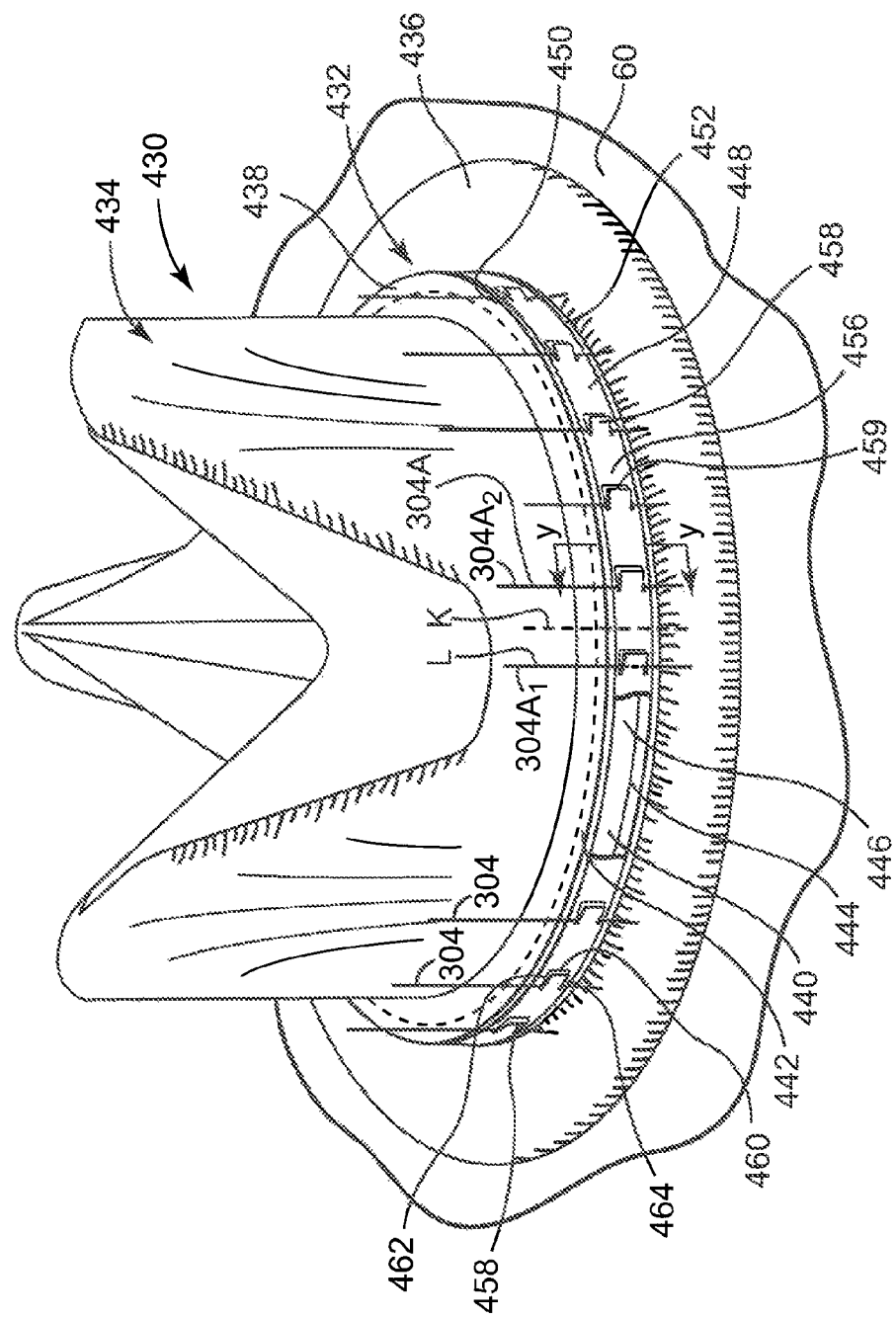
FIG. 38 is a perspective view of another embodiment of a heart valve mechanism with a suture locking assembly according to the present invention.
Figure 38A:
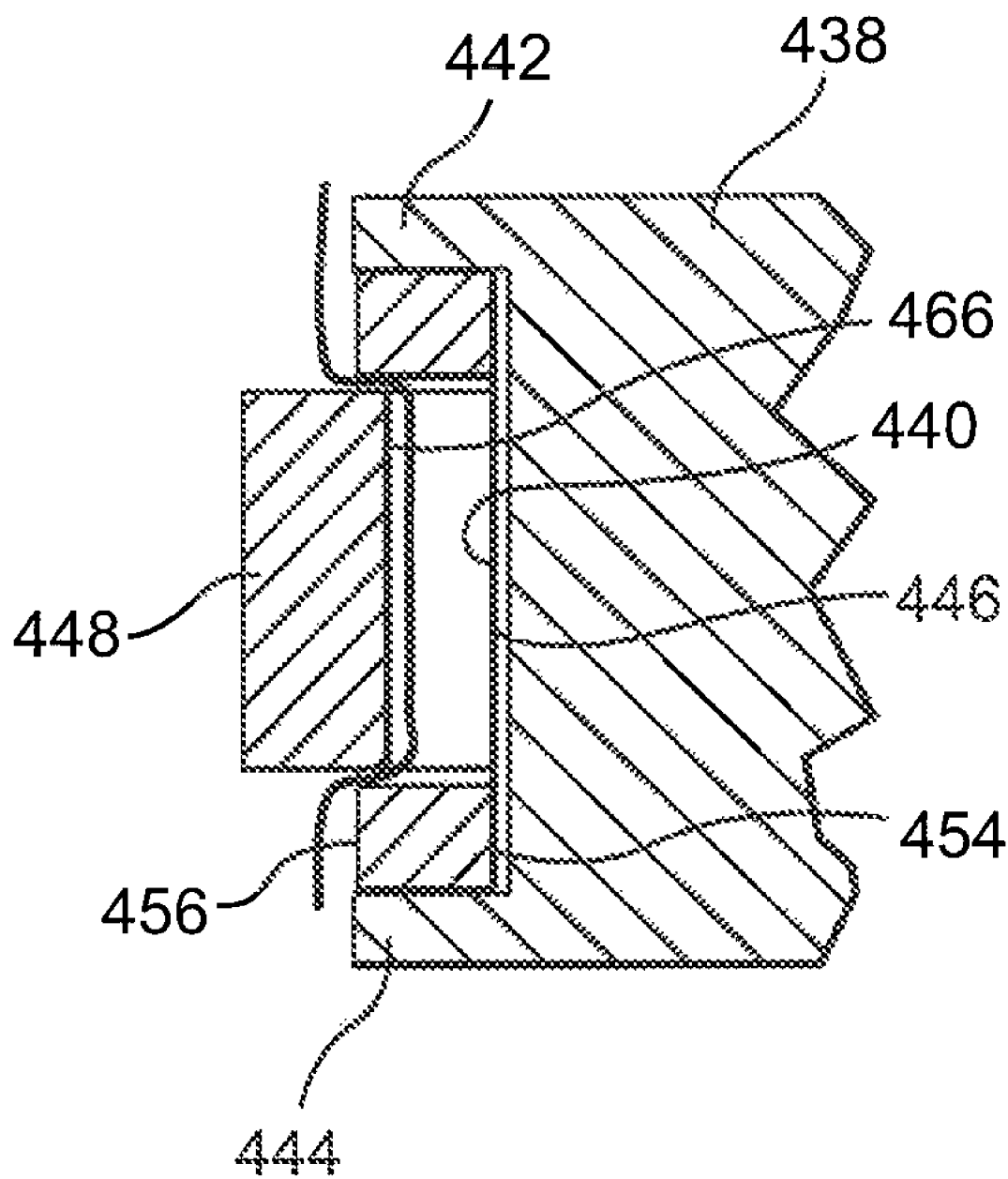
FIG. 38a is a cross-sectional view of the suture locking assembly of FIG. 38 taken along the line Y-Y.

FIGS. 38 and 38a illustrate another embodiment of the present invention including a heart valve mechanism 430 with a suture locking assembly 432. The heart valve mechanism 430 includes a fabric covered stent 434 and a sewing ring 436 in a similar manner as described above with respect to the heart valve mechanism 300 (FIG. 32) in all respects except those specifically numerated herein. The fabric covered stent 438 includes a rim 438 that defines a circumferential rim wall 440, an outflow flange 442, and an inflow flange 444. The rim wall 440 extends continuously and circumferentially around the rim 438. The outflow flange 442 extends from the rim wall 440 opposite the sewing ring 436 in a continuous and circumferential manner. Similarly, the inflow flange 444 extends from the rim wall 440 adjacent the sewing ring 436 in a continuous and circumferential manner. As such, a continuous and circumferential groove 446 is collectively defined by the rim wall 440, the outflow flange 442, and the inflow flange 444. The groove 446 is sized and shaped to receive a suture band 448. The combination of the suture band 448 with the rim 438 defines the suture locking assembly 432.

The suture band 448 is a relatively rigid, closed ring sized to be tightly maintained within the circumferential groove 446. In particular, the suture band 448 defines an outflow side 450, and inflow side 452 opposite the outflow side 450, an inner surface 454 (FIG. 38a), and an outer surface 456. The suture band 448 defines a plurality of tabs 458 spaced periodically about the suture band 448. Each tab 458 is defined with respect to the remainder of the suture band 448 by a U-shaped cut 459, mores specifically, a first cut 460, a second cut 462, and a third cut 464. The first cut 460 extends substantially perpendicular to the outflow side 450 and the inflow side 452 partially between each of the outflow side 450 and the inflow side 452. The second cut 462 extends from the first cut 460 relatively near the outflow side 450 in a manner substantially parallel with the outflow side 450. The third cut 464 extends from the first cut 460 opposite the second cut 462 in a manner substantially parallel with the inflow side 452.

The cuts 460, 462, and 464 are formed through and between both the inner surface 454 and the outer surface 456. With additional reference to FIG. 38a, each of the tabs 458 is bent to extend outwardly relative to the outer surface 456 of a remainder of the suture band 448 such that an inner surface 466 of the tab 458 is outwardly spaced from the inner surface 454 of the remainder of the suture band 448. In one embodiment, the suture band 448 is formed of a biocompatible, anti-thrombogenic material. In a preferred embodiment, the suture band 448 is formed of titanium, stainless steel, or other metal alloy. During assembly, the suture band 448 is positioned within the groove 446, thereby coupling the suture band 448 with the rim 438 to define the suture locking assembly 432. In one embodiment, the suture band 448 defines twenty-four tabs 458, although other numbers are equally acceptable.

During use, the heart valve mechanism 430 with the suture locking assembly 432 is placed within a patient (not shown) and preliminarily aligned with the valvular rim 60. A surgeon (not shown) sews a length of the suture 304 near respective ones of the first cuts 460 of the tabs 458 through the sewing ring 436 and the valvular rim 60 in position "K," and is sewn out the valvular rim 60, and the sewing ring 436 near the first cut 460 of an adjacent tab 458. In one embodiment, the sutures 304 are sewn through the valvular rim 60 before the heart valve mechanism 430 and the suture locking assembly 432 are placed within the patient. Upon sewing of each of the sutures 304, the heart valve mechanism 430 is more precisely aligned with respect to the valvular rim 60. For example, in FIG. 38, the suture 304A includes a first segment 304A$_1$ extending into the valvular rim 60 and a second segment 304A$_2$ extending out of the valvular rim 60.

Upon more precise alignment of the heart valve mechanism 430 with the valvular rim 60, a surgeon grasps the suture 304A in position "K" and pulls or transitions the suture 304A into the respective tab 458 away from the first cut 460 to a second or locked position "L". For example, the first segment 304A$_1$ is transitioned to behind the tab 458 to the locked position as show in FIG. 38. In particular, the suture segment 304A$_1$ is pulled between the inner surface 466 of the tab 458 and the inner surface 454 of the remainder of the rim wall 440 as illustrated in FIG. 38a to the locked position "L." As such, the suture segment 304A$_1$ is pinched within the second cut 462 and the third cut 464.

Upon transitioning of the suture segment 304A$_1$ to the locked position "L," the remainder of the suture segment 304A$_1$ (i.e., the portion of the suture segment 304A$_1$ extending beyond the outflow flange 442 of the rim 438) may be cut and discarded. Each of the sutures 304 is transitioned from the first position "K" to the locked position "L" as described above for the suture 304A. Notably, the locked position "L" of each of the sutures 304 is at least partially defined near, or more precisely, outwardly beyond, an outer periphery or external boundary of the rim 438 with respect to the center of the suture band 448.

Upon transitioning of each of the sutures to the locked position "L," each suture is tightly maintained within the respective tab 458. Notably, the suture band 448 is formed of a sufficiently rigid material so the tab 458 does not gradually pull away from the rim 438 to release the suture 304. Since each suture 304 is secured to the suture locking assembly 432, the heart valve mechanism 430 is also secured to the valvular rim 60. This method of securing the sutures 304 with the suture locking assembly 432 is characterized by an absence of suture knots.

Figure 39:
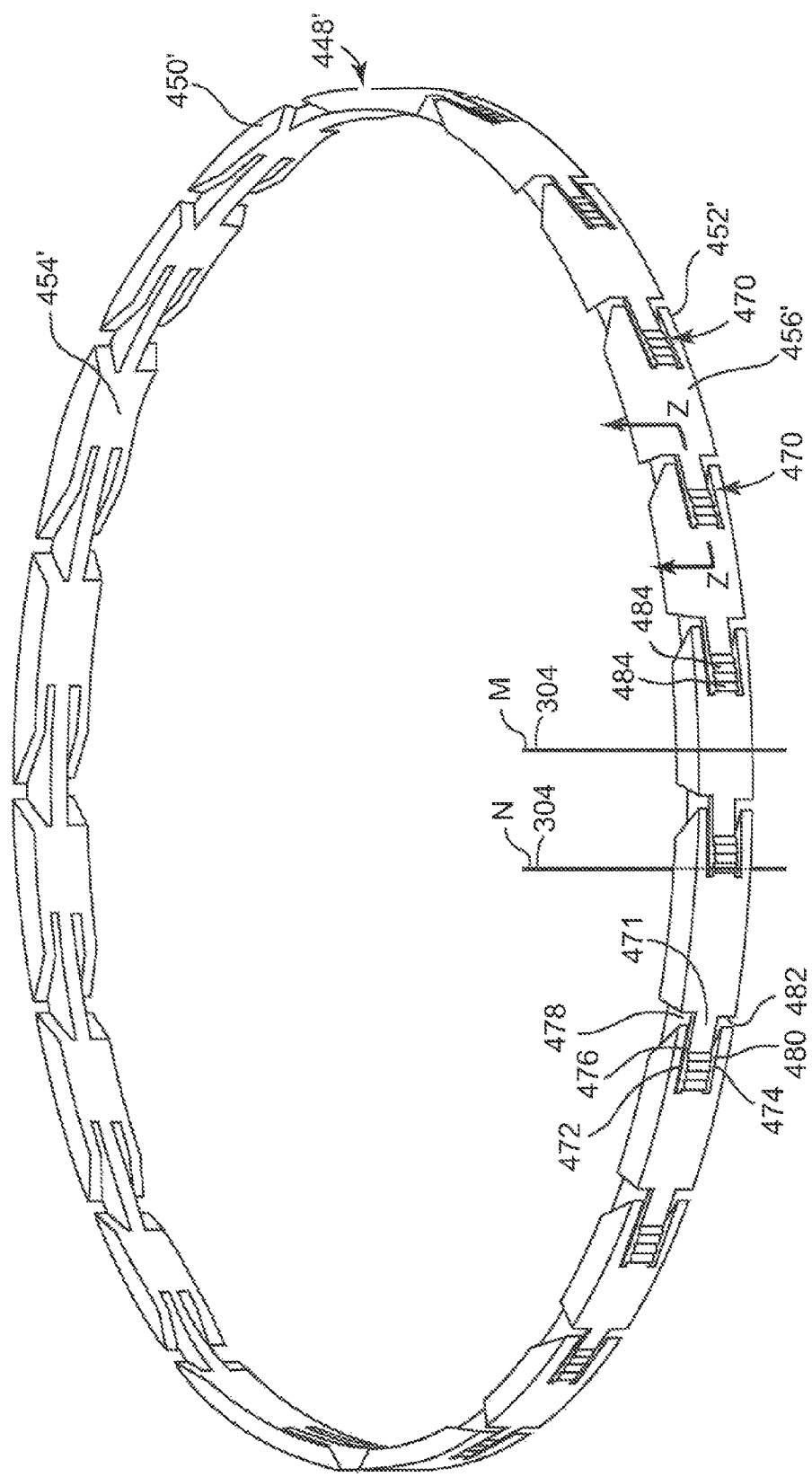
FIG. 39 is a perspective view of an alternative embodiment of a suture band or the suture locking assembly of FIG. 38.
Figure 39A:
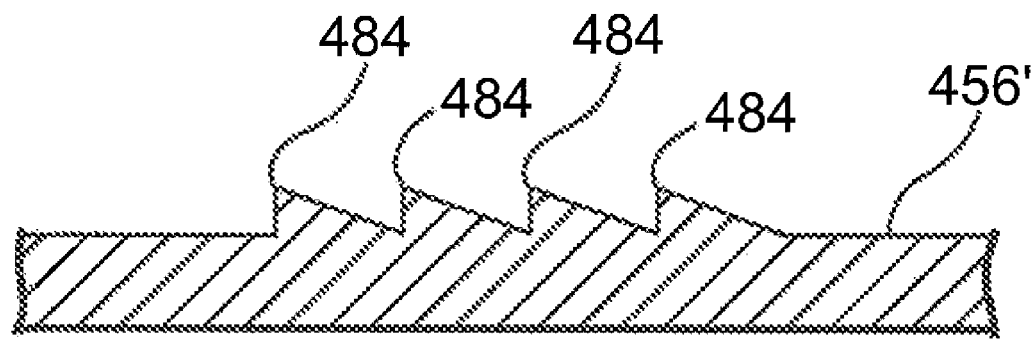
FIG. 39a is a cross-sectional view of the suture locking assembly of FIG. 39 taken along the line Z-Z.

Another embodiment of a suture band 448' for use with the rim 438 of the heart valve mechanism 430 is illustrated in FIG. 39, wherein the suture band 448' can replace the suture ring 448 (FIG. 38) in the suture locking assembly 432 (FIG. 38). The suture band 448' is a relatively rigid, closed ring sized to be tightly maintained within the circumferential groove 446 (FIG. 38) of the rim 438 (FIG. 38). The suture band 448' defines an outflow side 450', an inflow side 452', an inner surface 454', and an outer surface 456' similar to the outflow side 450, the inflow side 452, the inner surface 454, and the outer surface 456 of the suture band 448 (FIG. 38) described above except for the differences enumerated below. The suture band 448' defines a plurality of engagement sections 470 spaced periodically around the suture band 448'. Each engagement section 470 includes a connecting body 471 defined by a first, outflow side cut 472 and a second, inflow side cut 474. The first and second side cuts 472 and 474 are each formed entirely through the suture band 448', in other words, extend through the inner surface 454' and the outer surface 456' of the suture band 448' to define the connecting body 471 there between.

The first side cut 472 includes a longitudinal segment 476 and a lateral segment 478. The longitudinal segment 476 extends relatively near and parallel to a portion of the outflow side 450' of the suture band 448'. The lateral segment 478 of the first side cut 472 extends from the longitudinal segment 476 to and through the outflow side 450'. The second side cut 474 similarly includes a longitudinal segment 480 and a lateral segment 482. The longitudinal segment 480 of the second side cut 474 extends relatively near and parallel with a portion of the inflow side 452'. As such, the longitudinal segment 476 of the first side cut 472 is positioned opposite the longitudinal segment 480 of the second side cut 474. The lateral segment 482 extends from the longitudinal segment 480 to and through the inflow side 452'. As such, the lateral segment 482 of the first side cut 472 extends opposite the lateral segment 478 of the second side cut 474.

In one embodiment, the lateral segments 478 and 482 are angled towards the opposite end of the longitudinal segments 476 and 480 as the lateral segments 478 and 482 progress from the outer surface 456' to the inner surface 454'. In a preferred embodiment, the lateral segments 478 and 482 are aligned with one another as are the longitudinal segments 476 and 480 along the suture band 472. Notably, each of the engagement sections 470 are spaced from one another such that each engagement section 470 does not abut the neighboring or adjacent engagement section 470.

The outer surface 456' of the suture band 448', more particularly, the connecting body 471, defines a at least one lateral stop rib 484 extending between the longitudinal segment 476 of the first side cut 472 and the longitudinal segment 480 of the second side cut 474. Each lateral stop rib 484 extends outwardly from the remainder of the outer surface 456', a distance sufficient to impede suture movement over the lateral stop rib 484 in at least a first direction. In one embodiment, the lateral stop rib 484 is angled away from the lateral segments 478 and 482 of the side cuts 472 and 474, respectively. In one preferred embodiment, the suture band 448' is formed of a biocompatible, anti-thrombogenic material. In a preferred embodiment, the suture band 448' is formed of titanium, stainless steel, or other metal alloy. In one embodiment, there are twenty-four engagement sections 470 periodically positioned around the suture band 448', although other numbers are acceptable. During assembly, the suture band 448' is secured within the groove 446 of the rim 438.

Additionally referencing FIG. 38, during use, the heart valve mechanism 430 is positioned and sutures 304 are threaded relative to the engagement sections 470 as previously described with respect to tabs 458. However, with the suture band 448' each suture 304 is pulled from a first position through the side cuts 372 and 374 and over the lateral stop ribs 484 to a second or locked position "N."

In particular, a surgeon (not shown) pulls the suture 304 from the first position "M" on the outer surface 456' through the lateral segments 478 and 482 of the first and second side cuts 472 and 474 to the inner surface 454'. As the suture 304 is pulled inwardly through the lateral segments 478 and 482, a portion of the suture 304 remains on the outer surface 480 between the side cuts 472 and 474. The suture 304 is then pulled circumferentially along the longitudinal segments 476 and 480 of the engagement section 470 away from the lateral segments 478 and 482. In particular, the portion of the suture 304 remaining along the outer surface 456' is pulled over each lateral stop rib 484 positioned between the longitudinal segments 476 and 480. The angled orientation of the lateral stop rib 484 allows the suture 304 to be easily slid along the longitudinal segments 476 and 480 away from the lateral segments 476 and 480 of the respective side cuts 472 and 474, but does not allow the sutures 304 to be easily slid over the lateral stop ribs 484 back towards the lateral segments 476 and 480. Otherwise stated, the lateral stop rib 484 impedes the suture 304 from passing back over the lateral stop rib 484 to exit the suture band 448' prematurely. In one embodiment, the suture 304 is also tightly maintained partially within the groove 446 between the rim 438 and the suture band 448' on either side of the connecting body 471.

Upon passing over each lateral stop rib 484, the suture 304 is locked in position "N." Notably, the locked position "N" of the suture 304 is at least partially defined near or along an outer periphery or external boundary of the rim 438 with respect to the center of the suture band 448'. The process of pulling each suture 304 from position "M" to position "N" is repeated for each of the sutures with respect to each engagement section 470. Upon positioning each of the sutures 304 in position "N," each suture 304 can be trimmed and the excess suture 304 (i.e., the portion of the suture 304 extending beyond the outflow flange 482' of the rim 438) discarded. Notably in position "N," each suture 304 is securely held in place with respect to the suture locking assembly ring 432', and therefore, the heart valve mechanism 430 is securely held in place with respect to the valvular rim 60. Notably, the heart valve mechanism 430 is held in place with respect to the valvular rim 60 in a manner characterized by the absence of suture knots.

Figure 40:
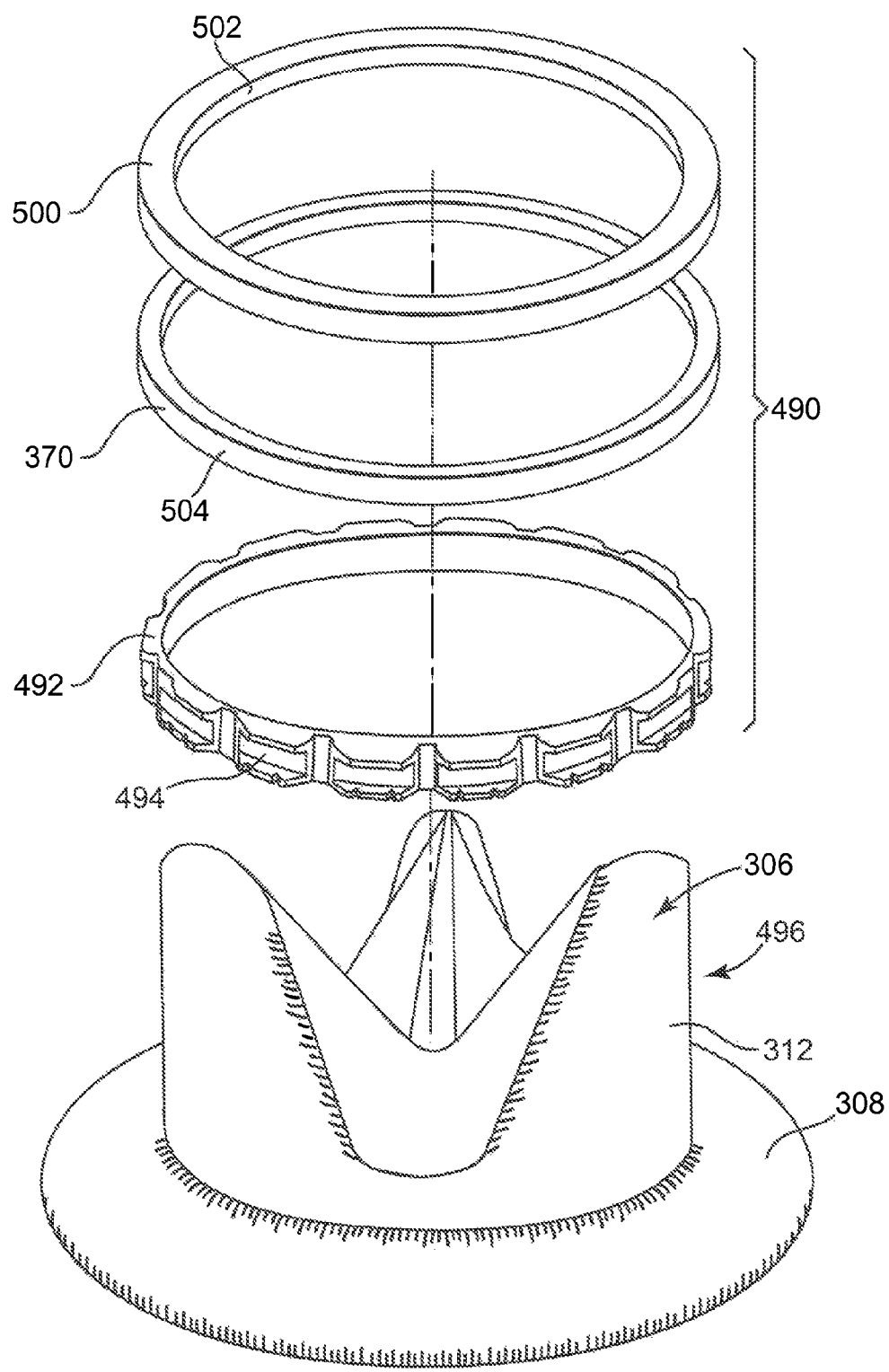
FIG. 40 is a perspective view of one embodiment of a heart valve mechanism and a suture locking assembly according to the present invention.

Yet another embodiment of the present invention is illustrated in FIG. 40 as suture locking assembly 490. The suture locking assembly 490 is similar to the suture locking assembly 302' (FIG. 36) described above except for those characteristics specifically described herein. In particular, the suture locking assembly 490 includes a rim 492 and the suture band 370. The rim 492 is similar to the rim 320' (FIG. 36), however, the rim 492 is not formed as part of the stent frame 310 (FIG. 36) of the heart valve mechanism 300 (FIG. 36). Rather, the rim 492 is formed of a plastic material, such as but not limited to acetyl homopolymer and polypropylene.

During assembly the suture band 370 is coupled with the rim 492 in a similar manner as the suture band 370 is coupled with the rim 320' (FIG. 36) above. More particularly, the rim 492 defines a groove 494, which receives and securely maintains the suture band 370. The suture band 370 and the rim 492 form the suture locking assembly 490 configured for use with a heart valve mechanism 496. The heart valve mechanism 496 is similar to the heart valve mechanism 300' (FIG. 36) however, the heart valve mechanism 496 does not form the rim 320', and the heart valve mechanism 496 is fully covered by the stent fabric 312. The suture locking assembly 490 is slipped over the heart valve mechanism 496, more specifically, over the fabric covered stent 306 of the heart valve mechanism 496 until positioned to abut the sewing ring 308. Upon positioning of the suture locking assembly 490 over the heart valve mechanism 496, the heart valve mechanism 496 with the suture locking assembly 490 is used in a similar manner as described above with respect to the heart valve mechanism 300' with the suture locking assembly 302'.

In one embodiment, the suture locking assembly 490 optionally includes a plastic cover 500. The plastic cover 500 is substantially ring-shaped and defines an inner surface 502 sized slightly larger but substantially equal to a outside surface 504 of the suture band 370. In such an embodiment, the plastic cover 500 is slid over and snap fit to the suture band 370 after placement within the rim 492. Addition of the plastic cover 500 prevents contact of the suture band 370 with patient internal tissue (not shown). Notably, the optional plastic cover 500 can be incorporated in any of the embodiments described above and not just the suture locking assembly 490.

Figure 41:
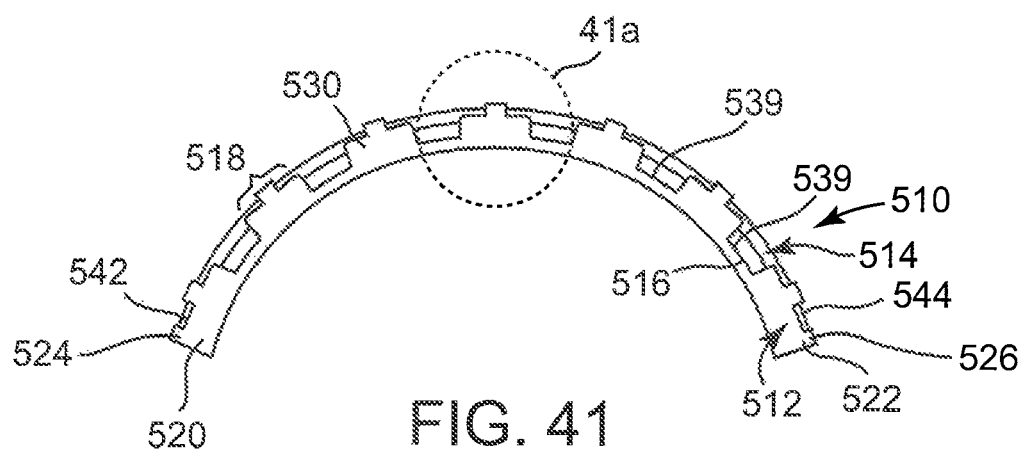
FIG. 41 is a top view of one embodiment of a suture locking assembly according to the present invention.
Figure 41A:
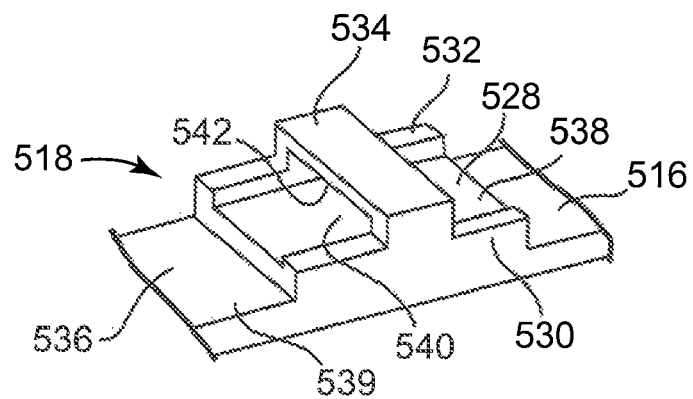
FIG. 41a is a perspective detail view of one embodiment of a rim of the suture locking assembly of FIG. 41.
Figure 42:
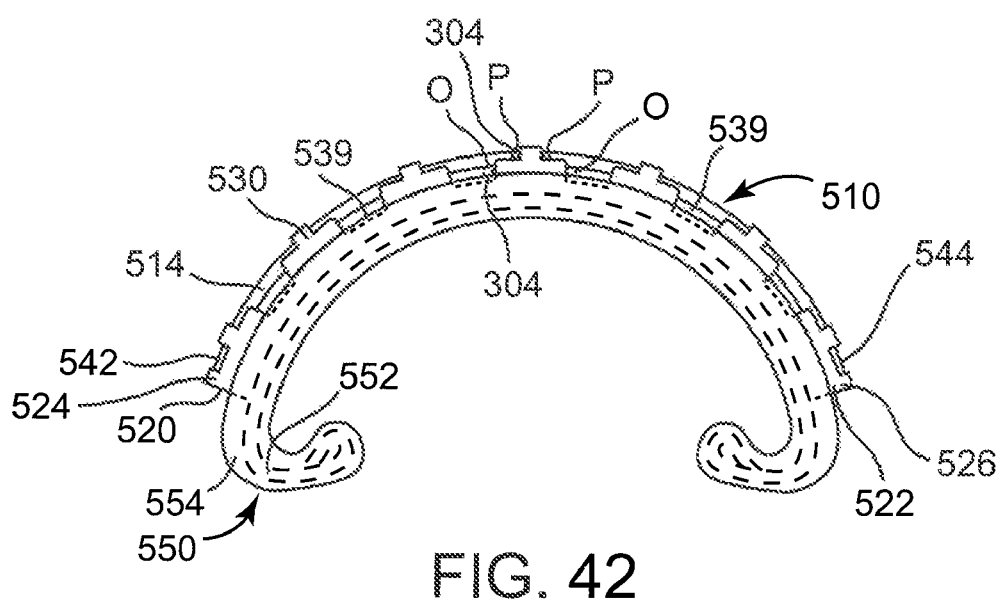
FIG. 42 is a top view of the suture locking assembly of FIG. 41 and an annuloplasty ring.

The suture locking assembly according to the present invention can be used with other implantable medical devices. FIGS. 41-42 generally illustrate one example embodiment of such a suture locking assembly 510. The suture locking assembly 510 includes a rim 512 and a suture band 514. The rim 512 defines a rim wall 516 and a plurality of segments 518 periodically spaced and extending from the rim wall 516. The rim wall 516 is curvilinear and defines a first end 520 and a second end 522 opposite the first end 520. In one embodiment, the rim wall 516 is semi-annular. In one embodiment, a first end cap 524 and a second end cap 526 each extend outwardly and laterally from the rim wall 516 at the first end 520 and the and second end 522 of the rim wall 516, respectively.

Each of the plurality of segments 518 includes a secondary rim wall 528, a first flange 530, a second flange 532, and a plurality of band coupling members 534. In each of the segments 518, the secondary rim wall 528 extends outwardly from an outer surface 536 the rim wall 516 such that an outer surface 538 of the secondary rim wall 528 is offset from the outer surface 536. In one embodiment, the outer surface 538 of the secondary rim wall 528 is offset from the outer surface 536 of the rim wall 516 a distance greater than the diameter of the suture 304. Note that in effect a recess 539 is formed along the rim wall 516 between each of the segments 518. The first and second flanges 530 and 532 longitudinally extend from rim wall 516 opposite one another to flank the secondary rim wall 528. Notably, the secondary rim wall 528 extends outwardly from the rim wall 516 a distance that is less than the distance each of the flanges 530 and 532 extend from the rim wall 516. As such, a groove 540 is defined between the flanges 530 and 532 and the secondary rim wall 528. Each segment 518 further includes one of the band coupling members 534 extending laterally between the flanges 530 and 532. The band coupling member 534 defines an inner surface 542 that is offset from the outer surface 538 of the secondary rim wall 528.

The suture band 514 is similar to the suture band 370 (FIG. 32) except the suture band 514 is not annular. Rather the suture band 514 is an elongated, curvilinear and substantially rigid band defining a first end 542 and a second end 544. In one embodiment, the suture band 514 is semi-annular. During assembly, the suture band 514 is received and maintained by the rim 512 to form the suture locking assembly 510. In particular, the suture band 514 is thread between the outer surface 538 of the secondary rim wall 528 and the inner surface 542 of the band coupling member 534 at each segment 518. As such, the suture band 514 is secured within the groove 540 of each segment 518. In addition, the first and second ends 542 and 544 of the suture band 514 interact with the first and second end caps 524 and 526 to additionally secure the suture band 514 with respect to the rim 512. In particular the end caps 524 and 526 decrease or prevent longitudinal movement of the suture band 514 with respect to the rim 512.

As illustrated in FIG. 42, in one embodiment, the assembled suture locking assembly 510 is configured for use with a different heart valve repair device, namely an annuloplasty band 550, which includes a curvilinear stiffening element 552 covered with a fabric sheath 554. The stiffening element 552 is preferably a medically acceptable implantable biocompatible metal wire (not shown) overmolded with a biocompatible, biostable, implantable, medical grade elastomeric material (not shown), such as elastomeric thermoplastic polymers (e.g., polyurethane) or silicone (e.g., liquid silicone rubber (LSR)). The fabric sheath 554 is preferably a knitted polyester (e.g., Dacron™) fabric, although other woven and non-woven biocompatible fabrics may also be used. In an alternative embodiment, the heart valve repair device is an annuloplasty ring (not shown), which is similar to the annuloplasty band 550 but is substantially annular, having an annular or curvilinear suture locking assembly is attached in a similar manner as described with respect to the annuloplasty band 550.

During assembly of the annuloplasty band 550, the suture locking assembly 510, and more particularly, the rim 512, is positioned to longitudinally abut the stiffening element 552. The fabric sheath 554 is placed around the entire stiffening element 552 and a portion of the rim 512 of the suture locking assembly 510. In particular, the fabric sheath 554 is wrapped around at least a portion of the rim wall 512. In one embodiment, the fabric sheath 554 is sutured around the stiffening element 552 and at least a portion of the rim wall 512, and as such the suture locking assembly 510 is coupled with the annuloplasty band 550 via the fabric sheath 554.

During use, the annuloplasty band 550 is placed within a patient (not shown) and aligned with the valvular rim 60 (FIG. 32) of the patient. The surgeon (not shown) inserts a suture 304 on each side of each of the segments 518 between the rim wall 512 and the suture band 514 and into the valvular rim 60 at a first position "O." In one embodiment, the sutures 304 are all first placed through the annuloplasty band 550 and subsequently thread between the rim wall 512 and the suture band 514 in a similar manner as described with respect to the heart valve mechanisms 300, 300', and 300". Upon initial placement of the sutures 304, the annuloplasty band 550 is more precisely positioned with respect to the valvular rim 60. After the annuloplasty band 550 is in the desired position, each suture 304 is pulled from the first position "O" towards the center of the respective segment 518. In particular, each suture 304 is pulled to be pinched between the suture band 514 and the first flange 530, the outer surface 538 of the secondary rim wall 528 of the rim 512 in a second or locked position "P." After each of the sutures 304 is transitioned into the locked position "P," any excess length of the sutures 304 is cut and discarded. Notably, upon moving each suture 304 to the locked position "P" the sutures 304 are secured to the suture locking assembly, and thereby, the annuloplasty band 550 is secured to the valvular rim 60.

All patents and publications referenced herein are hereby incorporated by reference in their entireties.

FIG. 43 illustrates a suture holder 560 to facilitate transferring sutures 304 from the first suture position to the second locked position and for use with any of the suture locking assemblies 302, 302', 302'', 432, 490, and 510, and is shown in conjunction with the suture locking assembly 302. In one embodiment, the suture holder 560 includes a shaft 562, a holder support 564, a translating member 566, a spring 568, and a stop 570. The shaft 562 extends between a first end 572 and a second end 574. The holder support 564 is coupled with the shaft 562 at the first end 572 of the shaft 562. The holder support 564 defines a support surface 576 and at least one suture reception area 578. The support surface 576 is configured to interact with the suture locking assembly 302, thereby, supporting the suture holder 560 during use. As best illustrated with additional reference to FIG. 43a, the at least one suture reception area 578 extends from the support surface 576 to define an area for selectively receiving a suture 304. In one embodiment, the suture reception area 578 includes a suture reception cavity or cutout 579 through which the suture 304 extends during use. The suture reception cavity 579 is configured to partially guide the suture 304 between the suture locking assembly and the translating member. In one embodiment, the holder support 564 defines a plurality of suture reception areas 578 each having a suture reception cavity 579 configured to receive a suture 304.

The translating member 566 includes a main body 580 and at least one suture interface arm 582. The main body 580 is circumferentially and slidably mounted on the shaft 562. More specifically, the main body 580 is slidably coupled to the shaft 562 between the first end 572 and the second end 574. As such, the main body 580 is coupled to the shaft 562 in a manner allowing the translating member 566 to translate up and down at least a portion of the shaft 562.

The suture interface arm 582 extends radially from the main body 580, and as such, is radially offset from the shaft 562. The suture interface arm 582 includes at least one holding feature 584. Each holding feature 584 is configured to selectively receive and maintain a suture 304. In one embodiment, the holding feature 584 is a cavity, hook, or pinch site adapted to receive and maintain the suture 304 during use. In one embodiment, the at least one holding feature 584 is a groove circumferentially machined around suture interface arm 582. In one embodiment, the suture interface arm 582 defines a plurality of holding features 584 each adapted to selectively receive and maintain a single suture 304. In one embodiment, the translating member 566 includes two suture interface arms 582 extending from main body 580 opposite one another (i.e. 180° apart from one another).

Translation of the main body 580 is facilitated by the spring 568 mounted around the shaft 562 between the second end 574 of the shaft 562 and the main body 580 of the translating member 566. The spring 568 is any spring or other resilient member having a neutral position and a compressed position. As illustrated in FIG. 43, the spring 568 is initially in a neutral position. As such, the spring 568 maintains the translating member 566 spaced from the second end 574 of the shaft 562.

The stop 570 is positioned on the shaft 562 between the translating member 566 and the holder support 564. The stop 570 serves to prevent movement of the translating member 566 beyond the stop 570 to a portion of the shaft 562 between the stop 570 and the holder support 564. In one embodiment, the stop 570 is a washer, a pin, or other suitable stop device secured to the shaft 562 by friction fit, glue, coupling device, etc. In one embodiment, the stop 570 is a flange integrally formed with the shaft 562. In other embodiments, the stop 570 is defined by any structural arrangement preventing movement of the translating member 566 to the portion of the shaft between the stop 570 and the holder support 564, such as at an interface (not shown) between a top and bottom portion (not shown) of the shaft 562 where the bottom portion of the shaft 562 has a larger diameter than the top portion, etc.

Figure 43B:
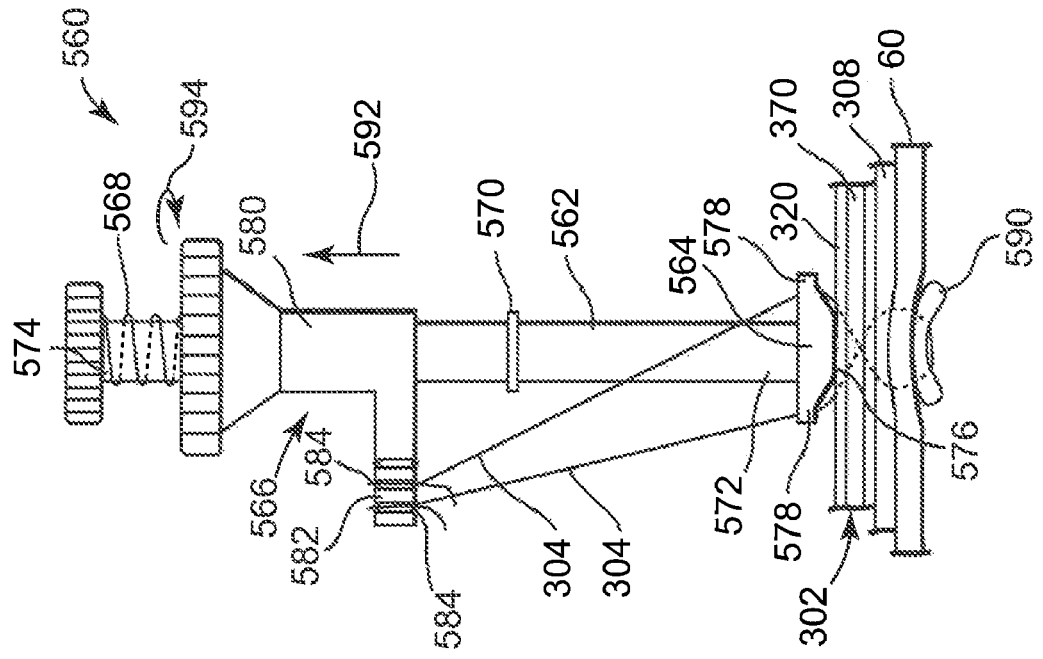
FIG. 43b is a side view of the suture holder of FIG. 43 in a second position.

During use, and with additional reference to FIG. 43b, the plurality of sutures 304 are sewn through the suture locking assembly 302, the sewing ring 308, and the valvular rim 60 as described above (i.e., before connection to the suture holder 560). Notably, only the sewing ring 308 of the heart valve mechanism is illustrated in FIGS. 43 and 43b for illustrative purposes only. In one embodiment, the sutures 304 are additionally sewn through a pledget 590 to prevent the sutures 304 from cutting into the valvular rim 60. The pledget 590 can be used in any of the embodiments described above.

Once the sutures 304 are positioned in their first sutured positioned as illustrated in FIG. 43, the suture holder 560 is positioned upon the suture locking assembly 302 near a suture 304 or a pair of sutures 304. In particular, the suture holder 560 is placed such that the support surface 576 rests upon and is supported by the suture locking assembly 302. Individual sutures 304 are placed through individual ones of the suture reception cavities 579 and extend upward to and are each secured to an individual holding feature 584 of the suture interface arm 582. In one embodiment, the physician (not shown) wraps, ties, or pinches the suture 304 within each holding feature 584 to secure the suture 304 to the suture interface arm 582. In one embodiment, in which the translating member 566 includes two suture interface arms 582, one end of the suture 304 is secured to one suture interface arm 582 and the opposite end of the suture 304 is secured to the other suture interface arm 582.

Upon securing the suture(s) 304 to the suture interface arm 582, the physician applies force to the main body 580 as indicated by the direction arrow 592 in FIG. 43b. In particular, the physician asserts a force on the main body 580 moving the translating member away from the stop 570 towards the second end 574, thereby, compressing the spring 568. By applying the force to the translating member 562, not only does the translating member 566 move towards the second end 574, but also, the sutures 304 are pulled taut and transition to their respective second locked position as described in detail above. In one embodiment, the physician applies a rotating force indicated by arrow 594 in addition to linear force 592. As such, the translating member 566 additionally rotates along the shaft 562 to facilitate positioning of the sutures 304 in the respective second positions.

Once the physician (not shown) has transitioned the sutures 304 to their second or locked positions via movement of the translating member 566, the physician removes the force 592 applied to the main body 588 causing the spring 568 to relax and the translating member 566 to return to the stop 570. The physician then removes the sutures 304 from the holding features 584 and knots and/or trims the sutures 304 as described above. Following use of the suture holder 560 on a suture or suture pair 304, the physician moves the suture holder 560 to another suture 304 or suture pair 304 to repeat the described process until all sutures 304 are secured in their second or locked positions. Notably, this is but one example embodiment of a suture holder 560 for use with the suture locking assemblies 302, 302', 302", 432, 490, and 510 and other suture holders are equally acceptable.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto, including monitors, now known and coming into existence during the term of the patent. Thus, it is expected that various changes, alterations, or modifications may be made to the invention as described herein without departing from the spirit and scope of the invention as defined by the appended claims.

What is claimed is:

1. A method of implanting a heart valve repair device, the method comprising: providing a heart valve repair device;
   receiving a suture locking assembly including:
   a rim extending along an outer periphery of the heart valve repair device, the rim defining a first flange and a second flange spaced from the first flange, and
   a suture band maintained between the first flange and the second flange;
   positioning the heart valve repair device, and the suture locking assembly within a patient;
   sewing a suture through a patient's valvular rim in a first position relative the rim and the suture band;
   wherein the suture extends at least partially between the rim and the suture band in the first position; and
   pulling the suture to a second position relative the rim and the band, wherein the suture is secured with respect to the rim and the suture band in the second position, the second position is at least partially defined near an outer periphery of the rim;
   wherein securing the suture in the second position at least partially secures the heart valve repair device with respect to the patient's valvular rim.

2. The method of claim 1, wherein the suture extends at least partially between the rim and the suture band in the second position.

3. The method of claim 1, wherein the rim is integrally formed with the heart valve repair device.

4. The method of claim 1, wherein the rim is formed separately from the heart valve repair device.

5. The method of claim 1, wherein the step of receiving a suture locking assembly includes placing the rim adjacent an external portion of the heart valve repair device.

6. The method of claim 1, wherein the rim forms a plurality of lateral recesses periodically spaced about the rim, each of the lateral recesses defining a first position for one of the plurality of sutures, and the step of sewing a suture in a first position is repeated for each of the plurality of lateral recesses.

7. The method of claim 6, wherein pulling the sutures to a second position includes pulling each of the sutures in a first direction with respect to the first position of the suture.

8. The method of claim 6, wherein the step of sewing a suture in a first position is repeated twice for each of the plurality of lateral recesses.

9. The method of claim 8, wherein pulling the sutures to a second position includes pulling at least one of the sutures from the first position in a first direction and pulling at least one of the other sutures from the first position in a second direction to cross the sutures pulled in the first and second directions.

10. The method of claim 9, wherein sewing a suture in a first position for each of the plurality of recesses includes crossing two of the suture with one another.

11. The method of claim 6, wherein the rim defines a plurality of second positions, each second position being spaced between each of the plurality of lateral recesses, the step of pulling the suture to a second position is repeated for each of the sutures sewn in a first position.

12. The method of claim 6, wherein the rim defines a plurality of second positions, two second positions being defined between each of the plurality of lateral recesses, the step of pulling a suture to a second position is repeated for each of the sutures sewn in a first position.

13. The method of claim 1, wherein the suture band defines a U-shaped cutout, and pulling the suture to a second position includes pulling the suture into the U-shaped cutout.

14. The method of claim 1, wherein the suture band defines an engagement section including a connecting body flanked by an outflow cut and an inflow cut, and pulling the suture to a second position includes pulling the suture through the inflow and outflow cuts.

15. The method of claim 14, wherein the suture band defines at least one lateral stop, and pulling the suture to a second position includes pulling the suture over the at least one lateral stop rib.

16. The method of claim 1, wherein sewing a suture in a first position is repeated for a plurality of sutures, and pulling the suture to a second position includes forming a hitch with two adjacent sutures.

17. The method of claim 16, wherein pulling the suture to a second position includes pulling the hitch to position the hitch between the rim and the suture band.

18. The method of claim 1, wherein the step of pulling the sutures to a second position includes using a suture holder to pull the sutures.

* * * * *